United States Patent
Stallings et al.

(10) Patent No.: US 11,129,816 B2
(45) Date of Patent: Sep. 28, 2021

(54) RING-FUSED THIAZOLINO 2-PYRIDONES IN COMBINATION WITH A DRUG AGAINST TUBERCULOSIS

(71) Applicants: QURETECH BIO AB, Umeå (SE); Washington University in St. Louis, St. Louis, MO (US)

(72) Inventors: Christina Leigh Stallings, St. Louis, MO (US); Gregory Alexander Harrison, St. Louis, MO (US); Fredrik Almqvist, Umeå (SE); Souvik Sarkar, Umeå (SE)

(73) Assignees: Quretech Bio AB, Umeå (SE); Washington University in St. Louis, St. Louis, MO (US)

( * ) Notice: Subject to any disclaimer, the term of this patent is extended or adjusted under 35 U.S.C. 154(b) by 0 days.

(21) Appl. No.: 16/652,829

(22) PCT Filed: Oct. 5, 2018

(86) PCT No.: PCT/EP2018/077222
§ 371 (c)(1),
(2) Date: Apr. 1, 2020

(87) PCT Pub. No.: WO2019/068910
PCT Pub. Date: Apr. 11, 2019

(65) Prior Publication Data
US 2020/0316036 A1    Oct. 8, 2020

Related U.S. Application Data

(60) Provisional application No. 62/568,430, filed on Oct. 5, 2017, provisional application No. 62/716,054, filed on Aug. 8, 2018.

(51) Int. Cl.
A61K 31/437     (2006.01)
A61K 45/06      (2006.01)

(52) U.S. Cl.
CPC .......... A61K 31/437 (2013.01); A61K 45/06 (2013.01)

(58) Field of Classification Search
None
See application file for complete search history.

(56) References Cited

FOREIGN PATENT DOCUMENTS

| WO | WO 2011/113606 A1 | 9/2011 |
| WO | WO 2012/143796 A2 | 10/2012 |
| WO | WO 2014/185853 A1 | 11/2014 |
| WO | WO 2015/014993 A2 | 2/2015 |
| WO | WO 2016/075296 A1 | 5/2016 |
| WO | WO 2017/175182 A1 | 10/2017 |

OTHER PUBLICATIONS

Aberg, et al., "Microwave-assisted decarboxylation of bicyclic 2-pyridone scaffolds and identification of Ab-peptide aggregation inhibitors", Org. Biomol. Chem., 2005, 3, 2817-2823.
Aberg, et al., "Carboxylic acid isosteres improve the activity of ring-fused 2-pyridones that inhibit pilus biogenesis in *E. coli*", Bioorganic & Medicinal Chemistry Letters 18 (2008) 3536-3540.
Bengtsson et al: "Design, synthesis and evaluation of triazole functionalized ring-fused 2-pyridones as antibacterial agents",European Journal of Medicinal Chemistry,vol. 54, (2012), pp. 637-646.
Chorell et al., "Diverse Functionalization of Thiazolo Ring-Fused 2-Pyridones", J. Org. Chem. 2007, 72, 4917-4924.
Chorell et al., "Design and Synthesis of C-2 Substituted Thiazolo and Dihydrothiazolo Ring-Fused 2-Pyridones: Pilicides with Increased Antivirulence Activity", J. Med. Chem. 2010, 53, 5690-5695.
Chorell et al., "Mapping pilicide anti-virulence effect in *Escherichia coli*, a comprehensive structure—activity study", Bioorganic & Medicinal Chemistry 20 (2012) 3128-3142.
Emtenas et al., "Design and Parallel Solid-Phase Synthesis of Ring-Fused 2-Pyridinones That Target Pilus Biogenesis in Pathogenic Bacteria", J. Comb. Chem. 2002, 4, 630-639.
Good et al., "Thiazolino 2-Pyridone Amide Inhibitors of Chlamydia trachomatis Infectivity", J. Med. Chem. (2016), 59, 2094-2108.
Good et al., "Attenuating Listeria monocytogenes Virulence by Targeting the Regulatory Protein PrfA", Cell Chemical Biology 23, 404-414 (2016).
Pemberton et al., "Functionalization of bicyclic 2-pyridones targeting pilus biogenesis in uropathogenic *Escherichia coli*",Tetrahedron Letters 48 (2007) 4543-4546.

(Continued)

*Primary Examiner* — Zinna Northington Davis
(74) *Attorney, Agent, or Firm* — Ballard Spahr LLP

(57) ABSTRACT

Described is a composition that includes:
(i) a drug against tuberculosis inhibiting the cytochrome b subunit of the bc1 complex, said cytochrome b subunit being encoded by the gene qcrB, in *Mycobacterium tuberculosis*, or a pharmaceutically acceptable salt thereof, and
(ii) a compound of Formula II,

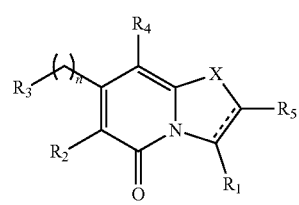

or a pharmaceutically acceptable salt thereof.

19 Claims, 3 Drawing Sheets

(56) References Cited

OTHER PUBLICATIONS

Pethe et al., "Discovery of Q203, a potent clinical candidate for the treatment of tuberculosis", Nat Med. Sep. 2013;19(9):1157-60.
International Search Report and Written Opinion dated Jan. 23, 2019 by the International Searching Authority for International Application No. PCT/EP2018/077222, filed on Oct. 5, 2018 and published as WO 2019/068910 on Apr. 11, 2019 (Applicant-QURETECH BIO AB et al) (12 Pages).
Aberg, et al."C-Terminal properties are important for ring-fused 2-pyridones that interfere with the chaperone function in uropathogenic *E. coli*", Org. Biomol. Chem., 2005, 3, 3886-3892.

Rifampicin

Pyrazinamide

Ethambutol

Bedaquiline                              Ethionamide

Delamanide

Pretomanid

RING-FUSED THIAZOLINO 2-PYRIDONES IN COMBINATION WITH A DRUG AGAINST TUBERCULOSIS

CROSS-REFERENCE TO RELATED APPLICATIONS

This application is a U.S. National Phase Application of International Application No. PCT/EP2018/077222, filed Oct. 5, 2018, which claims the benefit of U.S. Provisional Application Nos. 62/568,430, filed Oct. 5, 2017, and 62/716,054, filed Aug. 8, 2018, each of which are hereby incorporated by reference in their entirety.

TECHNICAL FIELD

The present disclosure relates to ring-fused thiazolino 2-pyridones, to processes for preparing such compounds, to their use in treating and/or preventing tuberculosis infections, to methods for their therapeutic use and to a pharmaceutical composition containing any such compounds. In particular, the present disclosure relates to said ring-fused thiazolino 2-pyridones in combination with a drug against tuberculosis, to the use of such a combination in treating and/or preventing tuberculosis infections, to methods for its therapeutic use and to a pharmaceutical composition containing any such combinations.

BACKGROUND

Tuberculosis (TB) infects at least 30% of the world's population. Every year there are about 9 million newly infected patients, and about 1.5 million deaths. A major roadblock in treating tuberculosis (TB) is the recalcitrance of *Mycobacterium tuberculosis* (Mtb) to currently available antibiotics, which necessitates lengthy treatment regimens that do not always eradicate the tuberculosis bacteria.

The main cause of TB is *Mycobacterium tuberculosis* (Mtb). However, there are also other tuberculosis causing mycobacteria such as *M. bovis, M. africanum, M. canetti*, and *M. microti*.

Patients suffering from tuberculosis may have active tuberculosis or latent tuberculosis. Active tuberculosis means that tuberculosis bacteria are reproducing and spreading in the body, causing tissue damage. A patient infected with active tuberculosis feels sick. Common symptoms are cough that does not go away, coughing blood and weight loss. Further, a patient suffering from active tuberculosis is infectious, i.e. can spread tuberculosis to other people. The tuberculosis is spread through the air when the patient talks, coughs, sneezes etc.

Latent tuberculosis, which may also be denominated dormant, chronic or persistent tuberculosis, means that tuberculosis bacteria do not multiply to detectable levels in the body. Commonly, a person infected with latent tuberculosis has no symptoms and is not infectious. The dormant phase can last for a very long time, even during the whole life time of the infected person. However, the tuberculosis infection may be reactivated into active tuberculosis. In particular, this may happen in patients having an immune system deficiency or taking immunosuppressive agents.

Exposure to tuberculosis can be detected through a tuberculin skin test or blood test. There is currently no diagnostic test that can distinguish between patients that have been exposed and cleared an infection versus someone who is latently infected. Active pulmonary tuberculosis is detected through sputum smears or culturing of sputum.

Current treatment and prophylactics of drug susceptible tuberculosis are based on combination therapies including isoniazid (isonicotinylhydrazide, INH). In the standard clinical practice, isoniazid is used in combination with rifampicin (RIF), ethambutol (EMB) and pyrazinamide (PZA) in a 6 month regimen to treat drug-susceptible active Mtb infection. The long duration of antibiotic therapy has serious side effects, and eradication of tuberculosis bacteria is often incomplete. Further, this long-term antibiotic therapy has resulted in the rise of drug resistant tuberculosis, such as multidrug resistant tuberculosis, which constitutes 3.5% of new tuberculosis cases and 20% of previously treated cases. In addition, people infected with latent Mtb are prophylactically treated with 9 months of INH or 12 weeks of INH and rifapentine to prevent reactivation of the bacteria.

Mtb infecting a patient may be divided into so-called nonpersisters and persisters. While nonpersister bacteria may be eradicated with commonly used tuberculosis antibiotics, the persisters are tolerant of such antibiotics. The recalcitrance of Mtb persisters to therapy has led to an increase in drug resistance.

Thus, the frequent lack of complete tuberculosis eradication, drug resistance and/or the long treatment times are major challenges associated with current tuberculosis treatment.

PCT/EP2015/076578 discloses ring-fused thiazolino 2-pyridones, to processes for preparing such compounds, to their use in treating and/or preventing bacterial infections such as Chlamydia. It is mentioned that the ring-fused thiazolino 2-pyridones may be administered in combination with another therapeutic agent such as an antibiotic. It is not mentioned to use ring-fused thiazolino 2-pyridones for inhibition of biofilm formation or treating tuberculosis.

WO 2014/185853 discloses ring-fused 2-pyridones shown to reduce the infectivity of Chlamydia. Treatment of tuberculosis is not mentioned.

WO 2011/113606 discloses small molecule compounds and their use in bacterial infections, in particular tuberculosis. The compound 6-chloro-2-ethyl-N-[(4-{4-[4-(trifluoromethoxy)phenyl]piperidin-1-yl}phenyl)methyl]imidazo[1,2-a]pyridine-3-carboxamide is mentioned.

WO 2015/014993 discloses small molecule compounds and their use in bacterial infections, in particular tuberculosis.

WO 2012/143796 discloses small molecule compounds and their use in the treatment of inflammatory diseases, in particular asthma, chronic obstructive pulmonary disease (COPD), inflammation post infection, arthritis, atherosclerosis, pain and dermatitis. It is stated that examples of inflammatory diseases or disorders include, without limitation, asthma, lung inflammation, COPD, inflammation post infection, atherosclerosis, pain, dermatitis, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, ulcers, Sjogren's syndrome, Reiter's syndrome, psoriasis, pelvic inflammatory disease, orbital inflammatory disease, thrombotic disease, and inappropriate allergic responses to environmental stimuli such as poison ivy, pollen, insect stings and certain foods, including atopic dermatitis and contact dermatitis.

There is a need for alternative and/or improved treatments of tuberculosis. In particular, there is a need for treatment of tuberculosis that shortens the duration of the treatment, decreases the rates of drug resistance and/or allows for complete or nearly complete tuberculosis eradication.

It is an object of the present disclosure to provide compounds useful in the treatment and/or prevention of tuberculosis. Further, it is an object of the present disclosure to provide compounds that may be used in combination with current therapeutic agents such as isoniazid to improve treatment and/or prevention of tuberculosis.

SUMMARY

The present disclosure provides a combination comprising:

(i) a drug against tuberculosis inhibiting the cytochrome b subunit of the bc1 complex, said cytochrome b subunit being encoded by the gene qcrB, in *Mycobacterium tuberculosis*, or a pharmaceutically acceptable salt thereof; and (ii) a compound of Formula II

II

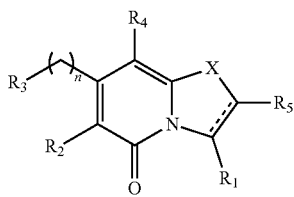

or a pharmaceutically acceptable salt thereof, wherein $R_1$ is selected from the group consisting of:

a) C(O)OH, b) tetrazolyl, c) $CH_2OH$, d) $C(O)NR_{6a}R_{6b}$, e) $C(O)NHSO_2R_7$, f) $C(O)OR_8$, g) $NH_2$, h) H, i)

j)

k)

and l) imidazole carboxylate, $R_2$ is selected from the group consisting of:

a) H, b) Cl, F, Br or I, c) $CH_2OH$, d) $C_1$-$C_4$alkyl, and e) $NY_1Y_2$, $R_3$ is selected from the group consisting of:

a) 1-naphtyl, 2-naphtyl or 1-naphtyloxy, each independently substituted with 0, 1, 2 or 3 substituents selected from the group consisting of methyl, fluoro, chloro, bromo, cyano and methoxy, b) phenyl substituted with 0, 1, 2 or 3 substituents independently selected from the group consisting of methyl, fluoro, chloro, cyano and trifluoromethyl, c) aminophenyl substituted with 0, 1, 2 or 3 substituents independently selected from the group consisting of methyl, fluoro, chloro and trifluoromethyl d) 2-(3-methyl)phenylmethylene, e) benzothiophen-2-yl f) H, g) $C_1$-$C_4$alkyl, h) 2-methyl-1-aza-2-bora-1H-naphth-5-yloxy, i) 2-methyl-1-aza-2-bora-1H-naphth-5-yl, j) isoxazol-5-yl optionally substituted with methyl, 1-naphthyl, 2-naphtyl, 1-anthryl, m-trifluoromethylphenyl, 3,5-ditrifluoromethylphenyl, 3,4-methylenedioxyphenyl, thiophene or phenyl, k) isoxazol-3-yl substituted with m-trifluoromethylphenyl or 1-naphtyl, l) benzoxazole-2-yl, and m)

$R_4$ is selected from the group consisting of:

a) $C_1$-$C_4$alkyl substituted by 0, 1, 2, 3 or 4 fluoro;

b) $C_3$-$C_6$cycloalkyl, c) $C_1$-$C_4$alkoxy substituted by 0, 1, 2, 3 or 4 fluoro, d) $C_3$-$C_6$cycloalkoxy, e) a 3-, 4-, 5- or 6-membered heterocycle, substituted with 0 or 1 substituent selected from the group consisting of phenyl and 1-naphthyl, f) N-methyl 3-indolyl, g) $NR_{9a}R_{9b}$, and h) $C_2$-$C_4$alkynyl, $R_5$ is selected from the group consisting of:

a) H, b) phenyl substituted with 0, 1, 2 or 3 methyl group(s), c) benzyl, d) thienyl,
e) $C_1$-$C_4$alkoxy, and
f) a 3-, 4-, 5- or 6-membered heterocycle,
and in the above definitions:
$R_{6a}$ is selected from the group consisting of H and $C_1$-$C_4$alkyl,
$R_{6b}$ is selected from the group consisting of H, $C_1$-$C_4$alkyl, $C_1$-$C_4$alkoxy and isonicotinoylamino;
$R_7$ is $C_1$-$C_4$alkyl or phenyl,
$R_8$ represents 2-{2-[1-(hydroxymethyl)propylamino]ethylamino}butyl),
$R_{9a}$ represents $C_1$-$C_4$alkyl,
$R_{9b}$ represents $C_1$-$C_4$alkyl,
$R_{10}$ represents H; $C_1$-C4alkyl substituted with 0, 1, 2 or 3 F; benzyl substituted with 0 or 1 trifluoromethyl; or naphtalen-1-yl-methylene,
$Y_1$ and $Y_2$ each independently represents hydrogen, methyl, $CH_3S(O)_2$ or
$C(O)CH_3$, or
$Y_1$ and $Y_2$ together form $CH_2CH_2CH_2CH_2$ or $CH_2CH_2CH_2CH_2CH_2$,
m is 0 or 1,
n is 0 or 1,
X is S, SO or $SO_2$, and
Z represents $C_1$-$C_4$alkyl substituted with 0, 1, 2 or 3 F; $C_1$-$C_4$alkoxy substituted with 0, 1, 2 or 3 F; or a halogen selected from Cl, F. Br or I.

There is also provided a combination as described herein or a compound of Formula II as described herein for use as a medicament in therapy.

Further, there is provided a combination as described herein or a compound of Formula II as described herein for use in the treatment and/or prevention of tuberculosis.

Further, there is provided the use of a combination as described herein or a compound of Formula II as described herein for the manufacture of a medicament for the treatment and/or prevention of tuberculosis.

There is also provided a method for treatment and/or prevention of comprising administering to a mammal, such as a human or an animal, in need thereof an effective amount of a combination as described herein or a compound of Formula II as described herein.

There is also provided a compound of Formula II which is one or more of the following:

1H-imidazol-1-ium 7-(benzo[d]oxazol-2-yl)-8-cyclopropyl-5-oxo-3,5-dihydro-2H-thiazolo[3,2-a]pyridine-3-carboxylate, 1H-imidazol-1-ium 8-cyclopropyl-7-(3-(naphthalen-1-yl)isoxazol-5-yl)-5-oxo-3,5-dihydro-2H-thiazolo[3,2-a]pyridine-3-carboxylate, 1H-imidazol-1-ium 8-cyclopropyl-5-oxo-7-(3-(3-(trifluoromethyl)phenyl)isoxazol-5-yl)-3,5-dihydro-2H-thiazolo[3,2-a]pyridine-3-carboxylate, 1H-imidazol-1-ium 8-cyclopropyl-5-oxo-7-(3-(thiophen-2-yl)isoxazol-5-yl)-3,5-dihydro-2H-thiazolo[3,2-a]pyridine-3-carboxylate, 1H-imidazol-1-ium 8-cyclopropyl-5-oxo-7-(3-phenylisoxazol-5-yl)-3,5-dihydro-2H-thiazolo[3,2-a]pyridine-3-carboxylate, 1H-imidazol-1-ium 6-bromo-7-(naphthalen-1-ylmethyl)-5-oxo-8-(3-phenylisoxazol-5-yl)-3,5-dihydro-2H-thiazolo[3,2-a]pyridine-3-carboxylate, 1H-imidazol-1-ium 7-(naphthalen-1-ylmethyl)-5-oxo-8-(3-phenyl-4,5-dihydroisoxazol-5-yl)-3,5-dihydro-2H-thiazolo[3,2-a]pyridine-3-carboxylate, 1H-imidazol-1-ium 8-ethynyl-7-(naphthalen-1-ylmethyl)-5-oxo-3,5-dihydro-2H-thiazolo[3,2-a]pyridine-3-carboxylate, 1H-imidazol-1-ium 7-(naphthalen-1-ylmethyl)-5-oxo-8-(3-phenylisoxazol-5-yl)-3,5-dihydro-2H-thiazolo[3,2-a]pyridine-3-carboxylate, 1H-imidazol-1-ium 8-(3-(naphthalen-1-yl)isoxazol-5-yl)-7-(naphthalen-1-ylmethyl)-5-oxo-3,5-dihydro-2H-thiazolo[3,2-a]pyridine-3-carboxylate, 1H-imidazol-1-ium 8-cyclopropyl-7-(naphthalen-1-ylmethyl)-5-oxo-3,5-dihydro-2H-thiazolo[3,2-a]pyridine-3-carboxylate, 8-cyclopropyl-5-oxo-7-(5-(3-(trifluoromethyl)phenyl)isoxazol-3-yl)-2,3-dihydrothiazolo[3,2-a]pyridine-3-carboxylic acid, 8-cyclopropyl-7-(5-(naphthalen-1-yl)isoxazol-3-yl)-5-oxo-2,3-dihydrothiazolo[3,2-a]pyridine-3-carboxylic acid, 8-cyclopropyl-7-(3-(naphthalen-2-yl)isoxazol-5-yl)-5-oxo-2,3-dihydrothiazolo[3,2-a]pyridine-3-carboxylic acid, 1H-imidazol-1-ium 7-(3-(benzo[d][1,3]dioxol-5-yl)isoxazol-5-yl)-8-cyclopropyl-5-oxo-2,3-dihydrothiazolo[3,2-a]pyridine-3-carboxylate, 1H-imidazol-1-ium 7-(3-(anthracen-9-yl)isoxazol-5-yl)-8-cyclopropyl-5-oxo-2,3-dihydrothiazolo[3,2-a]pyridine-3-carboxylate, 7-(3-(3,5-bis(trifluoromethyl)phenyl)isoxazol-5-yl)-8-cyclopropyl-5-oxo-2,3-dihydrothiazolo[3,2-a]pyridine-3-carboxylic acid, 8-cyclopropyl-7-(3-methylisoxazol-5-yl)-5-oxo-2,3-dihydrothiazolo[3,2-a]pyridine-3-carboxylic acid, 7-(3-(tert-butylamino)imidazo[1,2-a]pyridin-2-yl)-8-cyclopropyl-5-oxo-2,3-dihydrothiazolo[3,2-a]pyridine-3-carboxylic acid, 7-(3-(benzylamino)imidazo[1,2-a]pyridin-2-yl)-8-cyclopropyl-5-oxo-2,3-dihydrothiazolo[3,2-a]pyridine-3-carboxylic acid, 8-cyclopropyl-7-(3-((naphthalen-1-ylmethyl)amino)imidazo[1,2-a]pyridin-2-yl)-5-oxo-2,3-dihydrothiazolo[3,2-a]pyridine-3-carboxylic acid, 8-cyclopropyl-5-oxo-7-(3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-6-chloroimidazo[1,2-a]pyridin-2-yl)-8-cyclopropyl-5-oxo-2,3-dihydrothiazolo[3,2-a]pyridine-3-carboxylic acid, 7-(6-chloro-3-((naphthalen-1-ylmethyl)amino)imidazo[1,2-a]pyridin-2-yl)-8-cyclopropyl-5-oxo-2,3-dihydrothiazolo[3,2-a]pyridine-3-carboxylic acid, 7-(3-(benzylamino)-6-chloroimidazo[1,2-a]pyridin-2-yl)-8-cyclopropyl-5-oxo-2,3-dihydrothiazolo[3,2-a]pyridine-3-carboxylic acid, 7-(6-chloro-3-((3-(trifluoromethyl)benzyl)amino)imidazo[1,2-a]pyridin-2-yl)-8-cyclopropyl-5-oxo-2,3-dihydrothiazolo[3,2-a]pyridine-3-carboxylic acid, 7-(3-(tert-butylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-7-(3-((naphthalen-1-ylmethyl)amino)-7-(trifluoromethyl)imidazo[1,2-a]pyridin-2-yl)-5-oxo-2,3-dihydrothiazolo[3,2-a]pyridine-3-carboxylic acid, 7-(3-(benzylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-5-oxo-7-(7-(trifluoromethyl)-3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((naphthalen-1-ylmethyl)amino)imidazo[1,2-a]pyridin-2-yl)-5-oxo-2,3-dihydrothiazolo[3,2-a]pyridine-3-carboxylic acid, 7-(3-(benzylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((3-(trifluoromethyl)benzyl)amino)imidazo[1,2-a]pyridin-2-yl)-5-oxo-2,3-dihydrothiazolo[3,2-a]pyridine-3-carboxylic acid or a pharmaceutically acceptable salt of any of the foregoing compounds.

DETAILED DESCRIPTION

Figure 1:
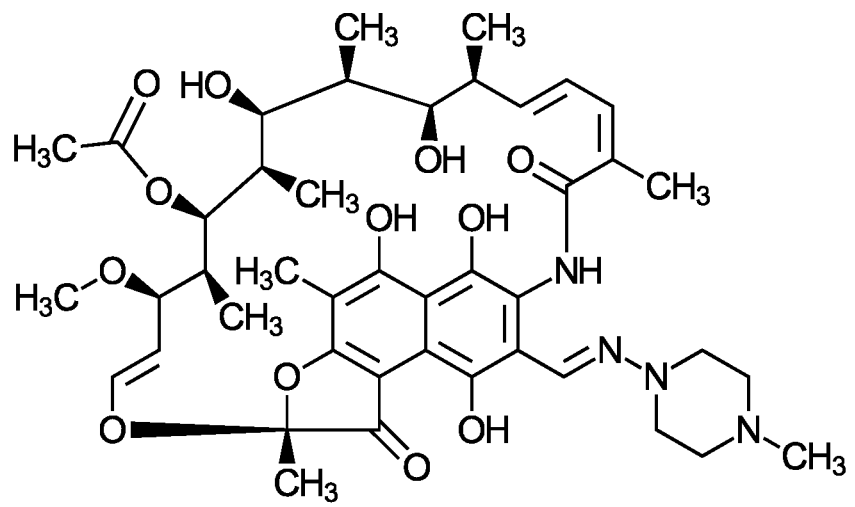
FIG. 1 shows the chemical structures of the drugs rifampicin (RIF), pyrazinamide (PZA) and ethambutol (EMB).
Figure 1:
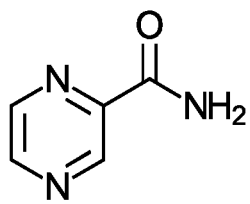
Figure 1:
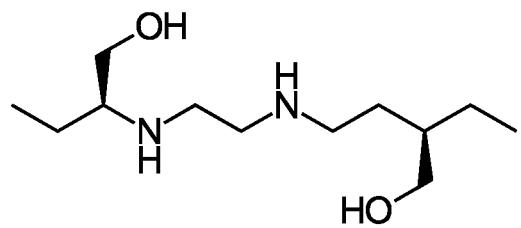
Figure 2:
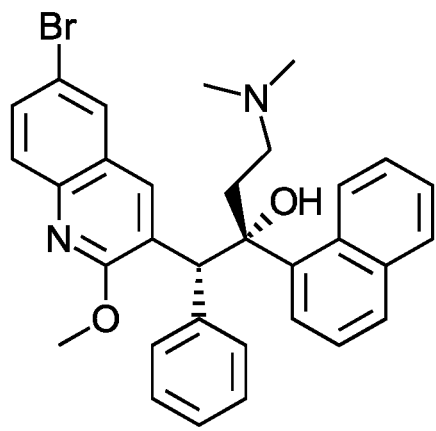
FIG. 2 shows the chemical structures of the drugs bedaquiline, ethionamide, delamanide and pretomanid.
Figure 2:
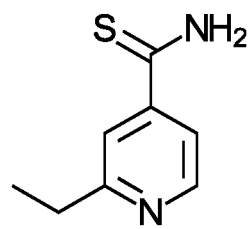
Figure 2:
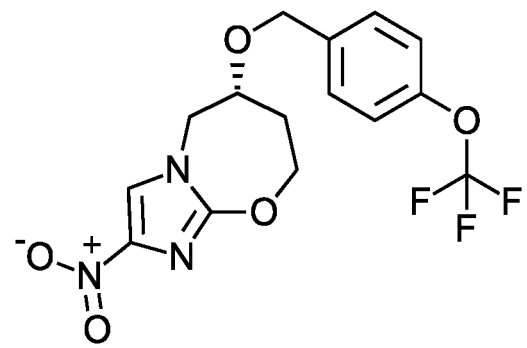
Figure 2:
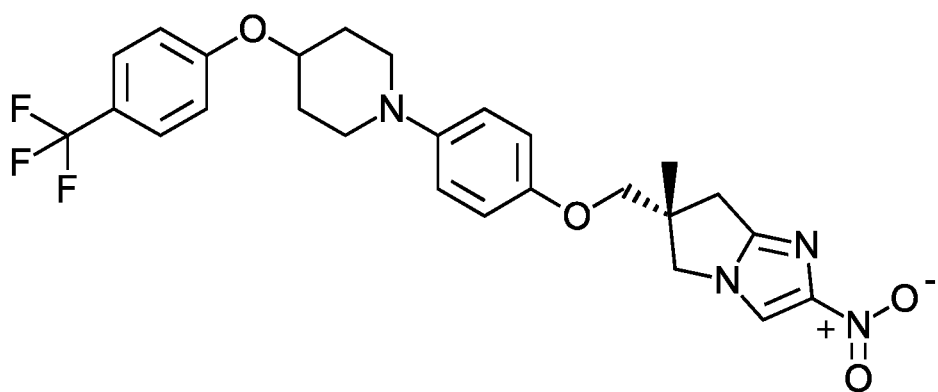
Figure 3A:
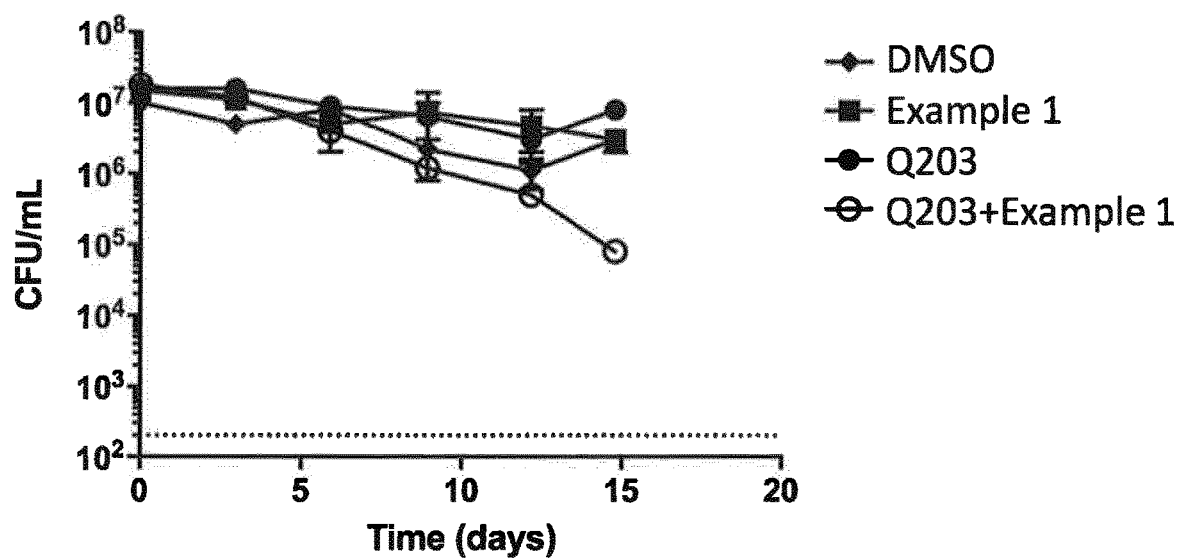
FIG. 3a shows a ratio of colony forming units of treated/untreated tuberculosis bacteria during 15 days upon addition of the compound of Example 1; Q203; and a combination of Q203 and the compound of Example 1, respectively.
Figure 3B:
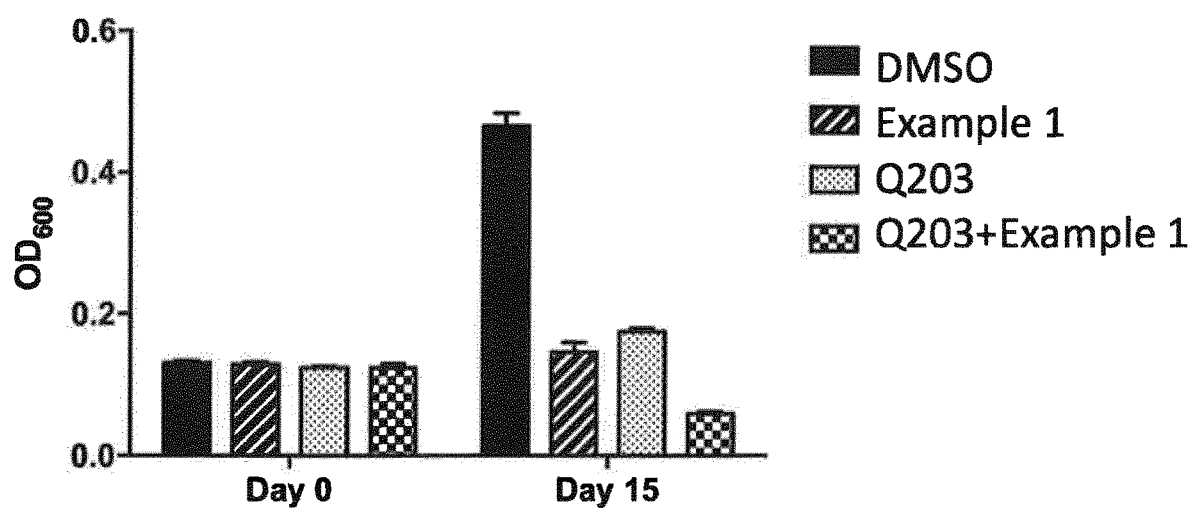
FIG. 3b shows the $OD_{600}$ of treated/untreated tuberculosis bacteria at day zero and day 15 upon addition of the compound of Example 1; Q203; and a combination of Q203 and the compound of Example 1, respectively.

The present disclosure provides a combination comprising:

(i) a drug against tuberculosis inhibiting the cytochrome b subunit of the bc1 complex, said cytochrome b subunit being encoded by the gene qcrB, in *Mycobacterium tuberculosis*, or a pharmaceutically acceptable salt thereof; and (ii) a compound of Formula II

II or a pharmaceutically acceptable salt thereof,
wherein
$R_1$ is selected from the group consisting of:
a) C(O)OH,
b) tetrazolyl,
c) $CH_2OH$,
d) $C(O)NR_{6a}R_{6b}$,
e) $C(O)NHSO_2R_7$,
f) $C(O)OR_8$,
g) $NH_2$,
h) H, i)

j)

k)

and
l) imidazole carboxylate,
$R_2$ is selected from the group consisting of:
a) H,
b) Cl, F, Br or I,
c) $CH_2OH$,
d) $C_1$-$C_4$alkyl, and
e) $NY_1Y_2$,
$R_3$ is selected from the group consisting of:
a) 1-naphtyl, 2-naphtyl or 1-naphtyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl
d) 2-(3-methyl)phenylmethylene,
e) benzothiophen-2-yl
f) H,
g) $C_1$-$C_4$alkyl,
h) 2-methyl-1-aza-2-bora-1H-naphth-5-yloxy,
i) 2-methyl-1-aza-2-bora-1H-naphth-5-yl,
j) isoxazol-5-yl optionally substituted with methyl, 1-naphthyl, 2-naphtyl, 1-anthryl, m-trifluoromethylphenyl, 3,5-ditrifluoromethylphenyl, 3,4-methylenedioxyphenyl, thiophene or phenyl,
k) isoxazol-3-yl substituted with m-trifluoromethylphenyl or 1-naphthyl, and
l) benzoxazole-2-yl, m)

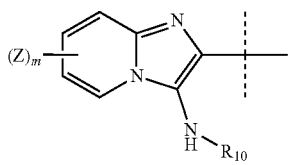

R$_4$ is selected from the group consisting of:
a) C$_1$-C$_4$alkyl substituted by 0, 1, 2, 3 or 4 fluoro;
b) C$_3$-C$_6$cycloalkyl,
c) C$_1$-C$_4$alkoxy substituted by 0, 1, 2, 3 or 4 fluoro,
d) C$_3$-C$_6$cycloalkoxy,
e) a 3-, 4-, 5- or 6-membered heterocycle, substituted with 0 or 1 substituent selected from the group consisting of phenyl and 1-naphthyl,
f) N-methyl 3-indolyl,
g) NR$_{9a}$R$_{9b}$, and
h) C$_2$-C$_4$alkynyl, R$_5$ is selected from the group consisting of:
a) H,
b) phenyl substituted with 0, 1, 2 or 3 methyl group(s),
c) benzyl,
d) thienyl,
e) C$_1$-C$_4$alkoxy, and
f) a 3-, 4-, 5- or 6-membered heterocycle, The following definitions shall apply throughout this document unless stated otherwise.

R$_{6a}$ is selected from the group consisting of H and C$_1$-C$_4$alkyl.

R$_{6b}$ is selected from the group consisting of H, C$_1$-C$_4$alkyl, C$_1$-C$_4$alkoxy and isonicotinoylamino.

R$_7$ is SO$_2$C$_1$-C$_4$alkyl or SO$_2$phenyl.

R$_8$ represents 2-{2-[1-(hydroxymethyl)propylamino]ethylamino}butyl).

R$_{9a}$ represents C$_1$-C$_4$alkyl.

R$_{9b}$ represents C$_1$-C$_4$alkyl.

R$_{10}$ represents H; C$_1$-C4alkyl substituted with 0, 1, 2 or 3 F; benzyl substituted with 0 or 1 trifluoromethyl; or naphtalen-1-yl-methylene, Y$_1$ and Y$_2$ each independently represents hydrogen, methyl, CH$_3$S(O)$_2$ or C(O)CH$_3$, or Y$_1$ and Y$_2$ together form CH$_2$CH$_2$CH$_2$CH$_2$ or CH$_2$CH$_2$CH$_2$CH$_2$CH$_2$.

X is S, SO or SO$_2$.

m is 0 or 1.

n is 0 or 1.

Z represents C$_1$-C$_4$alkyl substituted with 0, 1, 2 or 3 F; C$_1$-C$_4$alkoxy substituted with 0, 1, 2 or 3 F; or a halogen selected from Cl, F. Br or I.

The term "C$_1$-C$_4$alkyl" denotes a straight or branched, saturated or unsaturated alkyl group of one to four carbon atoms. Examples of "C$_1$-C$_4$alkyl" include, but are not limited to, methyl, ethyl, vinyl, allyl, n-propyl, isopropyl, n-butyl, sec-butyl.iso-butyl and tert-butyl.

The term C$_2$-C$_4$alkenyl denotes a straight or branched alkyne containing chain comprising at least one alkyne group. For instance, the "C$_2$-C$_4$alkenyl" may be ethynyl.

The term "C$_1$-C$_4$alkoxy" denotes a C$_1$-C$_4$alkyl group as described herein which is linked to an oxygen atom. Examples of "C$_1$-C$_4$alkoxy" include, but are not limited to, methoxy, ethoxy, n-propoxy, iso-propoxy and butoxy.

The term "C$_3$-C$_6$cycloalkyl" denotes a saturated or unsaturated non-aromatic monocyclic ring composed of three, four, five or six carbon atoms. Examples of "C$_3$-C$_6$cycloalkyl" include, but are not limited to, cyclopropyl, cyclobutyl, cyclopentyl and cyclohexyl.

The term "C$_3$-C$_6$cycloalkoxy" denotes a saturated or unsaturated non-aromatic monocyclic ring composed of three, four, five or six carbon atoms which is linked to an oxygen atom. Examples of "C$_3$-C$_6$cycloalkoxy" include, but are not limited to, cyclopropyloxy, cyclopropxymethylene, cyclobutyloxy, cyclobutyloxymethylene, cyclopentyloxy, cyclopentyloxymethylene, cyclohexyloxy and cyclohexyloxymethylene.

The term "3-membered heterocycle" denotes a 3-membered saturated or unsaturated heterocycle. Examples of a 3-membered saturated heterocycle include, but are not limited to, aziridine, oxirane and thiirane. Examples of 3-membered unsaturated heterocycles include, but are not limited to, azirine, oxirene and thiirene.

The term "4-membered heterocycle" denotes a 4-membered saturated or unsaturated heterocycle. Examples of a 4-membered heterocycle include, but are not limited to, azetidine, oxethane and thietane.

The term "5-membered heterocycle" denotes a 5-membered saturated or unsaturated heterocycle. Examples of a 5-membered heterocycles include, but are not limited to, pyrrolidine, tetrahydrofurane, thiolane, pyrrole, furane, thiophene, imidazolidine, pyrazolidine, pxazolidine, isoxazolidine, thiazolidine, isothiazolidine, dioxolane, dithiolane, imidazole, pyrazole, oxazole, isoxazole, thiazole, and isothiazole The term "6-membered heterocycle" denotes a 6-membered saturated or unsaturated heterocycle. Examples of a 6-membered heterocycles include, but are not limited to piperidine, pyridine, piperazine, morpholine, and thiomorpholine.

The drug against tuberculosis as described herein is to be understood as a drug that counteracts tuberculosis bacteria. The drug against tuberculosis as described herein may reduce, substantially eliminate or eradicate tuberculosis bacteria. The drug against tuberculosis as described herein may also be denominated an anti-tuberculosis drug or a drug to treat tuberculosis. More specifically, the drug against tuberculosis as described herein acts by inhibiting the cytochrome b subunit of the bc1 complex, said cytochrome b subunit being encoded by the gene qcrB, in *Mycobacterium tuberculosis*, In this document, the complex mentioned in the expression "the cytochrome b subunit of the bc1 complex said cytochrome b subunit being encoded by the gene qcrB in *Mycobacterium tuberculosis*" is a multi-protein complex comprised of QcrB, QcrA, QcrC.

Examples of drugs against tuberculosis that may be used in combination with the compounds of Formula II as described herein include first line anti-tuberculous drugs, second line anti-tuberculous drugs and/or third line anti-tuberculous drugs.

First line anti-tuberculous drugs may be one or more of the following: 6-chloro-2-ethyl-N-[(4-{4-[4-(trifluoromethoxy)phenyl]piperidin-1-yl}phenyl)methyl]imidazo[1,2-a]pyridine-3-carboxamide (Q203), isoniazid, ethambuthol, pyrazinamide, rifampicin, streptomycin. For instance, the drug against tuberculosis may be one or more of the following: 6-chloro-2-ethyl-N-[(4-{4-[4-(trifluoromethoxy)phenyl]piperid in-1-yl}pheynyl)methyl]imidazo[1,2-a]pyridine-3-carboxamide (Q203), isoniazid, ethambuthol, pyrazinamide, rifampicin. In an example, the drug against tuberculosis may be 6-chloro-2-ethyl-N-[(4-{4-[4-(trifluoromethoxy)phenyl]piperidin-1-yl}pheynyl)methyl]

imidazo[1,2-a]pyridine-3-carboxamide (Q203), isoniazid optionally in combination with one or more of ethambuthol, pyrazinamide, rifampicin.

Second line anti-tuberculosis drugs may be one or more of the following:
aminoglycosides, such as amikacin or kanamycin,
polypeptides such as capreomycin, viomycin, enviomycin,
fluoroquinolones such as ciprofloxacin (CIP), levofloxacin, moxifloxacin (MXF);
thioamides such as ethionamide, prothionamide,
cycloserine,
terizidone,
6-chloro-2-ethyl-N-[(4-{4-[4-(trifluoromethoxy)phenyl]piperidin-1-yl}phenyl)methyl]imidazo[1,2-a]pyridine-3-carboxamide (Q203)Third line anti-tuberculosis drugs may be one or more the following:
rifabutin,
macrolides such as chlaritromycin (CLLR),
linezolid (LZD),
thioridazine;
arginine,
vitamin D,
bedaquiline,
pretomanid,
delamanid,
6-chloro-2-ethyl-N-[(4-{4-[4-(trifluoromethoxy)phenyl]piperidin-1-yl}phenyl)methyl]imidazo[1,2-a]pyridine-3-carboxamide (Q203).

Examples of drugs against tuberculosis that may be used in combination with the compounds of Formula II as described herein include 6-chloro-2-ethyl-N-[(4-{4-[4-(trifluoromethoxy)phenyl]piperidin-1-yl}pheynyl)methyl]imidazo[1,2-a]pyridine-3-carboxamide (Q203), isoniazid, pyrazinamide, pretomanid, delamanid, bedaquiline, streptomycin, levofloxacin, moxifloxacin and ofloxacin, cycloserine, terizidone, thionamide. protionamide and-4-aminosalicylic acid. For instance, the drug against tuberculosis may be 6-chloro-2-ethyl-N-[(4-{, 4-[4-(trifluoromethoxy)phenyl]piperidin-1-yl}phenyl)methyl]imidazo[1,2-a]pyridine-3-carboxamide (Q203), isoniazid and/or 4-aminosalicylic acid. In a further example, the drug against tuberculosis may be 6-chloro-2-ethyl-N-[(4-{4-[4-(trifluoromethoxy)phenyl]piperidin-1-yl}pheynyl)methyl]imidazo[1,2-a]pyridine-3-carboxamide (Q203), isoniazide and/or bedaquiline, optionally in combination with one or more of ethambutol, pyrazinamide, rifampicin.

In addition or as an alternative to the compounds of Formula II described herein, the compounds described in WO 2014/185853 and/or PCT/EP2015/076578 are provided and incorporated by reference. These compounds may be used in combination with the drug against tuberculosis described herein and/or in the treatment and/or prevention of tuberculosis.

There is also provided a combination as described herein in which:
$R_1$ is selected from the group consisting of:
a) C(O)OH,
b) tetrazolyl,
c) CH$_2$OH,
d) C(O)NR$_{6a}$R$_{6b}$,
e) C(O)NHSO$_2$R$_7$,
f) C(O)OR$_8$,
g) NH$_2$,
h) H, i)
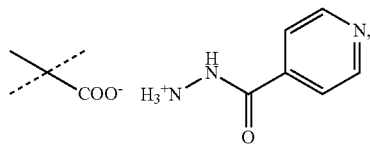

j)
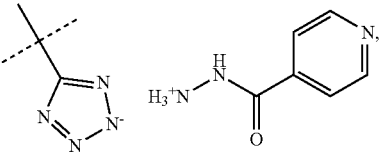

and
k)
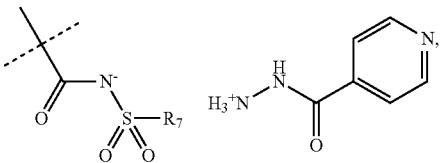

$R_3$ is selected from the group consisting of:
a) 1-naphtyl, 2-naphtyl or 1-naphtyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl
d) 2-(3-methyl)phenylmethylene,
e) benzothiophen-2-yl
f) H,
g) C$_1$-C$_4$-alkyl,
i) 2-methyl-1-aza-2-bora-1H-naphth-5-yloxy, and
j) 2-methyl-1-aza-2-bora-1H-naphth-5-yl,
$R_4$ is selected from the group consisting of:
a) C$_1$-C$_4$alkyl substituted by 0, 1, 2, 3 or 4 fluoro;
b) C$_3$-C$_6$cycloalkyl,
c) C$_1$-C$_4$alkoxy substituted by 0, 1, 2, 3 or 4 fluoro,
d) C$_3$-C$_6$cycloalkoxy,
e) a 3-, 4-, 5- or 6-membered heterocycle,
f) N-methyl 3-indolyl, and
g) NR$_{9a}$R$_{9b}$,
$R_5$ is as defined in claim 1,
and in the above definitions:
$R_{6a}$ is selected from the group consisting of H and C$_1$-C$_4$alkyl,
$R_{6b}$ is selected from the group consisting of H, C$_1$-C$_4$alkyl, C$_1$-C$_4$alkoxy and isonicotinoylamino;
$R_7$ is C$_1$-C$_4$alkyl or phenyl,
$R_8$ represents 2-{2-[1-(hydroxymethyl)propylamino]ethylamino}butyl),
$R_{9a}$ represents C$_1$-C$_4$alkyl, $R_{9b}$ represents $C_1$-$C_4$alkyl, $Y_1$ and $Y_2$ each independently represents hydrogen, methyl, $CH_3S(O)_2$ or $C(O)CH_3$, or $Y_1$ and $Y_2$ together form $CH_2CH_2CH_2CH_2$ or $CH_2CH_2CH_2CH_2CH_2$, n is 0, and X is S, SO or $SO_2$.

The compound of Formula II may exist as Formula IIa or Formula IIb, wherein $R_1$, $R_2$, $R_3$, $R_4$, $R_5$, n and X may have the values described herein.

Formula IIa

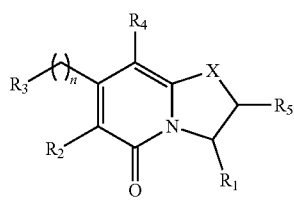

Formula IIb

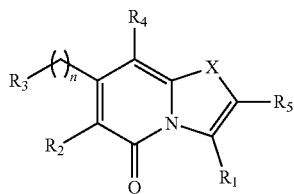

Further, the compound of Formula IIa may exist as cis stereoisomers or as trans stereoisomers.

When $R_5$ is hydrogen the compound of Formula IIa may be the enantiomer of Formula IIa51, wherein, $R_1$, $R_2$, $R_3$, $R_4$, n and X may have values described herein.

Formula IIa51

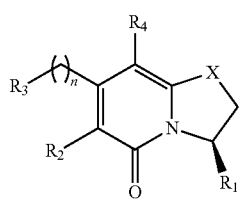

As described herein, X may be S, SO or $SO_2$ for the compounds of the present disclosure. Accordingly, when X is S the bicyclic ring structure contains a sulfide. When X is SO the bicyclic ring structure contains a sulphoxide. When X is $SO_2$ the bicyclic ring structure contains a sulphone.

When $R_1$ is an acidic group AH such as C(O)OH, tetrazole or $C(O)NHSO_2R_7$ the compound of Formula II may form a salt with an antituberculosis drug such as Q203 as described herein or isoniazide thereby providing a salt of Formula IIIa or Formula IIIb. For these compounds, $A^-$, $R_2$, $R_3$, $R_4$, $R_5$, $R_7$, n and X may have values as described herein. It will be appreciated that the isoniazide of Formulas IIIa or Formula IIIb may be replaced with another drug against tuberculosis such as Q203 or bedaquiline.

Formula IIIa

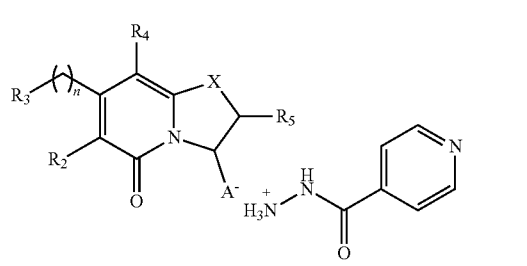

Formula IIIb

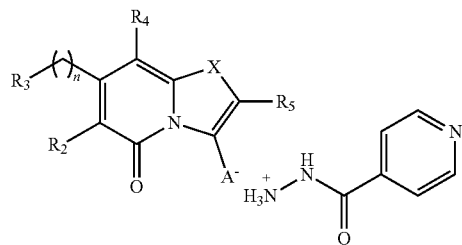

Further, the present disclosure provides a compound of Formula IV, or a pharmaceutically acceptable salt thereof. $R_2$, $R_3$, $R_4$, $R_5$, n and X may have values as described herein. The compound of Formula IV may be provided by reacting isoniazide with a compound of Formula II, wherein $R_1$ is C(O)OH, of the present disclosure. In this reaction, $R_1$ may be transformed from C(O)OH into C(O)Cl prior to reaction with the compound of Formula IV. The compound of Formula IV may be provided in combination with isoniazid. Alternatively, it may be used as such in, optionally in combination with a pharmaceutical excipient, diluent and/or carrier.

Formula IV

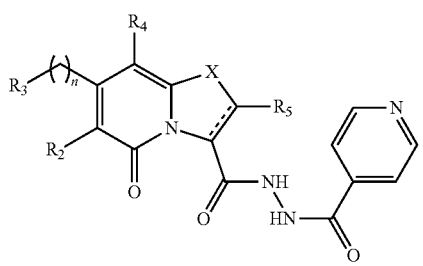

The compound of Formula IV may exist as a compound of Formula IVa or as a compound of Formula IVb. $R_2$, $R_3$, $R_4$, $R_5$, n and X may have values as described herein. For instance, $R_5$ may be hydrogen and X may be S, SO or $SO_2$.

Formula IVa

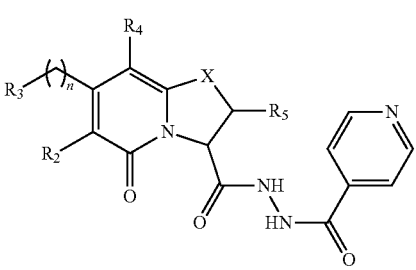

-continued

Formula IVb

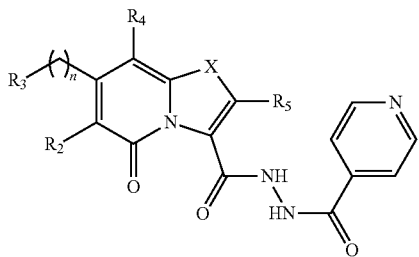

The compound of Formula IVa may exist as cis and trans stereoisomers. The present disclosure encompasses all these stereoisomers. For instance, the present disclosure provides a compound of Formula IVa5:

Formula IVa5

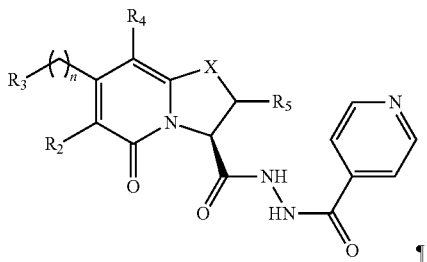

wherein $R_2$, $R_3$, $R_4$, $R_5$, n and X are as described herein, or a pharmaceutically acceptable salt thereof.

As an example of a compound of Formula IVa the present disclosure provides {7-cyclopropyl-6-[(1-naphthyl)methyl]-4-oxo-1-thia-3a-aza-3-indanyl}(2-isonicotinoylhydrazino)formaldehyde.

Further values of wherein $R_1$, $R_2$, $R_3$, $R_4$, $R_5$, n and X will now follow. It will be appreciated that these values may be applied to any compound of Formula II of the present disclosure.

X may be S or SO. For instance, X may be S. In a further example, X may be SO. In still a further example, X may be $SO_2$.

$R_1$ may be C(O)OH or tetrazolyl. For instance, $R_1$ may be C(O)OH.

$R_2$ may be H.

$R_3$ may be selected from the group consisting of:
a) 1-naphtyl, 2-naphtyl or 1-naphtyloxy, each independently substituted with 0, 1, 2 or 3 substituents selected from the group consisting of methyl, fluoro, chloro, cyano and methoxy, and
b) phenyl substituted with 0, 1, 2 or 3 substituents independently selected from the group consisting of methyl, fluoro, chloro, cyano and trifluoromethyl.

Further, $R_3$ may be selected from selected from the group consisting of:
1-naphtyl, 2-naphtyl, 4-methyl-1-naphtyl, 4-fluoro-1-naphtyl, 4-bromo-1-naphtyl, 4-methoxy-1-naphtyl, 2-methoxy-1-naphtyl, 2-methoxy-1-naphtyl, 1-naphtyloxy, 3-methylphenyl, 2,3-dimethylphenyl, 2-fluoro-5-methylphenyl, 2,3-dichlorophenyl, 2-(3-methyl)phenylmethylene; 2,3-xylylamine, 3-trifluoromethylphenyl and benzothiophene-2-yl. For instance, $R_3$ may be 1-naphtyl.

$R_4$ may be $C_2$-$C_6$cycloalkyl. For instance, $R_4$ may be cyclopropyl.

$R_5$ may be H.

n may be 0 or 1.

The combination described herein may comprise a compound of Formula II selected from one or more of:
(3R)-7-Cyclopropyl-6-[(1-naphthyl)methyl]-4-oxo-1-thia-3a-aza-3-indancarboxylic acid,
(3R)-7-Cyclopropyl-4-oxo-6-{(7-thiabicyclo[4.3.0]nona-1,3,5,8-tetraen-8-yl)methyl}-1-thia-3a-aza-3-indancarboxylic acid,
(3R)-7-Cyclopropyl-6-[(4-fluoro-1-naphthyl)methyl]-4-oxo-1-thia-3a-aza-3-indancarboxylic acid,
(3R)-7-Cyclopropyl-6-[(4-methyl-1-naphthyl)methyl]-4-oxo-1-thia-3a-aza-3-indancarboxylic acid,
(3S)-7-Cyclopropyl-6-[(1-naphthyl)methyl]-4-oxo-1-thia-3a-aza-3-indancarboxylic acid,
5-Cyclopropyl-4-[(1-naphthyl)methyl]-2-oxo-8-(3-thienyl)-7-thia-1-azabicyclo[4.3.0]nona-3,5,8-triene-9-carboxylic acid,
(3R)-7-Cyclopropyl-6-[(1-naphthyloxy)methyl]-4-oxo-1-thia-3a-aza-3-indancarboxylic acid,
(3R)-7-Cyclopropyl-6-[(2-fluoro-5-methyl-phenyl)methyl]-4-oxo-1-thia-3a-aza-3-indancarboxylic acid,
(3R)-7-Cyclopropyl-4-oxo-6-[(2,3-xylyl)methyl]-1-thia-3a-aza-3-indancarboxylic acid,
(3R)-7-Methyl-6-[(1-naphthyl)methyl]-4-oxo-1-thia-3a-aza-3-indancarboxylic acid,
(N-Methylmethoxyamino){(3R)-7-cyclopropyl-6-[(1-naphthyl)methyl]-4-oxo-1-thia-3a-aza-3-indanyl}formaldehyde,
(3R)-7-Cyclopropyl-6-[(1-naphthyl)methyl]-3-(1H-1,2,3,4-tetrazol-5-yl)-1-thia-3a-aza-4-indanone,
5-Cyclopropyl-4-[(1-naphthyl)methyl]-2-oxo-8-phenyl-7-thia-1-azabicyclo[4.3.0]nona-3,5,8-triene-9-carboxylic acid,
5-Cyclopropyl-4-[(1-naphthyl)methyl]-2-oxo-8-(m-tolyl)-7-thia-1-azabicyclo[4.3.0]nona-3,5,8-triene-9-carboxylic acid,
(3R)-7-Cyclopropyl-6-[(2-naphthyl)methyl]-4-oxo-1-thia-3a-aza-3-indancarboxylic acid,
(3R)-7-Cyclopropyl-3-(hydroxymethyl)-6-[(1-naphthyl)methyl]-1-thia-3a-aza-4-indanone,
(3R)-6-[(1-Naphthyl)methyl]-4-oxo-7-(2-thienyl)-1-thia-3a-aza-3-indancarboxylic acid,
5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid,
8-Benzyl-5-cyclopropyl-4-[(1-naphthyl)methyl]-2-oxo-7-thia-1-azabicyclo[4.3.0]nona-3,5,8-triene-9-carboxylic acid,
(3R)-7-Cyclopropyl-6-[(2,3-dichlorophenyl)methyl]-4-oxo-1-thia-3a-aza-3-indancarboxylic acid,
(3R)-7-Cyclopropyl-6-[(1-naphthyl)methyl]-4-oxo-1-thia-3a-aza-3-indancarboxamide,
{(3R)-7-Cyclopropyl-6-[(1-naphthyl)methyl]-4-oxo-1-thia-3a-aza-3-indanyl}(phenylsulfonylamino)formaldehyde,
(3R)-7-Isopropyl-6-[(1-naphthyl)methyl]-4-oxo-1-thia-3a-aza-3-indancarboxylic acid,
(3R)-7-Cyclopropyl-6-methyl-4-oxo-1-thia-3a-aza-3-indancarboxylic acid,
(3R)-6-[(p-Chlorophenyl)methyl]-7-cyclopropyl-4-oxo-1-thia-3a-aza-3-indancarboxylic acid,
{(3R)-7-Cyclopropyl-6-[(1-naphthyl)methyl]-4-oxo-1-thia-3a-aza-3-indanyl}(methylsulfonylamino)formaldehyde,
(3R)-7-Cyclopropyl-4-oxo-6-[(m-tolyl)methyl]-1-thia-3a-aza-3-indancarboxylic acid, (3R)-7-Isopropyl-4-oxo-6-[2-(m-tolyl)ethyl]-1-thia-3a-aza-3-indancarboxylic acid,
7-(1-Methyl-1H-indol-3-yl)-6-[(1-naphthyloxy)methyl]-4-oxo-1-thia-3a-aza-3-indancarboxylic acid,
(3R)-6-[(4-Bromo-1-naphthyl)methyl]-7-cyclopropyl-4-oxo-1-thia-3a-aza-3-indancarboxylic acid,
7-Cyclopropyl-6-[(1-naphthyl)methyl]-1-thia-3a-aza-4-indanone,
(3R)-7-Cyclopropyl-5-(hydroxymethyl)-6-[(1-naphthyl)methyl]-4-oxo-1-thia-3a-aza-3-indancarboxylic acid,
(3S)-3-Amino-7-cyclopropyl-6-[(1-naphthyl)methyl]-1-thia-3a-aza-4-indanone,
(2R,3R)-7-Cyclopropyl-6-[(1-naphthyl)methyl]-4-oxo-2-phenyl-1-thia-3a-aza-3-indancarboxylic acid,
(2S,3R)-7-Cyclopropyl-2-methoxy-6-[(1-naphthyl)methyl]-4-oxo-1-thia-3a-aza-3-indancarboxylic acid,
7-Cyclopropyl-4-oxo-6-{[m-(trifluoromethyl)phenyl]methyl}-1-thia-3a-aza-3-indancarboxylic acid,
2-{2-[1-(Hydroxymethyl)propylamino]ethylamino}butyl 7-cyclopropyl-6-[(1-naphthyl)methyl]-4-oxo-1-thia-3a-aza-3-indancarboxylate,
{7-Cyclopropyl-6-[(1-naphthyl)methyl]-4-oxo-1-thia-3a-aza-3-indanyl}(2-isonicotinoylhydrazino)formaldehyde,
7-Cyclopropyl-6-[(4-methoxy-1-naphthyl)methyl]-4-oxo-1-thia-3a-aza-3-indancarboxylic acid,
(3R)-7-(Dimethylamino)-6-[(1-naphthyl)methyl]-4-oxo-1-thia-3a-aza-3-indancarboxylic acid,
(3R)-5-Bromo-7-cyclopropyl-6-[(1-naphthyl)methyl]-4-oxo-1-thia-3a-aza-3-indancarboxylic acid,
7-Cyclopropyl-6-[(1-naphthyl)methyl]-1,1-dioxo-4-oxo-1-thia-3a-aza-3-indancarboxylic acid,
(3R)-7-Cyclopropyl-4-oxo-6-[(2,3-xylidino)methyl]-1-thia-3a-aza-3-indancarboxylic acid,
7-Cyclopropyl-6-[(1-naphthyl)methyl]-1-oxo-4-oxo-1-thia-3a-aza-3-indancarboxylic acid,
(3R)-7-Ethoxy-6-[(1-naphthyl)methyl]-4-oxo-1-thia-3a-aza-3-indancarboxylic acid,
(3R)-6-[(1-Naphthyl)methyl]-4-oxo-7-(trifluoromethyl)-1-thia-3a-aza-3-indancarboxylic acid,
(3R)-7-Isobutoxy-6-[(1-naphthyl)methyl]-4-oxo-1-thia-3a-aza-3-indancarboxylic acid,
(3R)-7-Cyclopropyl-6-[(2-methoxy-1-naphthyl)methyl]-4-oxo-1-thia-3a-aza-3-indancarboxylic acid,
(3R)-7-(Cyclopropylmethoxy)-6-[(1-naphthyl)methyl]-4-oxo-1-thia-3a-aza-3-indancarboxylic acid,
7-Cyclopropyl-6-[(2-methyl-1-aza-2-bora-1H-naphth-5-yl)methyl]-4-oxo-1-thia-3a-aza-3-indancarboxylic acid,
7-Cyclopropyl-6-[(2-methyl-1-aza-2-bora-1H-naphth-5-yloxy)methyl]-4-oxo-1-thia-3a-aza-3-indancarboxylic acid,
7-Cyclopropyl-6-[(2-methyl-1-aza-2-bora-1H-naphth-8-yl)methyl]-4-oxo-1-thia-3a-aza-3-indancarboxylic acid,
7-Cyclopropyl-6-[(2-methyl-1-aza-2-bora-1H-naphth-8-yloxy)methyl]-4-oxo-1-thia-3a-aza-3-indancarboxylic acid,
1H-imidazol-1-ium 7-(benzo[d]oxazol-2-yl)-8-cyclopropyl-5-oxo-3,5-dihydro-2H-thiazolo[3,2-a]pyridine-3-carboxylate,
1H-imidazol-1-ium 8-cyclopropyl-7-(3-(naphthalen-1-yl)isoxazol-5-yl)-5-oxo-3,5-dihydro-2H-thiazolo[3,2-a]pyridine-3-carboxylate,
1H-imidazol-1-ium 8-cyclopropyl-5-oxo-7-(3-(3-(trifluoromethyl)phenyl)isoxazol-5-yl)-3,5-dihydro-2H-thiazolo[3,2-a]pyridine-3-carboxylate,
1H-imidazol-1-ium 8-cyclopropyl-5-oxo-7-(3-(thiophen-2-yl)isoxazol-5-yl)-3,5-dihydro-2H-thiazolo[3,2-a]pyridine-3-carboxylate,
1H-imidazol-1-ium 8-cyclopropyl-5-oxo-7-(3-phenylisoxazol-5-yl)-3,5-dihydro-2H-thiazolo[3,2-a]pyridine-3-carboxylate,
1H-imidazol-1-ium 6-bromo-7-(naphthalen-1-ylmethyl)-5-oxo-8-(3-phenylisoxazol-5-yl)-3,5-dihydro-2H-thiazolo[3,2-a]pyridine-3-carboxylate,
1H-imidazol-1-ium 7-(naphthalen-1-ylmethyl)-5-oxo-8-(3-phenyl-4,5-dihydroisoxazol-5-yl)-3,5-dihydro-2H-thiazolo[3,2-a]pyridine-3-carboxylate,
1H-imidazol-1-ium 8-ethynyl-7-(naphthalen-1-ylmethyl)-5-oxo-3,5-dihydro-2H-thiazolo[3,2-a]pyridine-3-carboxylate,
1H-imidazol-1-ium 7-(naphthalen-1-ylmethyl)-5-oxo-8-(3-phenylisoxazol-5-yl)-3,5-dihydro-2H-thiazolo[3,2-a]pyridine-3-carboxylate,
1H-imidazol-1-ium 8-(3-(naphthalen-1-yl)isoxazol-5-yl)-7-(naphthalen-1-ylmethyl)-5-oxo-3,5-dihydro-2H-thiazolo[3,2-a]pyridine-3-carboxylate,
1H-imidazol-1-ium 8-cyclopropyl-7-(naphthalen-1-ylmethyl)-5-oxo-3,5-dihydro-2H-thiazolo[3,2-a]pyridine-3-carboxylate,
8-cyclopropyl-5-oxo-7-(5-(3-(trifluoromethyl)phenyl)isoxazol-3-yl)-2,3-dihydrothiazolo[3,2-a]pyridine-3-carboxylic acid,
8-cyclopropyl-7-(5-(naphthalen-1-yl)isoxazol-3-yl)-5-oxo-2,3-dihydrothiazolo[3,2-a]pyridine-3-carboxylic acid,
8-cyclopropyl-7-(3-(naphthalen-2-yl)isoxazol-5-yl)-5-oxo-2,3-dihydrothiazolo[3,2-a]pyridine-3-carboxylic acid,
1H-imidazol-1-ium 7-(3-(benzo[d][1,3]dioxol-5-yl)isoxazol-5-yl)-8-cyclopropyl-5-oxo-2,3-dihydrothiazolo[3,2-a]pyridine-3-carboxylate,
1H-imidazol-1-ium 7-(3-(anthracen-9-yl)isoxazol-5-yl)-8-cyclopropyl-5-oxo-2,3-dihydrothiazolo[3,2-a]pyridine-3-carboxylate,
7-(3-(3,5-bis(trifluoromethyl)phenyl)isoxazol-5-yl)-8-cyclopropyl-5-oxo-2,3-dihydrothiazolo[3,2-a]pyridine-3-carboxylic acid, or
8-cyclopropyl-7-(3-methylisoxazol-5-yl)-5-oxo-2,3-dihydrothiazolo[3,2-a]pyridine-3-carboxylic acid;
7-(3-(tert-butylamino)imidazo[1,2-a]pyridin-2-yl)-8-cyclopropyl-5-oxo-2,3-dihydrothiazolo[3,2-a]pyridine-3-carboxylic acid,
7-(3-(benzylamino)imidazo[1,2-a]pyridin-2-yl)-8-cyclopropyl-5-oxo-2,3-dihydrothiazolo[3,2-a]pyridine-3-carboxylic acid,
8-cyclopropyl-7-(3-((naphthalen-1-ylmethyl)amino)imidazo[1,2-a]pyridin-2-yl)-5-oxo-2,3-dihydrothiazolo[3,2-a]pyridine-3-carboxylic acid,
8-cyclopropyl-5-oxo-7-(3-((3-(trifluoromethyl)benzyl)amino)imidazo[1,2-a]pyridin-2-yl)-2,3-dihydrothiazolo[3,2-a]pyridine-3-carboxylic acid,
7-(3-(tert-butylamino)-6-chloroimidazo[1,2-a]pyridin-2-yl)-8-cyclopropyl-5-oxo-2,3-dihydrothiazolo[3,2-a]pyridine-3-carboxylic acid,
7-(6-chloro-3-((naphthalen-1-ylmethyl)amino)imidazo[1,2-a]pyridin-2-yl)-8-cyclopropyl-5-oxo-2,3-dihydrothiazolo[3,2-a]pyridine-3-carboxylic acid,
7-(3-(benzylamino)-6-chloroimidazo[1,2-a]pyridin-2-yl)-8-cyclopropyl-5-oxo-2,3-dihydrothiazolo[3,2-a]pyridine-3-carboxylic acid,
7-(6-chloro-3-((3-(trifluoromethyl)benzyl)amino)imidazo[1,2-a]pyridin-2-yl)-8-cyclopropyl-5-oxo-2,3-dihydrothiazolo[3,2-a]pyridine-3-carboxylic acid,
7-(3-(tert-butylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-7-(3-((naphthalen-1-ylmethyl)amino)-7-(trifluoromethyl)imidazo[1,2-a]pyridin-2-yl)-5-oxo-2,3-dihydrothiazolo[3,2-a]pyridine-3-carboxylic acid, 7-(3-(benzylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-5-oxo-7-(7-(trifluoromethyl)-3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((naphthalen-1-ylmethyl)amino)imidazo[1,2-a]pyridin-2-yl)-5-oxo-2,3-dihydrothiazolo[3,2-a]pyridine-3-carboxylic acid, 7-(3-(benzylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((3-(trifluoromethyl)benzyl)amino)imidazo[1,2-a]pyridin-2-yl)-5-oxo-2,3-dihydrothiazolo[3,2-a]pyridine-3-carboxylic acid, or a pharmaceutically acceptable salt of any one of the foregoing compounds.

Thus, the present disclosure provides a combination as described herein wherein the compound of Formula II is as defined in any one of Examples 1-88.

In a further example, the combination described herein may comprise a compound of Formula II selected from one or more of:

(3R)-7-Cyclopropyl-6-[(1-naphthyl)methyl]-4-oxo-1-thia-3a-aza-3-indancarboxylic acid, (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid, (3R)-7-Cyclopropyl-6-[(4-fluoro-1-naphthyl)methyl]-4-oxo-1-thia-3a-aza-3-indancarboxylic acid, (3R)-7-Cyclopropyl-6-[(4-methyl-1-naphthyl)methyl]-4-oxo-1-thia-3a-aza-3-indancarboxylic acid, (3S)-7-Cyclopropyl-6-[(1-naphthyl)methyl]-4-oxo-1-thia-3a-aza-3-indancarboxylic acid, 5-Cyclopropyl-4-[(1-naphthyl)methyl]-2-oxo-8-(3-thienyl)-7-thia-1-azabicyclo[4.3.0]nona-3,5,8-triene-9-carboxylic acid, (3R)-7-Cyclopropyl-6-[(1-naphthyloxy)methyl]-4-oxo-1-thia-3a-aza-3-indancarboxylic acid, (3R)-7-Cyclopropyl-6-[(2-fluoro-5-methyl-phenyl)methyl]-4-oxo-1-thia-3a-aza-3-indancarboxylic acid, (3R)-7-Cyclopropyl-4-oxo-6-[(2,3-xylyl)methyl]-1-thia-3a-aza-3-indancarboxylic acid, (3R)-7-Methyl-6-[(1-naphthyl)methyl]-4-oxo-1-thia-3a-aza-3-indancarboxylic acid, (N-Methylmethoxyamino){(3R)-7-cyclopropyl-6-[(1-naphthyl)methyl]-4-oxo-1-thia-3a-aza-3-indanyl}formaldehyde, (3R)-7-Cyclopropyl-6-[(1-naphthyl)methyl]-3-(1H-1,2,3,4-tetrazol-5-yl)-1-thia-3a-aza-4-indanone, 5-Cyclopropyl-4-[(1-naphthyl)methyl]-2-oxo-8-phenyl-7-thia-1-azabicyclo[4.3.0]nona-3,5,8-triene-9-carboxylic acid, 5-Cyclopropyl-4-[(1-naphthyl)methyl]-2-oxo-8-(m-tolyl)-7-thia-1-azabicyclo[4.3.0]nona-3,5,8-triene-9-carboxylic acid, (3R)-7-Cyclopropyl-6-[(2-naphthyl)methyl]-4-oxo-1-thia-3a-aza-3-indancarboxylic acid, (3R)-7-Cyclopropyl-3-(hydroxymethyl)-6-[(1-naphthyl)methyl]-1-thia-3a-aza-4-indanone, (3R)-6-[(1-Naphthyl)methyl]-4-oxo-7-(2-thienyl)-1-thia-3a-aza-3-indancarboxylic acid, 5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid, 8-Benzyl-5-cyclopropyl-1-[(1-naphthyl)methyl]-2-oxo-7-thia-1-azabicyclo[4.3.0]nona-3,5,8-triene-9-carboxylic acid, (3R)-7-Cyclopropyl-6-[(2,3-dichlorophenyl)methyl]-4-oxo-1-thia-3a-aza-3-indancarboxylic acid, (3R)-7-Cyclopropyl-6-[(1-naphthyl)methyl]-4-oxo-1-thia-3a-aza-3-indancarboxamide, {(3R)-7-Cyclopropyl-6-[(1-naphthyl)methyl]-4-oxo-1-thia-3a-aza-3-indanyl}(phenylsulfonylamino)formaldehyde, (3R)-7-Isopropyl-6-[(1-naphthyl)methyl]-4-oxo-1-thia-3a-aza-3-indancarboxylic acid, (3R)-7-Cyclopropyl-6-methyl-4-oxo-1-thia-3a-aza-3-indancarboxylic acid, (3R)-6-[(p-Chlorophenyl)methyl]-7-cyclopropyl-4-oxo-1-thia-3a-aza-3-indancarboxylic acid, {(3R)-7-Cyclopropyl-6-[(1-naphthyl)methyl]-4-oxo-1-thia-3a-aza-3-indanyl}(methylsulfonylamino)formaldehyde, (3R)-7-Cyclopropyl-4-oxo-6-[(m-tolyl)methyl]-1-thia-3a-aza-3-indancarboxylic acid, (3R)-7-Isopropyl-4-oxo-6-[2-(m-tolyl)ethyl]-1-thia-3a-aza-3-indancarboxylic acid, 7-(1-Methyl-1H-indol-3-yl)-6-[(1-naphthyloxy)methyl]-4-oxo-1-thia-3a-aza-3-indancarboxylic acid, (3R)-6-[(4-Bromo-1-naphthyl)methyl]-7-cyclopropyl-4-oxo-1-thia-3a-aza-3-indancarboxylic acid, 7-Cyclopropyl-6-[(1-naphthyl)methyl]-1-thia-3a-aza-4-indanone, (3R)-7-Cyclopropyl-5-(hydroxymethyl)-6-[(1-naphthyl)methyl]-4-oxo-1-thia-3a-aza-3-indancarboxylic acid, (3S)-3-Amino-7-cyclopropyl-6-[(1-naphthyl)methyl]-1-thia-3a-aza-4-indanone, (2R,3R)-7-Cyclopropyl-6-[(1-naphthyl)methyl]-4-oxo-2-phenyl-1-thia-3a-aza-3-indancarboxylic acid, (2S,3R)-7-Cyclopropyl-2-methoxy-6-[(1-naphthyl)methyl]-4-oxo-1-thia-3a-aza-3-indancarboxylic acid, 7-Cyclopropyl-4-oxo-6-{[m-(trifluoromethyl)phenyl]methyl}-1-thia-3a-aza-3-indancarboxylic acid, 2-{2-[1-(Hydroxymethyl)propylamino]ethylamino}butyl 7-cyclopropyl-6-[(1-naphthyl)methyl]-4-oxo-1-thia-3a-aza-3-indancarboxylate, {7-Cyclopropyl-6-[(1-naphthyl)methyl]-4-oxo-1-thia-3a-aza-3-indanyl}(2-isonicotinoylhydrazino)formaldehyde, 7-Cyclopropyl-6-[(4-methoxy-1-naphthyl)methyl]-4-oxo-1-thia-3a-aza-3-indancarboxylic acid, (3R)-7-(Dimethylamino)-6-[(1-naphthyl)methyl]-4-oxo-1-thia-3a-aza-3-indancarboxylic acid, (3R)-5-Bromo-7-cyclopropyl-6-[(1-naphthyl)methyl]-4-oxo-1-thia-3a-aza-3-indancarboxylic acid, 7-Cyclopropyl-6-[(1-naphthyl)methyl]-1,1-dioxo-4-oxo-1-thia-3a-aza-3-indancarboxylic acid, (3R)-7-Cyclopropyl-4-oxo-6-[(2,3-xylidino)methyl]-1-thia-3a-aza-3-indancarboxylic acid, 7-Cyclopropyl-6-[(1-naphthyl)methyl]-1-oxo-4-oxo-1-thia-3a-aza-3-indancarboxylic acid, (3R)-7-Ethoxy-6-[(1-naphthyl)methyl]-4-oxo-1-thia-3a-aza-3-indancarboxylic acid, (3R)-6-[(1-Naphthyl)methyl]-4-oxo-7-(trifluoromethyl)-1-thia-3a-aza-3-indancarboxylic acid, (3R)-7-Isobutoxy-6-[(1-naphthyl)methyl]-4-oxo-1-thia-3a-aza-3-indancarboxylic acid, (3R)-7-Cyclopropyl-6-[(2-methoxy-1-naphthyl)methyl]-4-oxo-1-thia-3a-aza-3-indancarboxylic acid, (3R)-7-(Cyclopropylmethoxy)-6-[(1-naphthyl)methyl]-4-oxo-1-thia-3a-aza-3-indancarboxylic acid, 7-Cyclopropyl-6-[(2-methyl-1-aza-2-bora-1H-naphth-5-yl)methyl]-4-oxo-1-thia-3a-aza-3-indancarboxylic acid, 7-Cyclopropyl-6-[(2-methyl-1-aza-2-bora-1H-naphth-5-yloxy)methyl]-4-oxo-1-thia-3a-aza-3-indancarboxylic acid, 7-Cyclopropyl-6-[(2-methyl-1-aza-2-bora-1H-naphth-8-yl)methyl]-4-oxo-1-thia-3a-aza-3-indancarboxylic acid, 7-Cyclopropyl-6-[(2-methyl-1-aza-2-bora-1H-naphth-8-yloxy)methyl]-4-oxo-1-thia-3a-aza-3-indancarboxylic acid, or a pharmaceutically acceptable salt of any of the foregoing compounds, or a pharmaceutically acceptable salt of any one of the foregoing compounds.

Thus, the present disclosure provides a combination as described herein wherein the compound of Formula II is as defined in any one of Examples 1-54.

In still a further example, the combination described herein may comprise a compound of Formula II selected from one or more of:

1H-imidazol-1-ium 7-(benzo[d]oxazol-2-yl)-8-cyclopropyl-5-oxo-3,5-dihydro-2H-thiazolo[3,2-a]pyridine-3-carboxylate, 1H-imidazol-1-ium 8-cyclopropyl-7-(3-(naphthalen-1-yl)isoxazol-5-yl)-5-oxo-3,5-dihydro-2H-thiazolo[3,2-a]pyridine-3-carboxylate, 1H-imidazol-1-ium 8-cyclopropyl-5-oxo-7-(3-(3-(trifluoromethyl)phenyl)isoxazol-5-yl)-3,5-dihydro-2H-thiazolo[3,2-a]pyridine-3-carboxylate, 1H-imidazol-1-ium 8-cyclopropyl-5-oxo-7-(3-(thiophen-2-yl)isoxazol-5-yl)-3,5-dihydro-2H-thiazolo[3,2-a]pyridine-3-carboxylate, 1H-imidazol-1-ium 8-cyclopropyl-5-oxo-7-(3-phenylisoxazol-5-yl)-3,5-dihydro-2H-thiazolo[3,2-a]pyridine-3-carboxylate, 1H-imidazol-1-ium 6-bromo-7-(naphthalen-1-ylmethyl)-5-oxo-8-(3-phenylisoxazol-5-yl)-3,5-dihydro-2H-thiazolo[3,2-a]pyridine-3-carboxylate, 1H-imidazol-1-ium 7-(naphthalen-1-ylmethyl)-5-oxo-8-(3-phenyl-4,5-dihydroisoxazol-5-yl)-3,5-dihydro-2H-thiazolo[3,2-a]pyridine-3-carboxylate, 1H-imidazol-1-ium 8-ethynyl-7-(naphthalen-1-ylmethyl)-5-oxo-3,5-dihydro-2H-thiazolo[3,2-a]pyridine-3-carboxylate, 1H-imidazol-1-ium 7-(naphthalen-1-ylmethyl)-5-oxo-8-(3-phenylisoxazol-5-yl)-3,5-dihydro-2H-thiazolo[3,2-a]pyridine-3-carboxylate, 1H-imidazol-1-ium 8-(3-(naphthalen-1-yl)isoxazol-5-yl)-7-(naphthalen-1-ylmethyl)-5-oxo-3,5-dihydro-2H-thiazolo[3,2-a]pyridine-3-carboxylate, 1H-imidazol-1-ium 8-cyclopropyl-7-(naphthalen-1-ylmethyl)-5-oxo-3,5-dihydro-2H-thiazolo[3,2-a]pyridine-3-carboxylate, 8-cyclopropyl-5-oxo-7-(5-(3-(trifluoromethyl)phenyl)isoxazol-3-yl)-2,3-dihydrothiazolo[3,2-a]pyridine-3-carboxylic acid, 8-cyclopropyl-7-(5-(naphthalen-1-yl)isoxazol-3-yl)-5-oxo-2,3-dihydrothiazolo[3,2-a]pyridine-3-carboxylic acid, 8-cyclopropyl-7-(3-(naphthalen-2-yl)isoxazol-5-yl)-5-oxo-2,3-dihydrothiazolo[3,2-a]pyridine-3-carboxylic acid, 1H-imidazol-1-ium 7-(3-(benzo[d][1,3]dioxol-5-yl)isoxazol-5-yl)-8-cyclopropyl-5-oxo-2,3-dihydrothiazolo[3,2-a]pyridine-3-carboxylate, 1H-imidazol-1-ium 7-(3-(anthracen-9-yl)isoxazol-5-yl)-8-cyclopropyl-5-oxo-2,3-dihydrothiazolo[3,2-a]pyridine-3-carboxylate, 7-(3-(3,5-bis(trifluoromethyl)phenyl)isoxazol-5-yl)-8-cyclopropyl-5-oxo-2,3-dihydrothiazolo[3,2-a]pyridine-3-carboxylic acid, 8-cyclopropyl-7-(3-methylisoxazol-5-yl)-5-oxo-2,3-dihydrothiazolo[3,2-a]pyridine-3-carboxylic acid, 7-(3-(tert-butylamino)imidazo[1,2-a]pyridin-2-yl)-8-cyclopropyl-5-oxo-2,3-dihydrothiazolo[3,2-a]pyridine-3-carboxylic acid, 7-(3-(benzylamino)imidazo[1,2-a]pyridin-2-yl)-8-cyclopropyl-5-oxo-2,3-dihydrothiazolo[3,2-a]pyridine-3-carboxylic acid, 8-cyclopropyl-7-(3-((naphthalen-1-ylmethyl)amino)imidazo[1,2-a]pyridin-2-yl)-5-oxo-2,3-dihydrothiazolo[3,2-a]pyridine-3-carboxylic acid, 8-cyclopropyl-5-oxo-7-(3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-6-chloroimidazo[1,2-a]pyridin-2-yl)-8-cyclopropyl-5-oxo-2,3-dihydrothiazolo[3,2-a]pyridine-3-carboxylic acid, 7-(6-chloro-3-((naphthalen-1-ylmethyl)amino)imidazo[1,2-a]pyridin-2-yl)-8-cyclopropyl-5-oxo-2,3-dihydrothiazolo[3,2-a]pyridine-3-carboxylic acid, 7-(3-(benzylamino)-6-chloroimidazo[1,2-a]pyridin-2-yl)-8-cyclopropyl-5-oxo-2,3-dihydrothiazolo[3,2-a]pyridine-3-carboxylic acid, 7-(6-chloro-3-((3-(trifluoromethyl)benzyl)amino)imidazo[1,2-a]pyridin-2-yl)-8-cyclopropyl-5-oxo-2,3-dihydrothiazolo[3,2-a]pyridine-3-carboxylic acid, 7-(3-(tert-butylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-7-(3-((naphthalen-1-ylmethyl)amino)-7-(trifluoromethyl)imidazo[1,2-a]pyridin-2-yl)-5-oxo-2,3-dihydrothiazolo[3,2-a]pyridine-3-carboxylic acid, 7-(3-(benzylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-5-oxo-7-(7-(trifluoromethyl)-3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((naphthalen-1-ylmethyl)amino)imidazo[1,2-a]pyridin-2-yl)-5-oxo-2,3-dihydrothiazolo[3,2-a]pyridine-3-carboxylic acid, 7-(3-(benzylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((3-(trifluoromethyl)benzyl)amino)imidazo[1,2-a]pyridin-2-yl)-5-oxo-2,3-dihydrothiazolo[3,2-a]pyridine-3-carboxylic acid, or a pharmaceutically acceptable salt of any of the foregoing compounds.

Thus, the present disclosure provides a combination as described herein wherein the compound of Formula II is as defined in any one of Examples 56-88.

In still a further example, the combination described herein may comprise a compound of Formula II selected from one or more of (3R)-7-Cyclopropyl-6-[(1-naphthyl)methyl]-4-oxo-1-thia-3a-aza-3-indancarboxylic acid, 7-Cyclopropyl-4-oxo-6-{[m-(trifluoromethyl)phenyl]methyl}-1-thia-3a-aza-3-indancarboxylic acid, (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid, or a pharmaceutically acceptable salt of any of the foregoing compounds.

In this document, a compound is regarded as a drug against tuberculosis inhibiting the cytochrome b subunit of the bc1 complex, said cytochrome b subunit being encoded by the gene qcrB, in *Mycobacterium tuberculosis* (a QcrB inhibitor) when it is profiled in a test comprising the following steps:

(a) Overexpression of QcrB in a *Mycobacterium tuberculosis* strain using a mycobacterial vector, thereby expressing about 5-fold higher levels of QcrB (b) Transformation of another *Mycobacterium tuberculosis* strain with an empty mycobacterial vector (c) Preparation of a control culture comprising wild-type *Mycobacterium tuberculosis*

(d) Evaluation of MIC of said drug against tuberculosis on solid media plating $10^4$, $10^3$, $10^2$ and $10^1$ bacteria such as mycobacteria on agar containing different concentrations of said drug against tuberculosis in a dose response format, wherein MIC is defined as the lowest concentration of compound resulting in the complete inhibition of bacterial growth, and wherein the minimum inhibitory concentration (MIC) in the absence of QcrB over-expression (b) is unchanged compared to the control (c), and wherein the MIC is increased in the presence of over-expressed QcrB (a) by a factor of 5, 7, 10 or more.

The term 'profiling' or 'profiled' is used herein to describe an evaluation of the desired inhibitor of qcrB. Thus, in this document a method for profiling a qcrB enables the skilled person to choose a compound with the desired inhibitory effect to be combined according to the present disclosure.

In a further example, the drug against tuberculosis inhibiting the cytochrome b subunit of the bc1 complex, said cytochrome b subunit being encoded by the gene qcrB, in *Mycobacterium tuberculosis* may be a compound of Formula I:

Formula I or a pharmaceutically acceptable salt thereof,
wherein:

$R_{11}$ is selected from the group consisting of F, Cl, Br, I, methyl, methoxy, CN, $CF_3$ and $OCF_3$, $R_{22}$ is $C_1$-$C_4$ alkyl, Y is CH or N, $R_{33}$ is selected from the group consisting of:
a) F, Cl, Br, I, methyl, methoxy, CN, $CF_3$ and $OCF_3$,
b) C(O)OMe,
c) C(O)OH, and
d) $CH_2OH$.

Surprisingly, it has been found that a combination of a drug against tuberculosis as described herein and a compound of Formula II as described herein has a beneficial effect in the treatment of tuberculosis as evidenced in the examples section of this document and/or the drawings.

The compound of Formula I may be a compound of Formula Ia:

Formula Ia or a pharmaceutically acceptable salt thereof,
wherein $R_{11}$, $R_{22}$, Y and $R_{33}$ are as described herein.

Alternatively, the compound of Formula I may be a compound of Formula Ib:

Formula Ib or a pharmaceutically acceptable salt thereof,
wherein $R_{11}$, $R_{22}$, Y and $R_{33}$ are as described herein.

The compound of Formula Ia may have the following values for $R_{11}$, $R_{22}$, Y and $R_{33}$:
$R_{11}$ is Cl,
$R_{22}$ is ethyl,
Y is N, and
$R_{33}$ is $OCF_3$;
thereby providing the compound Q203:

Q203

Q203 may also be denominated a compound of Formula Ia'. The IUPAC name of Q203 is 6-chloro-2-ethyl-N-[(4-{4-

[4-(trifluoromethoxy)phenyl]piperidin-1-yl}phenyl)methyl] imidazo[1,2-a]pyridine-3-carboxamide. Q203 may be provided as a pharmaceutically acceptable salt. For instance, there is provided a ditosylate salt of Q203.

Further examples of drugs against tuberculosis inhibiting the cytochrome b subunit of the bc1 complex, said cytochrome b subunit being encoded by the gene qcrB, in *Mycobacterium tuberculosis* include one or more of the following compounds, or a derivative thereof, or a fragment thereof, and/or a pharmaceutically acceptable salt thereof:

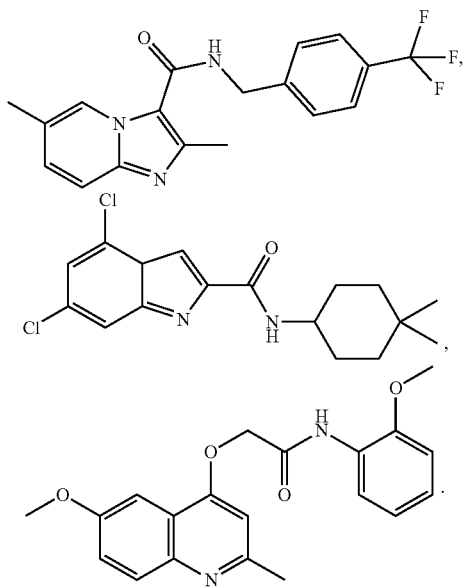
,

,

.

Further, it will be appreciated that instead of the isoniazide moiety of Formula IV another drug against tuberculosis may be used.

In this document, isonicotinylhydrazide has the chemical structure shown below. Isonicotinylhydrazide is also denominated isoniazid (INH). In this document, the terms isonicotinylhydrazide, isoniazid and INH are used interchangeably.

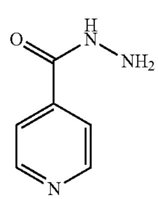

Isonicotinylhydrazide

In this document, the drugs rifampicin (RIF), pyrazinamide (PZA) and/or ethambutol (EMB) are understood to have the chemical structures depicted in FIG. 1. Further, bedaquiline, ethionamide, delamanide and pretomanid are understood to have the chemical structures depicted in FIG. 2.

Surprisingly, the inventors of the present disclosure have found that the compounds of Formula II described herein are useful in the treatment and/or prevention of tuberculosis.

The compounds of Formula II described herein may be used separately or in combination with a drug against tuberculosis inhibiting the cytochrome b subunit of the bc1 complex (encoded by the gene qcrB) in *Mycobacterium tuberculosis.*

In an example, there is provided a combination as described herein wherein the drug against tuberculosis is Q203.

The present disclosure further provides a combination comprising:

(i) a composition comprising or consisting of a drug against tuberculosis as described herein such as Q203, isonicotinylhydrazide or bedaquiline, or a pharmaceutically acceptable salt thereof, and (ii) a composition comprising or consisting of a compound of Formula II as described herein, or a pharmaceutically acceptable salt thereof.

Further, the combination described herein may be provided as a kit of parts. Thus, there is provided a kit of parts comprising:

(i) a composition comprising or consisting of a drug against tuberculosis such as Q203, isonicotinylhydrazide or bedaquiline, or a pharmaceutically acceptable salt thereof, and (ii) a composition comprising or consisting of a compound of Formula II as described herein, or a pharmaceutically acceptable salt thereof.

The combination described herein may be provided as a single composition comprising (i) a drug against tuberculosis as described herein such as Q203, isonicotinylhydrazide or bedaquiline, or a pharmaceutically acceptable salt thereof, and (ii) a compound of Formula II as described herein, or a pharmaceutically acceptable salt thereof.

For instance, the single composition may be provided as a tablet, lozenge or sirup.

The combination described herein such as the single composition or the kit of parts may further comprise instructions for use. For instance, the instructions for use may be instructions for separate, sequential or simultaneous use of the (i) composition comprising or consisting of a drug against tuberculosis such as Q203, isonicotinylhydrazide, or a pharmaceutically acceptable salt thereof and the (ii) composition comprising or consisting of a compound of Formula II as described herein, or a pharmaceutically acceptable salt thereof.

The drug against tuberculosis described herein may be selected from one or more of the following: Q203, isoniazid, rifampicin, pyrazinamide, ethambutol, pretomanid, delamanid, bedaquiline, streptomycin, levofloxacin, moxifloxacin and ofloxacin, cycloserine, terizidone, thionamide, protionamide, clofazimine and-4-aminosalicylic acid. For instance, the drug against tuberculosis described herein may be selected from one or more of the following: 6-chloro-2-ethyl-N-[(4-{4-[4-(trifluoromethoxy)phenyl]piperidin-1-yl}phenyl)methyl]imidazo[1,2-a]pyridine-3-carboxamide, isonicotinylhydrazide, bedaquiline, ethionamide, pretomanid, 4-aminosalisalicylic acid. In an example, the drug against tuberculosis may be 6-chloro-2-ethyl-N-[(4-{4-[4-(trifluoromethoxy)phenyl]piperidin-1-yl}pheynyl)methyl] imidazo[1,2-a]pyridine-3-carboxamide, isonicotinylhydrazide and/or bedaquiline, optionally in combination with one or more of ethambuthol, pyrazinamide, rifampicin. In a further example, the drug against tuberculosis may be as described elsewhere in this document. The combination of the present disclosure may further comprise a drug selected from the group consisting of rifampicin, pyrazinamide, ethambutol and 4-aminosalisalicylic acid. In particular, the combination of the present disclosure may further comprise a drug selected from the group consisting of rifampicin, pyrazinamide and ethambutol.

In an example, the drug against tuberculosis described herein may comprise or consist of Q203, isonicotinylhydrazide, rifampicin, pyrazinamide and ethambutol.

There is also provided a combination as described herein or a compound of Formula II as described herein for use as a medicament.

Further, there is provided a combination as described herein or a compound of Formula II as described herein for use in the treatment and/or prevention of tuberculosis as described herein.

There is also provided the use of a combination as described herein or a compound of Formula II as described herein for the manufacture of a medicament for the treatment and/or prevention of tuberculosis as described herein.

There is also provided a method for treatment and/or prevention of tuberculosis comprising administering to a mammal, such as a human or an animal, in need thereof an effective amount of a combination as described herein or a compound of Formula II as described herein. In this document, a mammal may be a human and/or an animal.

The tuberculosis described in this document may involve *Mycobacterium tuberculosis* (Mtb). Additionally or alternatively, the tuberculosis may involve one or more tuberculosis causing bacteria selected from the group consisting of *M. bovis, M. africanum, M. canetti* and/or *M. microti*. The tuberculosis may be active, latent, drug-sensitive and/or drug-resistant tuberculosis. Further, the tuberculosis may be one or more selected from the group consisting of pulmonary tuberculosis, military tuberculosis, laryngeal tuberculosis, extrapulmonary tuberculosis, tuberculosis peritonitis, tuberculosis pericarditis, osteal tuberculosis, renal tuberculosis, adrenal tuberculosis and tuberculosis meningitis.

The treatment described herein, such as a treatment using the combination of the present disclosure, may be curative treatment involving tuberculosis eradication or substantial tuberculosis eradication. In this document, the term eradication intends complete removal of tuberculosis bacteria or clinical cure where the bacteria are no longer detectable and the patient no longer has symptoms. These measures of eradication or clinical cure may be determined by sputum sampling and sputum smear and culture.

The prevention described herein, such as prevention using a compound of Formula II described herein, may involve preventing tuberculosis bacteria from multiplying and/or growing. The prevention is believed to occur by inhibiting lipid synthesis (in particular, but not limited to, in response to environmental changes) and altering the redox state of the bacteria.

As used herein, drug-resistant tuberculosis is intended to mean reduction in the effectiveness of a drug such as an antibiotic in the treatment of tuberculosis. The tuberculosis bacteria will then no longer be affected and/or killed by the drug or affected to a very limited extent. The drug-resistant tuberculosis may be one or more of the following: isoniazid resistant tuberculosis, multi-drug resistant tuberculosis, extensively resistant tuberculosis, totally resistant tuberculosis. Isoniazid resistant tuberculosis involves tuberculosis bacteria that are resistant to treatment with isoniazid. Multi-drug resistant tuberculosis involves tuberculosis bacteria that are resistant to treatment with at least two first line anti-tuberculosis drugs such as isoniazid and rifampicin. Extensively resistant tuberculosis involves tuberculosis bacteria that are resistant to at least rifampicin and isoniazid, to any member of quinolone broad-spectrum antibiotics and/or second line anti-tuberculosis drugs such as kanamycin, capreomyucin, amikacin.

While not wishing to be bound by any specific theory, it is believed that the compounds of Formula II of the present disclosure affect the tuberculosis bacteria by inhibiting lipid synthesis (in particular, but not limited to, in response to environmental changes) and altering the redox state of the bacteria. These direct effects lead to inhibition of the bacteria's ability to tolerate drugs against tuberculosis such as drugs against tuberculosis inhibiting the cytochrome b subunit of the bc1 complex (encoded by the gene qcrB) in *Mycobacterium tuberculosis*, tolerate low pH, tolerate reactive nitrogen and oxygen species, and form biofilms. The compounds of Formula II also inhibit growth in some standard media conditions, inhibit the selection for INH resistant mutants due to katG mutation and, therefore, decrease and/or inhibit the rate of INH resistance. Further, the compounds of Formula II of the present disclosure appear to sensitize resistant tuberculosis bacteria to treatment with a drug against tuberculosis as described herein, such as INH.

Thus, there is provided a compound of Formula II as described herein for use as a tuberculosis bacteria tolerance inhibitor. There is also provided the use of a compound of Formula II for the manufacture of a medicament for tuberculosis bacteria tolerance inhibition. There is also provided a method for tuberculosis bacteria tolerance inhibition comprising administering to a mammal, such as a human or an animal, an effective amount of a compound of Formula II as described herein. There is also provided a use of a compound of Formula II as described herein as a tuberculosis bacteria tolerance inhibitor. The tuberculosis may be as described herein.

Thus, there is provided a compound of Formula II as described herein for use in sensitizing tuberculosis bacteria to treatment with a drug against tuberculosis inhibiting the cytochrome b subunit of the bc1 complex (encoded by the gene qcrB) in *Mycobacterium tuberculosis*. There is also provided the use of a compound of Formula II as described herein for the manufacture of a medicament for use in sensitizing tuberculosis bacteria to treatment with a drug against tuberculosis inhibiting the cytochrome b subunit of the bc1 complex (encoded by the gene qcrB) in *Mycobacterium tuberculosis*. There is also provided a method for sensitizing tuberculosis bacteria to treatment with a drug against tuberculosis inhibiting the cytochrome b subunit of the bc1 complex (encoded by the gene qcrB) in *Mycobacterium tuberculosis* comprising administering to a mammal, such as a human or an animal, an effective amount of a compound of Formula II as described herein. There is also provided a use of a compound of Formula II as described herein to sensitize tuberculosis bacteria to treatment with a drug against tuberculosis inhibiting the cytochrome b subunit of the bc1 complex (encoded by the gene qcrB) in *Mycobacterium tuberculosis*. The tuberculosis and/or the drug against tuberculosis may be as described herein.

Thus, there is provided a compound of Formula II as described herein to improve the efficacy of a drug against tuberculosis inhibiting the cytochrome b subunit of the bc1 complex (encoded by the gene qcrB) in *Mycobacterium tuberculosis*. There is also provided the use of a compound of Formula II as described herein for the manufacture of a medicament to improve the efficacy of a drug against tuberculosis inhibiting the cytochrome b subunit of the bc1 complex (encoded by the gene qcrB) in *Mycobacterium tuberculosis*. There is also provided a method for sensitizing tuberculosis bacteria to treatment with a drug against tuberculosis inhibiting the cytochrome b subunit of the bc1 complex (encoded by the gene qcrB) in *Mycobacterium tuberculosis* comprising administering to a mammal, such as a human or an animal, an effective amount of a compound of Formula II as described herein to improve the efficacy of a drug against tuberculosis inhibiting the c Salts The compounds of the present disclosure may be provided as a pharmaceutically acceptable salt. A suitable pharmaceutically acceptable salt of a compound of the present disclosure may be, for example, a base-addition salt of a compound of the present disclosure which is sufficiently acidic, for example, a metal salt, for example, lithium, sodium, potassium, calcium, magnesium, zinc or aluminum, an ammonium salt, a salt with an organic base which affords a physiologically acceptable cation, which includes quartenery ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R, 2S)-2-hydroxyinden-1-amine, morpholine, N-methylpiperidine, N-ethylpiperidine, imidazole, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine. In an example, there is provided an imidazole salt of the compounds of the present disclosure.

Solvates or Hydrates

Certain compounds of the present disclosure may exist as solvates or hydrates. It is to be understood that the present disclosure encompasses all such solvates or hydrates. Compounds of the present disclosure may also contain unnatural proportions of atomic isotopes at one or more of the atoms that constitute such compounds. For example, the isotope may be deuterium. In a further example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure.

Co-Crystals

In a salt, proton transfer may occur between the active pharmaceutical ingredient and the counter ion of the salt. However, in some cases there is no or only partial proton transfer and the solid is therefore not a true salt. It is accepted that the proton transfer is in fact a continuum, and can change with temperature, and therefore the point at which a salt is better described as a "co-crystal" may be subjective. The term "co-crystal" as used herein refers to multicomponent system in which there exists a host molecule or molecules (active pharmaceutical ingredient) and a guest (or co-former) molecule or molecules. The guest or co-former molecule is defined as existing as a solid at room temperature in order to distinguish the co-crystal from solvates. However, a co-crystal may itself form solvates.

In a co-crystal there is generally predominance for interaction through non-ionic forces, such as hydrogen bonding.

Polymorphs

Compounds of the present disclosure may exist in a continuum of solid states ranging from fully amorphous to fully crystalline. Thus, it is to be understood that all polymorphs, such as mixtures of different polymorphs, are included within the scope of the claimed compounds.

Prodrugs

In addition, compounds of the present disclosure may be administered in the form of a prodrug. A prodrug is a compound which may have little or no pharmacological activity itself, but when such compound is administered into or onto the body of a patient, it is converted into a compound of Formula II.

Methods of Preparation

The compounds of Formula II may be prepared as described in WO 2011/113606, WO 2015/014993 or European Journal of Medicinal Chemistry 125 (2017) 807-815. Sunde Kang et al. The compounds of Formula II of the present disclosure may be prepared as described in WO 2014/185833. The compounds may also be prepared as described for structurally related compounds. The reactions may be carried out as in standard procedures or as described in the experimental section of this document. The sulfide of the compounds of Formula II may be oxidized with the aid of meta-chloroperoxybenzoic acid (mCPBA) to sulphoxide and sulphone, respectively. Additionally or alternatively, the compounds may be prepared as depicted in Schemes 1 to 10 as depicted below.

Scheme 1a

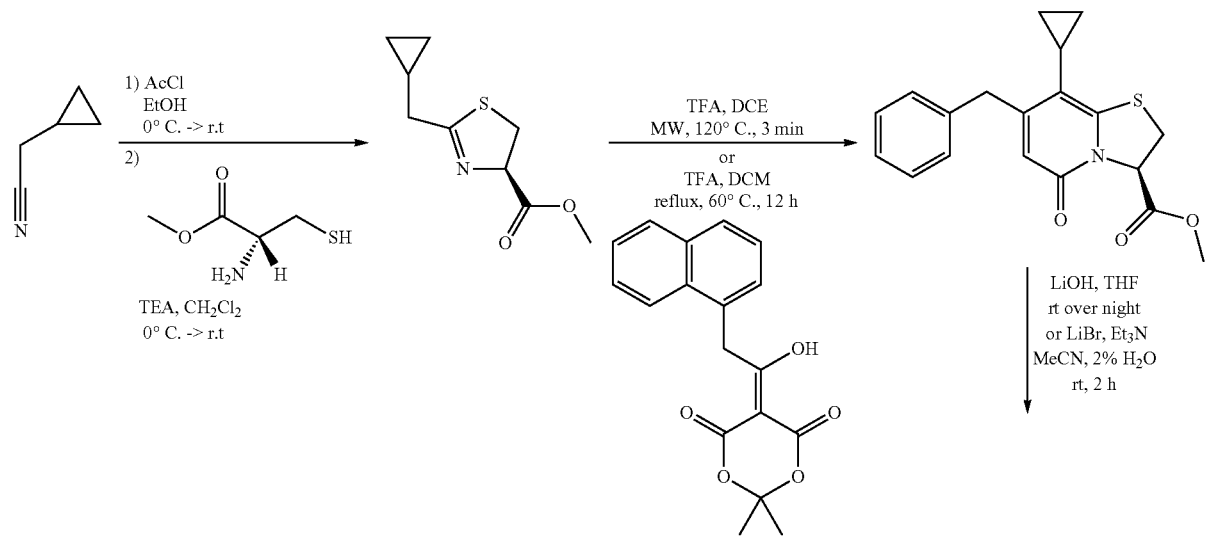

-continued
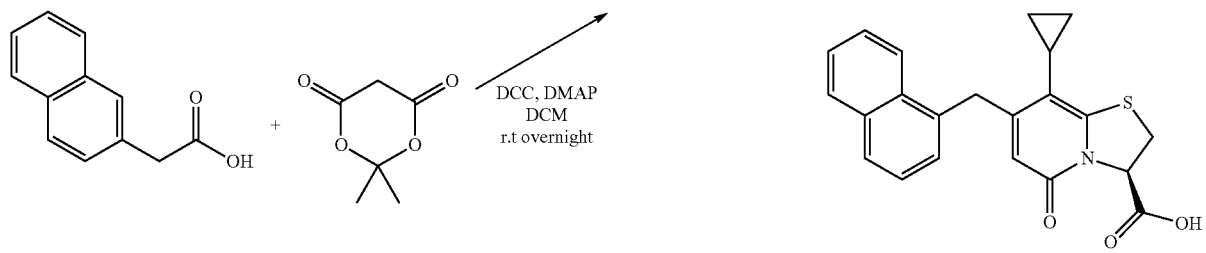
Scheme 1b
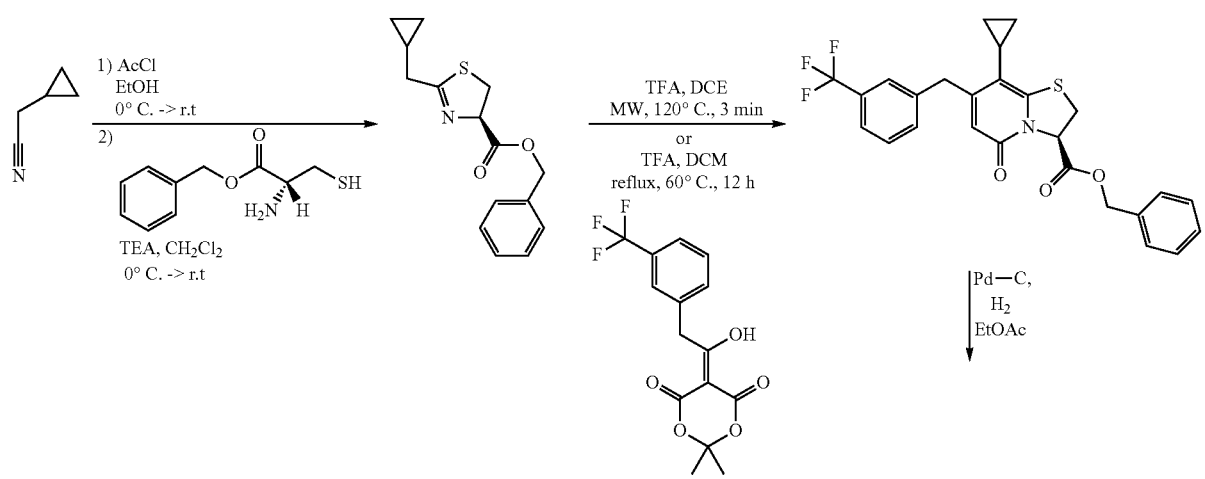
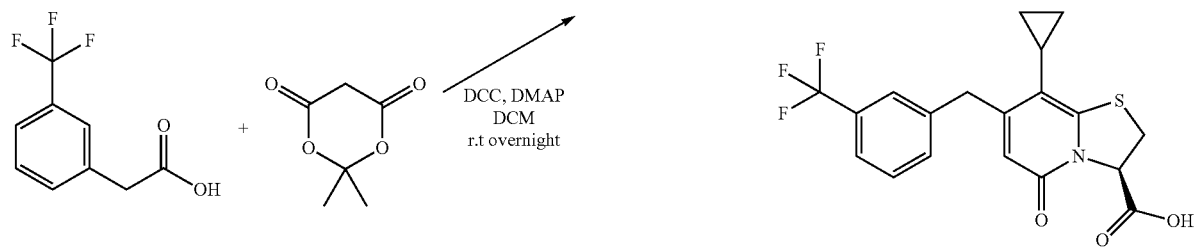
Scheme 2
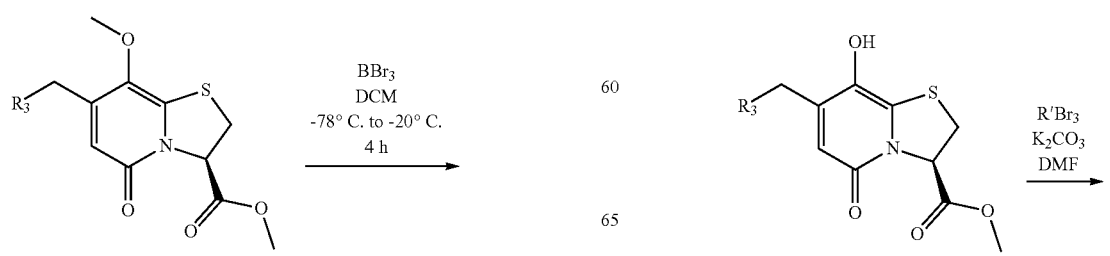

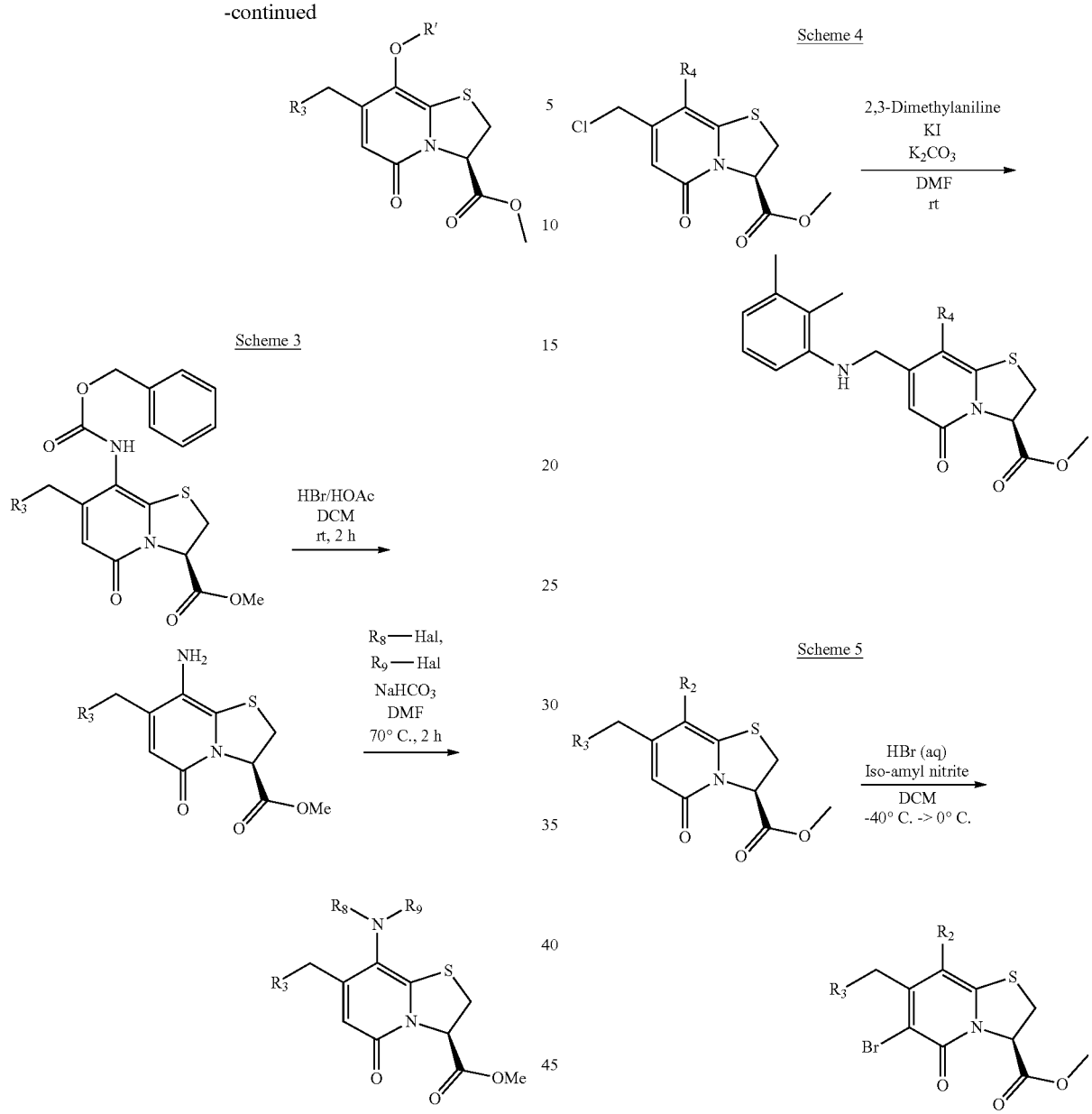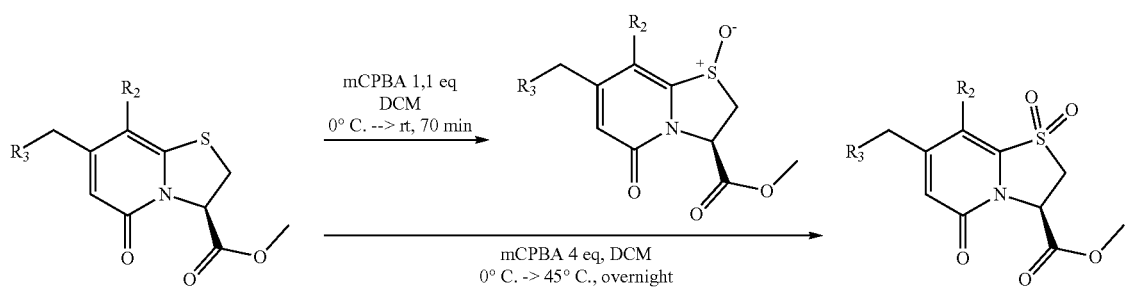

Scheme 7
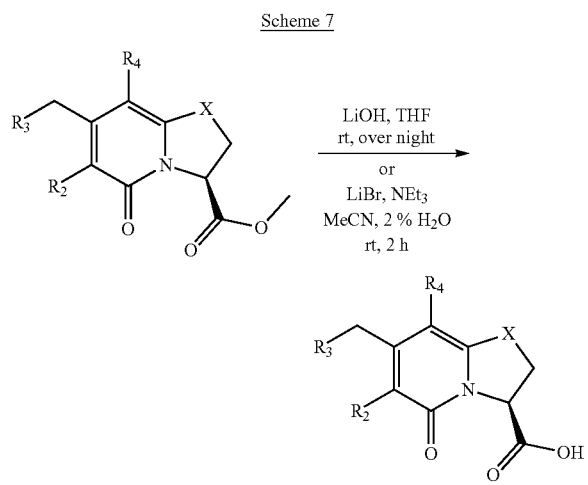
Scheme 8
Scheme 9
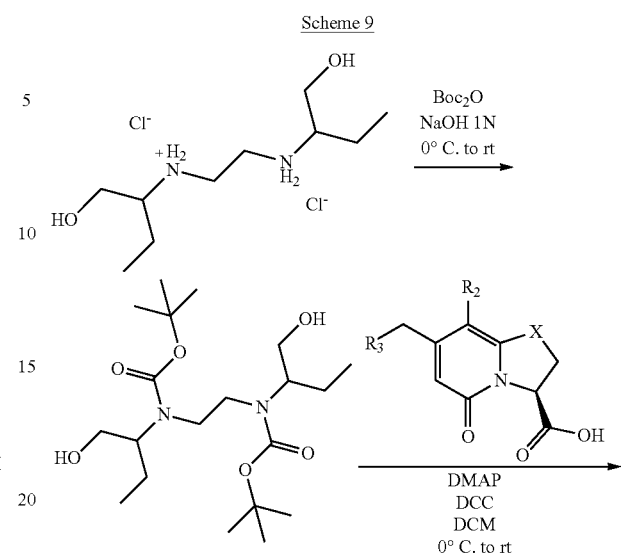
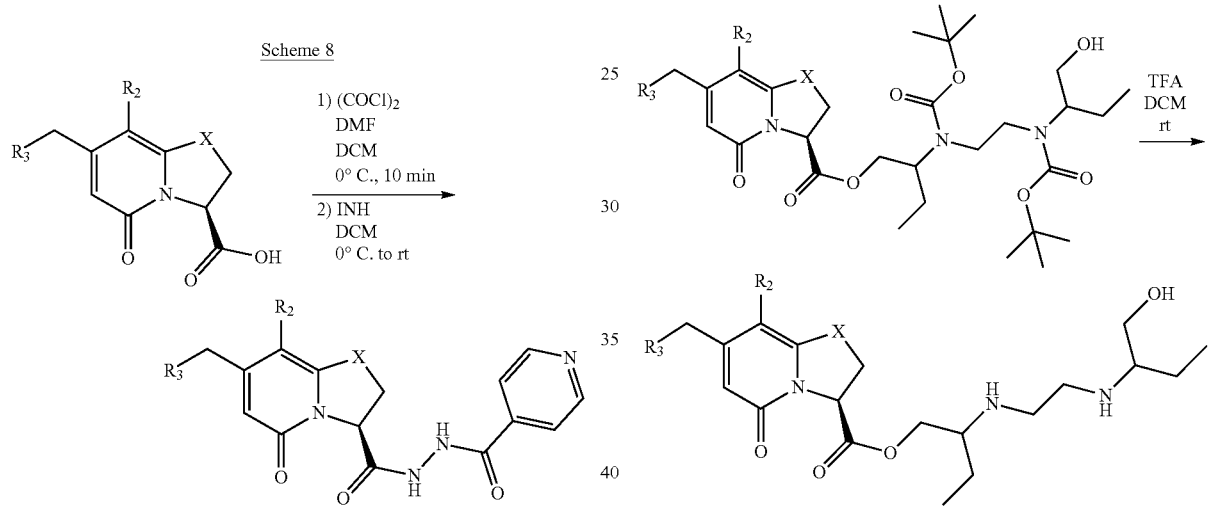
Scheme 10
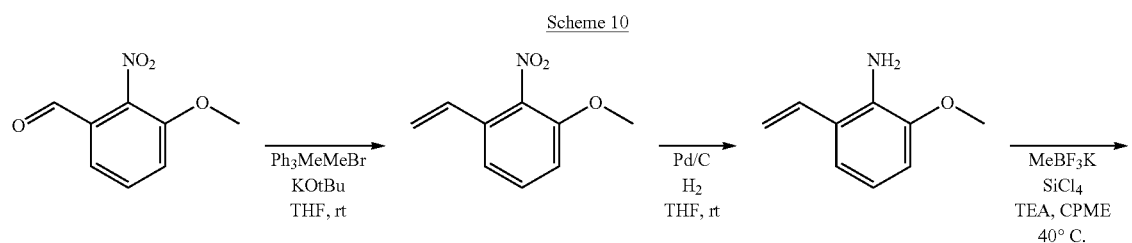
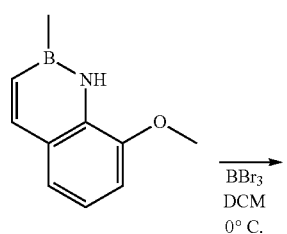

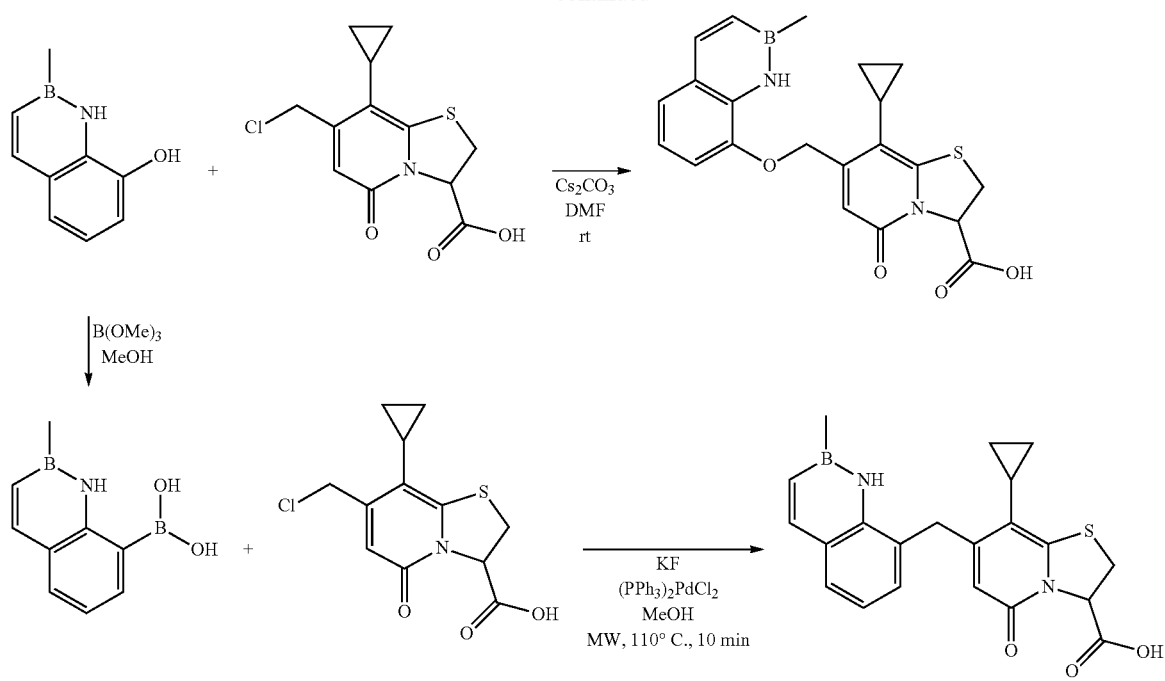
Scheme 11
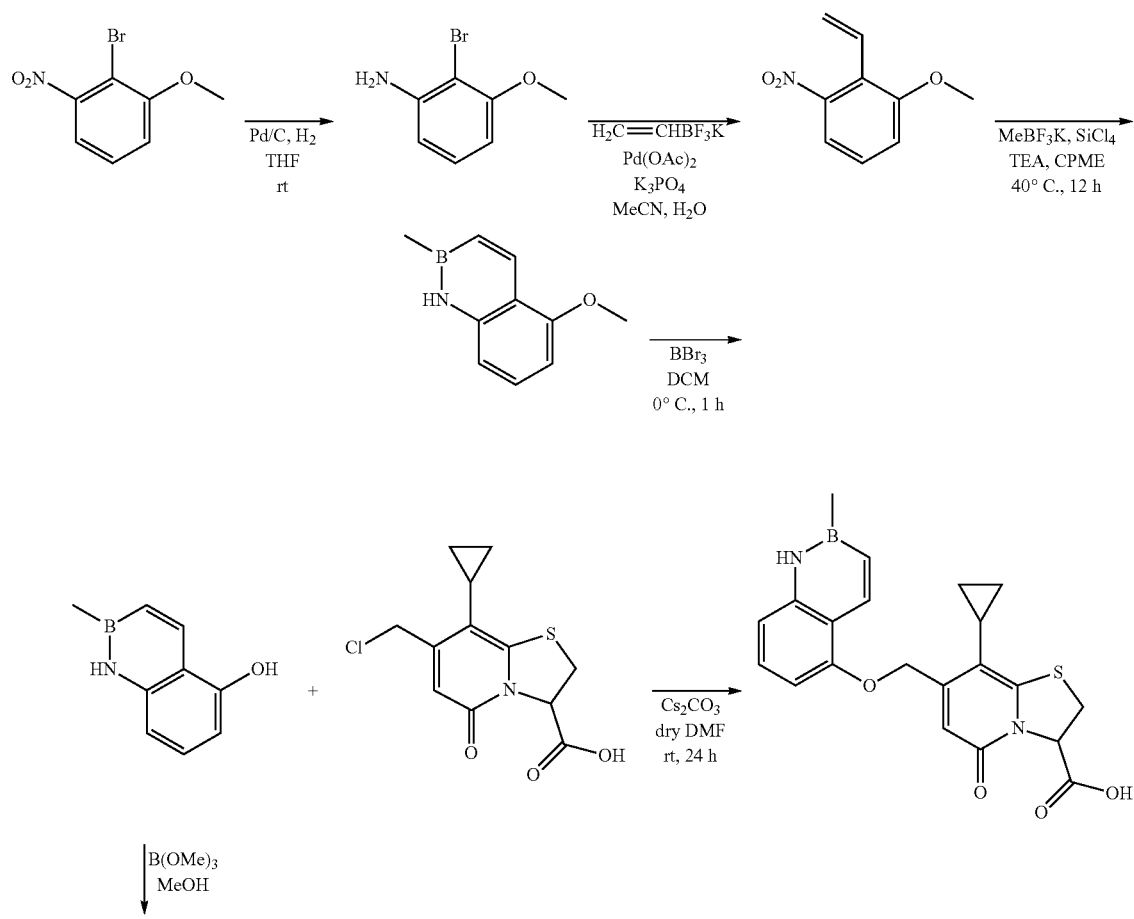

-continued

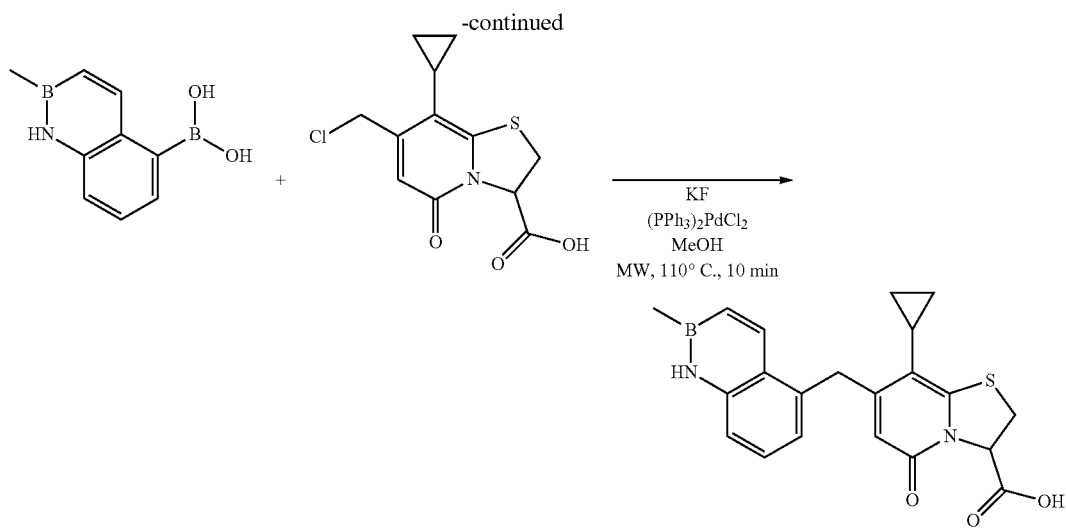

Intermediates

The present disclosure provides compounds which may be used as intermediates in the synthesis of compounds of Formula II described herein. For instance, the intermediates may be one or more of the following compounds:

Benzyl (4R)-2-(cyclopropylmethyl)$\Delta^2$-1,3-thiazoline-4-carboxylate,

5-{1-Hydroxy-2-[m-(trifluoromethyl)phenyl]ethylidene}-2,2-dimethyl-1,3-dioxane-4,6-dione, Benzyl (3R)-7-cyclopropyl-4-oxo-6-{[m-(trifluoromethyl)phenyl]methyl}-1-thia-3a-aza-3-indancarboxylate, Methyl (3R)-7-cyclopropyl-4-oxo-6-{[m-(trifluoromethyl)phenyl]methyl}-1-thia-3a-aza-3-indancarboxylate.

These intermediates may be used in the synthesis of compounds of Formula II wherein $R_3$ is meta-trifluoromethyl, i.e. compounds having the following chemical structure:

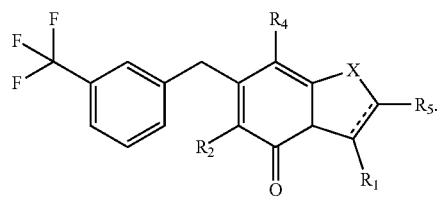

Derivatives of 4-aminosalicylic Acid 4-aminosalicylic acid, commonly known as PAS, is an antibiotic used to treat tuberculosis. The present disclosure provides a combination comprising:

(i) 4-aminosalicylic acid, i.e.

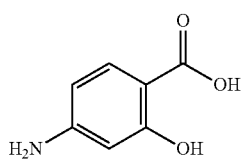 [SMILES: Nc1ccc(C(=O)O)c(O)c1]

or a pharmaceutically acceptable salt thereof, and (ii) a compound of Formula II as described herein, wherein $R_1$, $R_2$, $R_3$, $R_4$, $R_5$ and X may have values as described in this document, or a pharmaceutically acceptable salt thereof.

4-aminosalicylic acid may form a covalent bond with the $R_1$ group of the compounds of Formula II disclosed herein resulting in a compound of Formula V:

Formula V

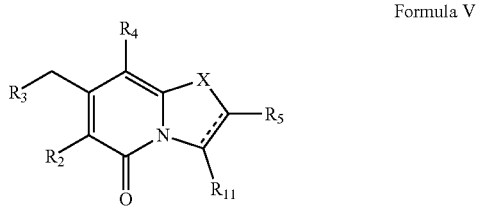

wherein $R_{11}$ is selected from:

a)

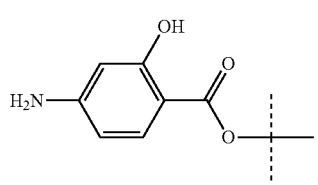

b)

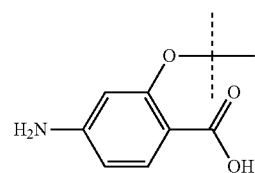

c)

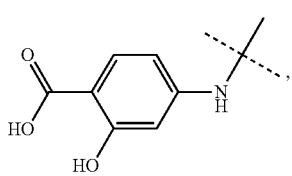

and $R_2$, $R_3$, $R_4$, $R_5$ and X may have values as described in this document, or a pharmaceutically acceptable salt thereof.

The compound of Formula V may exist as a compound of Formula Va and Formula Vb, respectively:

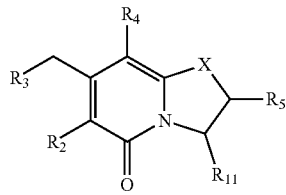

Formula Va

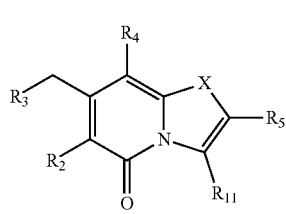

Formula Vb wherein $R_2$, $R_3$, $R_4$, $R_5$, $R_{11}$ and X may have values as described in this document,
or a pharmaceutically acceptable salt thereof.

The compound of Formula Va may exist as cis and trans stereoisomers. The present disclosure encompasses all these compounds which are denominated compounds of Formula Va1, Va2, Va3 and Va4, the chemical structures of which are shown in FIG. 8.

Further, there is provided a compound of Formula V as described herein for use as a medicament in therapy.

There is also provided a compound of Formula V as described herein for use in the treatment and/or prevention of tuberculosis. There is also provided the use of a compound of Formula V as described herein for the manufacture of a medicament for the treatment and/or prevention of tuberculosis. There is also provided a method for the treatment and/or prevention of tuberculosis comprising administering to a mammal, such as a human or an animal, an effective amount of a compound of Formula V as described herein. The tuberculosis may be as described in this document.

REFERENCES

1. Org. Biomol. Chem., 2005, 3, 3886-3892, Aberg, Veronica et al.
2. Bioorganic & Medicinal Chemistry Letters (2008), 18(12), 3536-3540, Aberg, Veronica et al.
3. Journal of Medicinal Chemistry (2010), 53(15), 5690-5695, Chorell, Erik et al
4. Tetrahedron Letters (2007), 48(26), 4543-4546, Pemberton, Nils et al
5. Bioorganic & Medicinal Chemistry (2012), 20(9), 3128-3142, Chorell, Erik et al.
6. Organic & Biomolecular Chemistry (2005), 3(15), 2817-2823, Aaberg, Veronica et al
7. WO2014/185853 A1.
8. Journal of Organic Chemistry (2007), 72(13), 4917-4924, Chorell, Erik et al.
9. Comb. Chem. 2002, 4, 630-639, Emtenas, Hans et al.
10. J. Med. Chem. 2016, 59, 2094-2108, James A. D. Good et al.
11. Cell Chemical Biology 23, 404-414, James A. D. Good et al.
12. PCT/EP2015/076578
13. WO 2011/113606
14. WO 2015/014993
15. WO 2012/143796

The disclosure is further illustrated by the following non-limitative Examples

EXAMPLES

In this document, unless otherwise stated, the naming and the drawing of the chemical compounds and radicals have been made using the program Chem Doodle version 7.0.1 7.0.2 or 9.0.3, or the program Chemdraw version 12.0.3.1216 or 14.0.0.117. If the name and drawing are inconsistent, the chemical structure shall be considered to be correct.

Abbreviations
ANOVA Analysis of variance
aq aqueous
BOC tert-butyloxycarbonyl
BSA Bovine Serum Albumine
CFU Colony Forming Unit
CPME Cyclopentyl methyl ether
DCC Dicyclohexyl carbodiimide
DMAP Dimethyl aminopyridine
DMF Dimethyl formamide
DCM Dichloromethane
EMB Ethambutol
FAB Fast Atom Bombardment
HRMS High Resolution Mass Spectrosopy
INH Isoniazide or isonicotinylhydrazide
IUPAC International Union of Pure and Applied Chemistry
OADC Middlebrook Oleic Albumin Dextrose Catalase Growth Supplement
KatG catalase-peroxidase
MeCN Acetonitrile
MIC minimum inhibitory concentration
MicroM micromolar
μM micromolar
Mtb *Mycobacterium tuberculosis*
MW Microwave heating
MS Mass Spectroscopy
NMR Nuclear Magnetic Resonance
ND none detected
nm nanometer
OD optical density
λ wavelength
ODλ$_{600}$ optical density at 600 nm
PBS Phosphate-Buffered Saline buffer
PZA Pyrazinamide
RIF Rifampicin or Rifampin
RT room temperature
rt room temperature
sat saturated
TB tuberculosis
TEA Triethylamine
TFA Trifluoroacetic acid
THF Tetrahydrofuran
TWEEN 80 Polyoxyethylenesorbitan monooleate
WT Wild Type
7H9 BD Difco™ Dehydrated Culture Media: Middlebrook 7H9 Broth supplied by Fisher Scientific
Chemistry
General
$^1$H NMR spectra were recorded on a 400 or 600 MHz spectrometer at 298 K and calibrated by using the residual peak of the solvent as the internal standard (CDCl$_3$: $\delta_H$=7.26 ppm; $\delta_C$=77.16 ppm; DMSO-d$_6$: $\delta_H$=2.50 ppm; $\delta_C$=39.52 ppm). The purity of all final compounds was ≥95% by LC-MS.

Examples 1-88

The compounds of Examples 1-88 were prepared in accordance with or in analogy with references 1-11 as described herein or as described in this document. $^1$H NMR data are provided for the compounds 36-50. Additionally, NMR data are provided for examples 1, and 27. Table 1 shows data for Examples 1-54.

By way of example, the compound of Example 1 was prepared as follows.

Example 1

(3R)-7-Cyclopropyl-6-[(1-naphthyl)methyl]-4-oxo-1-thia-3a-aza-3-indancarboxylic acid Cyclopropylacetonitrile was reacted with ethanol and acetyl chloride to generate 2-cyclopropyl-1-ethoxy-1-ethanimine that was reacted with R)-cysteine methyl ester hydrochloride and Et$_3$N in CH$_2$Cl$_2$ without any workup to form Methyl 2-(cyclopropylmethyl)Δ$^2$-1,3-thiazoline-4-carboxylate. (1-Naphthyl)acetic acid activated with DCC and DMAP was reacted with 2,2-Dimethyl-1,3-dioxane-4,6-dione in DCM to give 5-[1-Hydroxy-2-(1-naphthyl)ethylidene]-2,2-dimethyl-1,3-dioxane-4,6-dione.

These two building blocks were allowed to react with TFA at elevated temperature to give Benzyl (3R)-7-cyclopropyl-4-oxo-6-{[m-(trifluoromethyl)phenyl]methyl}-1-thia-3a-aza-3-indancarboxylate. Hydrolysis with LiOH in THF or LiBr and Et3N in wet (2%) acetonitrile gave (3R)-7-Cyclopropyl-6-[(1-naphthyl)methyl]-4-oxo-1-thia-3a-aza-3-indancarboxylic acid (Scheme 1). NMR and MS data are provided in Table 1.

Examples 73-88

The compounds of Examples 73-88 were prepared or may be prepared as follows. A solution of 2-aminopyridine (0.4 mmol), aldehyde (0.4 mmol) and AcOH (0.8 mmol) in methanol (1.5 mL) was stirred for 25 min. at room temperature in a 10 mL glass pressure microwave tube. This was followed by the addition of isocyanide (0.4 mmol) and the mixture was subjected to microwave irradiation (Temperature: 130° C.) for 1 h. The reaction mixture was allowed to cool to rt and evaporated under vacuo. The reaction mixture was dissolved with EtOAc and washed with saturated NaHCO$_3$(aq) and brine. The organic phase was dried over anhydrous Na$_2$SO$_4$, filtered and concentrated under reduced pressure. The crude product was purified by column chromatography on silica gel eluting with CH$_2$Cl$_2$/MeOH (95:5) gradient.

TABLE 1

$^1$H-NMR and and HRMS data

| Example Number | Chemical Structure | Compound name |
|---|---|---|
| 1 | (structure shown) $^1$H NMR: δ7.93-7.99 (m, 1H), 7.83-7.92 (m, 2H), 7.46-7.56 (m, 3H), 7.36 (d, J 6.95 Hz, 1H), 5.16 (s, 1H), 4.92-4.97 (m, 1H), 4.45 (d, J 17.29 Hz, 1H), 4.34 (d, J 17.29 Hz, 1H), 3.47-3.56 (m, 2H), 1.62-1.69 (m, 1H), 0.78-0.96 (m, 2H), 0.56-0.73 (m, 2H). HRMS(FAB+) calcd for (M + 1) C$_{22}$H$_{20}$NO$_3$S: 378.1164. Observed: 378.1163. | (3R)-7-Cyclopropyl-6-[(1-naphthyl)methyl]-4-oxo-1-thia-3a-aza-3-indancarboxylic acid |
| 2 | (structure shown) $^1$H NMR (400 MHz, DMSO-d6): δ = d 0.53-0.73 (m, 2H), 0.81-0.97 (m, 2H), 1.56-1.67 (m, 1H), 3.50 (dd J1 = 1.81 Hz, J2 = 11.93 Hz, 1H), 3.78 (dd J1 = 9.12 Hz, J2 = 11.91 Hz, 1H), 4.15-4.30 (m, 2H), 5.37 (dd J1 = 1.78 Hz, J2 = 9.10 Hz, 1H), 5.61 (s, 1H), 7.35-7.43 (m, 2H), 7.47 (s, 1H), 7.71-7.77(m, 1H), 7.97-8.04 (m, 1H). HRMS (electrospray ionization) calcd for [M + Li] C$_{20}$H$_{16}$NO$_3$S$_2$ 382.0572. Observed 382.0578 | (3R)-7-Cyclopropyl-4-oxo-6-{(7-thiabicyclo[4.3.0]nona-1,3,5,8-tetraen-8-yl)methyl}-1-thia-3a-aza-3-indancarboxylic acid |

TABLE 1-continued

¹H-NMR and and HRMS data

| Example Number | Chemical Structure | Compound name |
|---|---|---|
| 3 | | (3R)-7-Cyclopropyl-6-[(4-fluoro-1-naphthyl)methyl]-4-oxo-1-thia-3a-aza-3-indancarboxylic acid |
| 4 | | (3R)-7-Cyclopropyl-6-[(4-methyl-1-naphthyl)methyl]-4-oxo-1-thia-3a-aza-3-indancarboxylic acid |
| 5 | | (3S)-7-Cyclopropyl-6-[(1-naphthyl)methyl]-4-oxo-1-thia-3a-aza-3-indancarboxylic acid |
| 6 | | 5-Cyclopropyl-4-[(1-naphthyl)methyl]-2-oxo-8-(3-thienyl)-7-thia-1-azabicyclo[4.3.0]nona-3,5,8-triene-9-carboxylic acid |
| 7 | | (3R)-7-Cyclopropyl-6-[(1-naphthyloxy)methyl]-4-oxo-1-thia-3a-aza-3-indancarboxylic acid |
| 8 | | (3R)-7-Cyclopropyl-6-[(2-fluoro-5-methyl-phenyl)methyl]-4-oxo-1-thia-3a-aza-3-indancarboxylic acid |

TABLE 1-continued

| Example Number | Chemical Structure | Compound name |
|---|---|---|
| 9 | 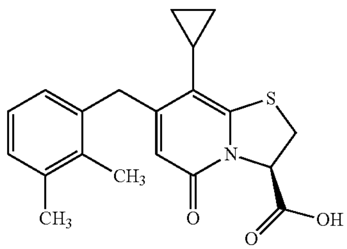 [SMILES: Cc1cccc(Cc2cc(=O)n3c(c2C2CC2)SC[C@H]3C(=O)O)c1C] | (3R)-7-Cyclopropyl-4-oxo-6-[(2,3-xylyl)methyl]-1-thia-3a-aza-3-indancarboxylic acid |
| 10 | 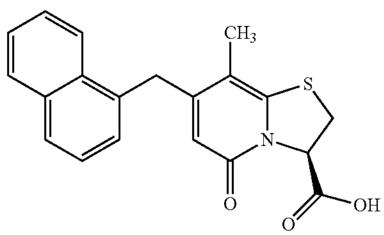 [SMILES: Cc1c(Cc2cccc3ccccc23)cc(=O)n2c1SC[C@H]2C(=O)O] | (3R)-7-Methyl-6-[(1-naphthyl)methyl]-4-oxo-1-thia-3a-aza-3-indancarboxylic acid |
| 11 | 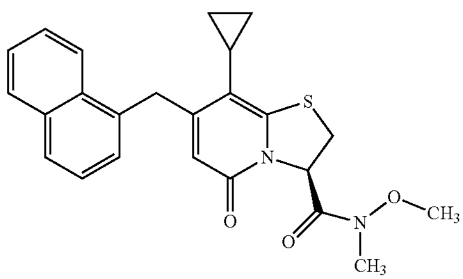 [SMILES: CON(C)C(=O)[C@@H]1CSc2c(C3CC3)c(Cc3cccc4ccccc34)cc(=O)n21] | (N-Methylmethoxyamino){(3R)-7-cyclopropyl-6-[(1-naphthyl)methyl]-4-oxo-1-thia-3a-aza-3-indanyl}formaldehyde |
| 12 | 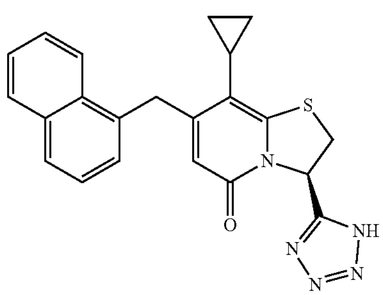 [SMILES: O=c1cc(Cc2cccc3ccccc23)c(C2CC2)c2n1[C@H](c1nnn[nH]1)CS2] | (3R)-7-Cyclopropyl-6-[(1-naphthyl)methyl]-3-(1H-1,2,3,4-tetrazol-5-yl)-1-thia-3a-aza-4-indanone |
| 13 | 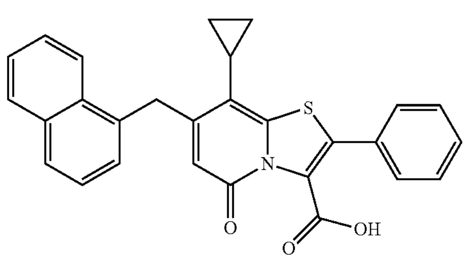 [SMILES: O=C(O)c1c(-c2ccccc2)sc2c(C3CC3)c(Cc3cccc4ccccc34)cc(=O)n12] | 5-Cyclopropyl-4-[(1-naphthyl)methyl]-2-oxo-8-phenyl-7-thia-1-azabicyclo[4.3.0]nona-3,5,8-triene-9-carboxylic acid |

TABLE 1-continued

¹H-NMR and and HRMS data

| Example Number | Chemical Structure | Compound name |
|---|---|---|
| 14 | | 5-Cyclopropyl-4-[(1-naphthyl)methyl]-2-oxo-8-(m-tolyl)-7-thia-1-azabicyclo[4.3.0]nona-3,5,8-triene-9-carboxylic acid |
| 15 | | (3R)-7-Cyclopropyl-6-[(2-naphthyl)methyl]-4-oxo-1-thia-3a-aza-3-indancarboxylic acid |

¹H NMR (DMSO, 400 MHz) d = 8.13-8.10 (m, 1H), 7.95-7.92 (m, 1H), 7.67-7.64 (m, 2H), 7.54 (s, 1H), 7.37-7.31 (m, 2H), 5.25 (d, 1H, J = 8.8 Hz), 5.23 (s, 1H), 4.46 (d, 1H, J = 17.6 Hz), 4.37 (d, 1H, J = 17.6 Hz), 3.72 (dd, 1H, J = 9.2, 11.6 Hz), 3.51 (d, 1H, J = 11.6 Hz), 1.74-1.67 (m, 1H), 0.93-0.86 (m, 2H), 0.66-0.60 (m, 2H) ppm.

| Example Number | Chemical Structure | Compound name |
|---|---|---|
| 16 | | (3R)-7-Cyclopropyl-3-(hydroxymethyl)-6-[(1-naphthyl)methyl]-1-thia-3a-aza-4-indanone |
| 17 | | (3R)-6-[(1-Naphthyl)methyl]-4-oxo-7-(2-thienyl)-1-thia-3a-aza-3-indancarboxylic acid |
| 18 | | 5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid |

TABLE 1-continued

| Example Number | Chemical Structure | Compound name |
|---|---|---|
| 19 | | 8-Benzyl-5-cyclopropyl-4-[(1-naphthyl)methyl]-2-oxo-7-thia-1-azabicyclo[4.3.0]nona-3,5,8-triene-9-carboxylic acid |
| 20 | | (3R)-7-Cyclopropyl-6-[(2,3-dichlorophenyl)methyl]-4-oxo-1-thia-3a-aza-3-indancarboxylic acid |
| 21 | | (3R)-7-Cyclopropyl-6-[(1-naphthyl)methyl]-4-oxo-1-thia-3a-aza-3-indancarboxamide |
| 22 | | {(3R)-7-Cyclopropyl-6-[(1-naphthyl)methyl]-4-oxo-1-thia-3a-aza-3-indanyl}(phenylsulfonylamino)formaldehyde |
| 23 | | (3R)-7-Isopropyl-6-[(1-naphthyl)methyl]-4-oxo-1-thia-3a-aza-3-indancarboxylic acid |
| 24 | | (3R)-7-Cyclopropyl-6-methyl-4-oxo-1-thia-3a-aza-3-indancarboxylic acid |

TABLE 1-continued

| Example Number | Chemical Structure | Compound name |
|---|---|---|
| 25 | | (3R)-6-[(p-Chlorophenyl)methyl]-7-cyclopropyl-4-oxo-1-thia-3a-aza-3-indancarboxylic acid |
| 26 | | {(3R)-7-Cyclopropyl-6-[(1-naphthyl)methyl]-4-oxo-1-thia-3a-aza-3-indanyl}(methylsulfonylamino)formaldehyde |
| 27 | | (3R)-7-Cyclopropyl-4-oxo-6-[(m-tolyl)methyl]-1-thia-3a-aza-3-indancarboxylic acid |

$^1$H NMR(400 MHz, DMSO-d6): δ = 7.23-7.19 (m, 1H), 7.06-7.00 (m, 3H), 5.73 (s, 1H), 5.36 (dd, 1H, J = 1.6, 9.2 Hz), 3.93 (ABq, 2H, J = 18.2 Hz), 3.77 (dd, 1H, J = 9.2 Hz, 12 Hz), 3.50 (dd, 1H, J = 1.6 Hz, 11.6 Hz), 2.28 (s, 3H), 1.46-1.39 (m, 1H), 0.95-0.82 (m, 2H), 0.65-0.60 (m,1H), 0.59-0.49 (m, 1H) ppm.

| | | |
|---|---|---|
| 28 | | (3R)-7-Isopropyl-4-oxo-6-[2-(m-tolyl)ethyl]-1-thia-3a-aza-3-indancarboxylic acid |
| 29 | | 7-(1-Methyl-1H-indol-3-yl)-6-[(1-naphthyloxy)methyl]-4-oxo-1-thia-3a-aza-3-indancarboxylic acid |

TABLE 1-continued

| Example Number | Chemical Structure | Compound name |
|---|---|---|
| 30 | | (3R)-6-[(4-Bromo-1-naphthyl)methyl]-7-cyclopropyl-4-oxo-1-thia-3a-aza-3-indancarboxylic acid |
| 31 | | 7-Cyclopropyl-6-[(1-naphthyl)methyl]-1-thia-3a-aza-4-indanone |
| 32 | | (3R)-7-Cyclopropyl-5-(hydroxymethyl)-6-[(1-naphthyl)methyl]-4-oxo-1-thia-3a-aza-3-indancarboxylic acid |
| 33 | | (3S)-3-Amino-7-cyclopropyl-6-[(1-naphthyl)methyl]-1-thia-3a-aza-4-indanone |
| 34 | | (2R, 3R)-7-Cyclopropyl-6-[(1-naphthyl)methyl]-4-oxo-2-phenyl-1-thia-3a-aza-3-indancarboxylic acid |
| 35 | | (2S, 3R)-7-Cyclopropyl-2-methoxy-6-[(1-naphthyl)methyl]-4-oxo-1-thia-3a-aza-3-indancarboxylic acid |

TABLE 1-continued

| Example Number | Chemical Structure | Compound name |
|---|---|---|
| 36 | | 7-Cyclopropyl-4-oxo-6-{[m-(trifluoromethyl)phenyl]methyl}-1-thia-3a-aza-3-indancarboxylic acid |

$^1$H NMR (400 MHz, DMSO-d6): δ = 13.37 (br s, 1H), 7.65-7.52 (m, 4H), 5.71 (s, 1H), 5.39 (dd, J = 1.8, 9.1 Hz, 1H), 4.16-4.04 (m, 2H), 3.78 (dd, J = 9.2, 11.9 Hz, 1H), 3.50 (dd, J = 1.8, 11.9 Hz, 1H), 1.45-1.36 (m, 1H), 0.95-0.83 (m, 2H), 0.68-0.59 (m, 1H), 0.57-0.48 (m, 1H) ppm. HRMS (ESI+) (m/z): [M + H]+ calcd. for C19H17F3NO3S, 396.0876; found, 396.0869

| 37 | | 2-{2-[1-(Hydroxymethyl)propylamino]ethylamino}butyl 7-cyclopropyl-6-[(1-naphthyl)methyl]-4-oxo-1-thia-3a-aza-3-indancarboxylate |

$^1$H NMR(400 MHz, DMSO-d6): δ = 7.78 (d, J =8.0 Hz, 1H), 7.74-7.64 (m, 2H), 7.60-7.53 (m, 1H), 7.41-7.33 (m, 2H), 7.24-7.18 (m, 1H), 6.09 (s, 1H), 5.52 (d, J = 8.4 Hz, 1H), 4.35-4.11 (m, 4H), 3.62 (d, J = 11.2 Hz, 1H), 3.48 (dd, J = 8.4 Hz, 1H), 3.39-3.13 (m, 3H), 2.95-2.70 (m, 5H), 1.66-1.50 (m, 4H), 1.37-1.06 (m, 7H), 0.77-0.56 (m, 4H) ppm.

| 38 | | {7-Cyclopropyl-6-[(1-naphthyl)methyl]-4-oxo-1-thia-3a-aza-3-indanyl}(2-isonicotinoylhydrazino)formaldehyde |

$^1$H NMR(400 MHz, CDCl3): δ = 8.48 (br s, 2H), 7.87-7.85 (m, 1H), 7.81-7.71 (m, 4H), 7.66-7.59 (m, 2H), 7.45-7.38 (m, 4H), 6.14 (s, 1H), 5.60 (d, J = 8.8 Hz, 1H), 4.13 (dd, J = 15.6, 49.2 Hz, 2H), 3.69 (d, J = 11.6 Hz, 1H), 3.55 (dd, J = 8.8, 11.6 Hz, 1H), 1.44-1.35 (m, 1H), 0.94-0.85 (m, 2H), 0.70-0.63 (m, 2H) ppm.

| 39 | | 7-Cyclopropyl-6-[(4-methoxy-1-naphthyl)methyl]-4-oxo-1-thia-3a-aza-3-indancarboxylic acid |

$^1$H NMR (400 MHz, DMSO-d6): δ = 13.35 (bs, 1H), 8.21 (d, 1H, J = 2 Hz), 7.79 (d, 1H, J = 1.2 Hz), 7.56-7.49 (m, 2H), 7.30 (d, 1H, J = 8.0 Hz), 6.97 (d, 1H, J = 8.0 Hz), 5.32 (dd, 1H, J = 1.6, 9.2 Hz), 5.23 (s, 1H), 4.34.39 (d, 1H, J = 17.2 Hz), 4.30 (d, 1H, J = 17.6 Hz), 3.98 (s, 3H), 3.79 (dd, 1H, J = 2.8, 9.0 Hz), 3.50 (dd, 1H), J = 1.6, 12 Hz), 1.76-1.70 (m, 1H), 0.98-0.86 (m, 2), 0.78-0.74 (m, 1H), 0.66-0.60 (m, 1H) ppm. HRMS (ESI+) (m/z): [M + Na]+ calcd. for C23H21NNaO4S, 430.1089; found, 430.1071

TABLE 1-continued

| Example Number | Chemical Structure | Compound name |
|---|---|---|
| 40 | | (3R)-7-(Dimethylamino)-6-[(1-naphthyl)methyl]-4-oxo-1-thia-3a-aza-3-indancarboxylic acid |

¹H NMR (400 MHz, Methanol-d4) δ 7.96-7.87 (m, 2H), 7.84 (d, J = 8.2 Hz, 1H), 7.57-7.46 (m, 3H), 7.40 (d, J = 6.9 Hz, 1H), 5.69 (s, 1H), 5.60 (d, J = 8.7 Hz, 1H), 4.45 (s, 2H), 3.92 (dd, J = 12.0, 8.8 Hz, 1H), 3.69 (d, J = 12.0 Hz, 1H), 2.70 (s, 6H).

| 41 | | (3R)-5-Bromo-7-cyclopropyl-6-[(1-naphthyl)methyl]-4-oxo-1-thia-3a-aza-3-indancarboxylic acid |

¹H NMR (400 MHz, DMSO-d6) δ = 13.65 (br s, 1H), 8.28 (d, J = 8.4 Hz, 1H), 7.99-7.95 (m, 1H), 7.81 (d, J = 8.2 Hz, 1H), 7.68-7.56 (m, 2H), 7.39 (t, J = 7.6 Hz, 1H), 6.77 (d, J = 7.1 Hz, 1H), 5.58 (dd, J = 1.4, 9.2 Hz, 1H), 4.74 (dd, J = 16.1, 51.0 Hz, 2H), 3.89 (dd, J = 9.2, 12.0 Hz, 1H), 3.59 (dd, J = 1.7, 12.0 Hz, 1H), 1.46-1.37 (m, 1H), 0.69-0.58 (m, 2H), 0.53-0.38 (m, 2H) ppm.

| 42 | | 7-Cyclopropyl-6-[(1-naphthyl)methyl]-1,1-dioxo-4-oxo-1-thia-3a-aza-3-indancarboxylic acid |

¹H NMR (400 MHz,CDCl3): δ = 13.82 (br s, 1H), 8.00-7.97 (m, 1H), 7.93-7.89 (m, 2H), 7.57-7.51 (m, 3H), 7.41 (d, J = 6.4 Hz, 1H), 5.73 (s, 1H), 5.33 (dd, J = 1.6, 8.8 Hz, 1H), 4.59 (ABq, 2H, J = 35 Hz), 4.16-4.04 (m, 2H), 1.89-1.82 (m, 1H), 1.24-1.19 (m, 1H), 1.04-0.94 (m, 2H), 0.82-0.73 (m, 1H) ppm. HRMS calc: [M + H+]: 410.1056; found: 410.1079

| 43 | | (3R)-7-Cyclopropyl-4-oxo-6-[(2,3-xylidino)methyl]-1-thia-3a-aza-3-indancarboxylic acid |

¹H NMR (600 MHz, MeOH-d4): δ = 6.82 (t, 1H, J = 7.8 Hz), 6.47 (d, 1H, J = 7.2 Hz), 6.23 (s, 1H), 6.7 (d, 1H, J = 8.4 Hz), 5.54 (d, 1H, J = 7.8), 4.48 (ABq, 2H, J = 13.1 Hz), 3.81 (dd, 1H, J = 9, 12 Hz), 3.59 (dd, 1H, J = 1.2, 12 Hz), 2.24 (s, 3H), 2.13 (s, 3H), 1.75-1.71 (m, 1H), 1.04-1.00 (m, 1H), 0.97-0.93 (m, 1H), 0.73-0.68 (m, 2H) ppm. HRMS calc. M + H +:371.1424; found; 317.1390

TABLE 1-continued

| Example Number | Chemical Structure | Compound name |
|---|---|---|
| 44 | | 7-Cyclopropyl-6-[(1-naphthyl)methy]-1-oxo-4-oxo-1-thia-3a-aza-3-indancarboxylic acid |

¹H NMR (400 MHz, MeOH-d4): δ = 7.93-7.83 (m, 3H), 7.52-7.46 (m, 3H), 7.39 (d, 1H, J = 6.4 Hz), 5.95 (s, 1H), 5.49 (bs, 1H), 4.69 (d, 1H, J = 18 Hz), 4.60 (d, 1H, J = 18 Hz), 3.91 (dd, 1H, J = 5.2, 13.6 Hz), 3.79 (dd, 1H, J = 7.6, 13.6 H), 2.03-1.96 (m, 1H), 1.22-1.17 (m, 2H), 1.12-1.08 (m, 1H), 0.96-0.95 (m, 1H) ppm. MS calc: [M + H +]: 394.1, found: 394.2

| | | |
|---|---|---|
| 45 | | (3R)-7-Ethoxy-6-[(1-naphthyl)methyl]-4-oxo-1-thia-3a-aza-3-indancarboxylic acid |

¹H NMR, 400 MHz, (DMSO) δ 1.27 (t, J = 7.0 Hz, 3H), 3.58 (dd, J = 1.8, 11.9 Hz, 1H), 3.82-4.0 (m, 3H), 4.29 (dd, J = 16.8, 25.7 Hz, 2H), 5.34 (dd, J = 1.7, 8.9 Hz, 1H), 5.36 (s, 1H), 7.43 (dd, J = 1.1, 7.0 Hz, 1H), 7.47-7.57 (m, 3H), 7.85-7.99 (m, 3H).

| | | |
|---|---|---|
| 46 | | (3R)-7-Cyclopropyl-2,2-dimethyl-6-[(1-naphthyl)methyl]-4-oxo-1-thia-3a-aza-3-indancarboxylic acid |

¹H NMR (400 MHz,CDCl3): δ = 13.50 (br s, 1H), 7.98-7.96 (m, 1H), 7.92-7.87 (m, 2H), 7.55-7.48 (m, 3H), 7.38 (d, J = 6.8 Hz, 1H), 5.22 (s, 1H), 4.80 (s, 1H), 4.49-4.40 (m, 2H), 1.73-1.67 (m, 1H), 1.58 (s, 3H), 1.53 (s, 3H), 0.96-0.82 (m, 2H), 0.73-0.60 (m, 2H) ppm. HRMS calc: [M + H +]: 406.1470; found: 406.1510

| | | |
|---|---|---|
| 47 | | (3R)-6-[(1-Naphthyl)methy]-4-oxo-7-(trifluoromethyl)-1-thia-3a-aza-3-indancarboxylic acid |

¹H NMR, 400 MHz, (DMSO) δ 3.62 (dd, J = 1.2, 11.9 Hz, 1H), 3.88 (dd, J = 9.2, 11.9 Hz, 1H), 4.38 (s, 2H), 5.40 (s, 1H), 5.46 (d, J = 9.2 Hz, 1H), 7.39-7.42 (m, 1H), 7.49-7.58 (m, 3H), 7.74-7.80 (m, 1H), 7.89-7.94 (m, 1H), 7.96-8.01 (m, 1H).

TABLE 1-continued

| Example Number | Chemical Structure | Compound name |
|---|---|---|
| 48 | | (3R)-7-Isobutoxy-6-[(1-naphthyl)methyl]-4-oxo-1-thia-3a-aza-3-indancarboxylic acid |

¹H NMR, 400 MHz, (DMSO) δ 0.92-0.96 (m, 6H), 1.88-1.99 (m, 1H), 3.52-3.61 (m, 2H), 3.68 (dd, J = 6.4, 8.6 Hz, 1H), 3.87 (dd, J = 8.9, 11.9 Hz, 1H), 4.29 (dd, J = 16.9, 23.5 Hz, 2H), 5.33 (dd, J = 1.5, 8.9 Hz, 1H), 5.36 (s, 1H), 7.41-7.44 (m, 1H), 7.48-7.57 (m, 3H), 7.86-7.98 (m, 3H).

| | | |
|---|---|---|
| 49 | | (3R)-7-Cyclopropyl-6-[(2-methoxy-1-naphthyl)methyl]-4-oxo-1-thia-3a-aza-3-indancarboxylic acid |

¹H NMR, 400 MHz, (DMSO-d6, 400 MHz): δ = 13.33 (bs, 1H), 7.97 (d, 1H, J = 8.8 Hz), 7.92 (dd, 1H, J = 1.2, 8.4 Hz), 7.69 (d, 1H, J = 8.4 Hz), 7.53 (d, 1H, J = 9.2 Hz), 7.47 (ddd, 1H, J = 1.2, 6.8, 8.5 Hz), 7.39-7.34 (m, 1H), 5.29 (dd, 1H, J = 1.6, 9.2 Hz), 4.94 (s, 1H), 4.42 (d, 1H, J = 18 Hz), 4.33 (d, 1H, J = 18 Hz) , 3.91 (s, 3H), 3.79 (dd, 1H, J = 2.8, 9.2 Hz), 3.49 (dd, 1H, J = 1.6, 11.6 Hz), 1.91-1.85 (m, 1H), 1.09-0.97 (m, 2H), 0.83-0.78 (m, 1H), 0.73-0.67 (m, 1H) ppm.

| | | |
|---|---|---|
| 50 | | (3R)-7-(Cyclopropylmethoxy)-6-[(1-naphthyl)methyl]-4-oxo-1-thia-3a-aza-3-indancarboxylic acid |

¹H NMR, 400 MHz, (DMSO) δ 0.24-0.30 (m, 2H), 0.51-0.57 (m, 2H), 1.11-1.24 (m, 1H), 3.57 (dd, J = 1.7, 11.9 Hz, 1H), 3.71 (dABq, J = 7.2, 14.5 Hz, 2H), 3.87 (dd, J = 8.9, 11.9 Hz, 1H), 4.31 (dd, J = 16.6, 28.4 Hz, 2H), 5.31-5.35 (m, 2H), 7.41-7.45(m, 1H), 7.47-7.57 (m, 3H), 7.85-7.99 (m, 3H).

| | | |
|---|---|---|
| 51 | | 7-Cyclopropyl-6-[(2-methyl-1-aza-2-bora-1H-naphth-5-yl)methyl]-4-oxo-1-thia-3a-aza-3-indancarboxylic acid |

TABLE 1-continued

| Example Number | Chemical Structure | Compound name |
|---|---|---|
| 52 | | 7-Cyclopropyl-6-[(2-methyl-1-aza-2-bora-1H-naphth-5-yloxy)methyl]-4-oxo-1-thia-3a-aza-3-indancarboxylic acid |
| 53 | | 7-Cyclopropyl-6-[(2-methyl-1-aza-2-bora-1H-naphth-8-yl)methyl]-4-oxo-1-thia-3a-aza-3-indancarboxylic acid |
| 54 | | 7-Cyclopropyl-6-[(2-methyl-1-aza-2-bora-1H-naphth-8-yloxy)methyl]-4-oxo-1-thia-3a-aza-3-indancarboxylic acid |
| 55 | SS197 | 1H-imidazol-1-ium 7-(benzo[d]oxazol-2-yl)-8-cyclopropyl-5-oxo-3,5-dihydro-2H-thiazolo[3,2-a]pyridine-3-carboxylate |
| 56 | PD 83 | 1H-imidazol-1-ium 8-cyclopropyl-7-(3-(naphthalen-1-yl)isoxazol-5-yl)-5-oxo-3,5-dihydro-2H-thiazolo[3,2-a]pyridine-3-carboxylate |

TABLE 1-continued

| Example Number | Chemical Structure | Compound name |
| --- | --- | --- |
| 57 | PD 90 | 1H-imidazol-1-ium 8-cyclopropyl-5-oxo-7-(3-(3-(trifluoromethyl)phenyl)isoxazol-5-yl)-3,5-dihydro-2H-thiazolo[3,2-a]pyridine-3-carboxylate |
| 58 | PD 103 | 1H-imidazol-1-ium 8-cyclopropyl-5-oxo-7-(3-(thiophen-2-yl)isoxazol-5-yl)-3,5-dihydro-2H-thiazolo[3,2-a]pyridine-3-carboxylate |
| 59 | PD 114 | 1H-imidazol-1-ium 8-cyclopropyl-5-oxo-7-(3-phenylisoxazol-5-yl)-3,5-dihydro-2H-thiazolo[3,2-a]pyridine-3-carboxylate |
| 60 | PD 118 | 1H-imidazol-1-ium 6-bromo-7-(naphthalen-1-ylmethyl)-5-oxo-8-(3-phenylisoxazol-5-yl)-3,5-dihydro-2H-thiazolo[3,2-a]pyridine-3-carboxylate |

TABLE 1-continued

| Example Number | Chemical Structure | Compound name |
|---|---|---|
| 61 | 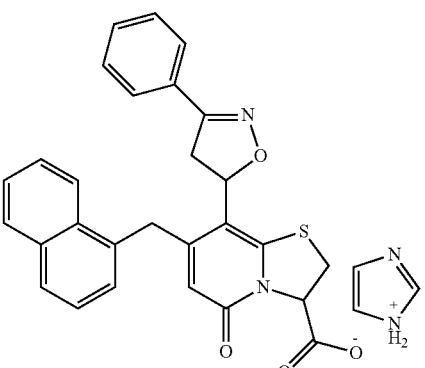<br>PD 147 | 1H-imidazol-1-ium 7-(naphthalen-1-ylmethyl)-5-oxo-8-(3-phenyl-4,5-dihydroisoxazol-5-yl)-3,5-dihydro-2H-thiazolo[3,2-a]pyridine-3-carboxylate |
| 62 | 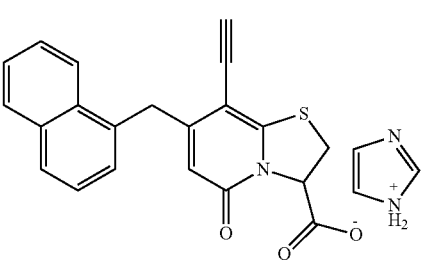<br>PD 125 | 1H-imidazol-1-ium 8-ethynyl-7-(naphthalen-1-ylmethyl)-5-oxo-3,5-dihydro-2H-thiazolo[3,2-a]pyridine-3-carboxylate |
| 63 | 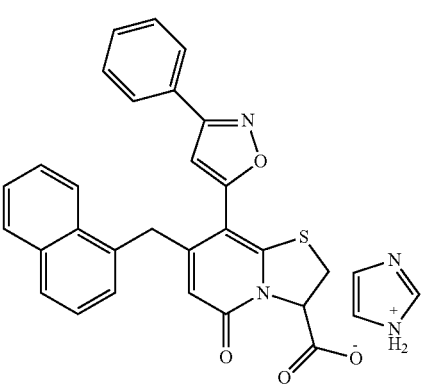<br>PD 124 | 1H-imidazol-1-ium 7-(naphthalen-1-ylmethyl)-5-oxo-8-(3-phenylisoxazol-5-yl)-3,5-dihydro-2H-thiazolo[3,2-a]pyridine-3-carboxylate |

TABLE 1-continued

| Example Number | Chemical Structure | Compound name |
|---|---|---|
| 64 | 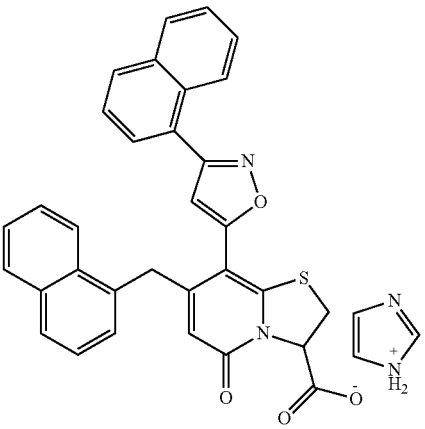<br>PD 148 | 1H-imidazol-1-ium 8-(3-(naphthalen-1-isoxazol-5-yl)-7-(naphthalen-1-ylmethyl)-5-oxo-3,5-dihydro-2H-thiazolo[3,2-a] pyridine-3-carboxylate |
| 65 | 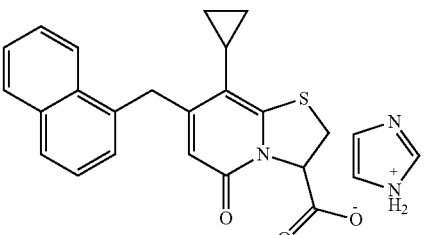<br>MH44 | 1H-imidazol-1-ium8-cyclopropyl-7-(naphthalen-1-ylmethyl)-5-oxo-3,5-dihydro-2H-thiazolo[3,2-a]pyridine-3-carboxylate |
| 66 | 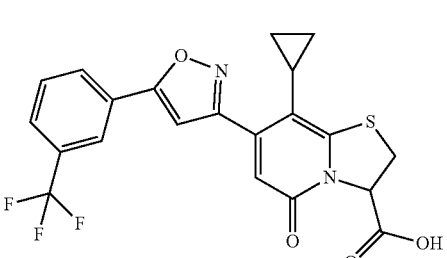 | 8-cyclopropyl-5-oxo-7-(5-(3-(trifluoromethyl)phenyl)isoxazol-3-yl)-2,3-dihydrothiazolo[3,2-a]pyridine-3-carboxylic acid |
| 67 | 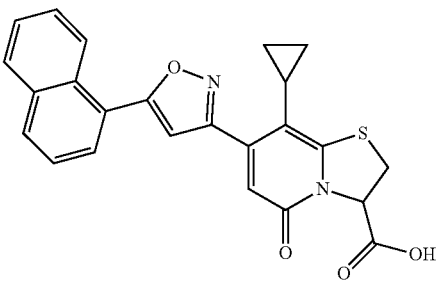 [SMILES: O=C(O)C1CSc2c(C3CC3)c(-c3cc(-c4cccc5ccccc45)on3)cc(=O)n21] | 8-cyclopropyl-7-(5-(naphthalen-1-yl) isoxazol-3-yl)-5-oxo-2,3-dihydrothiazolo[3,2-a]pyridine-3-carboxylic acid |

TABLE 1-continued $^1$H-NMR and and HRMS data

| Example Number | Chemical Structure | Compound name |
|---|---|---|
| 68 | 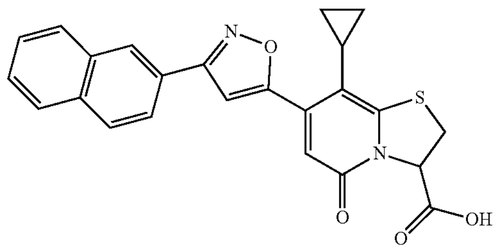 [SMILES: O=C(O)C1CSc2c(C3CC3)c(-c3cc(-c4ccc5ccccc5c4)no3)cc(=O)n21] | 8-cyclopropyl-7-(3-(naphthalen-2-yl)isoxazol-5-yl)-5-oxo-2,3-dihydrothiazolo[3,2-a]pyridine-3-carboxylic acid |
| 69 | 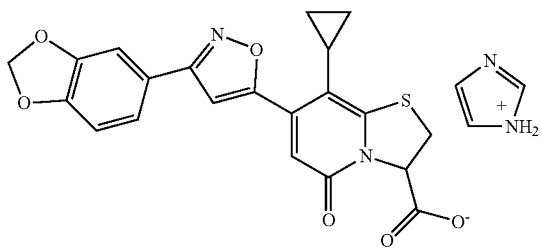 [SMILES: O=C([O-])C1CSc2c(C3CC3)c(-c3cc(-c4ccc5c(c4)OCO5)no3)cc(=O)n21 ; c1c[nH]cn1] | 1H-imidazol-1-ium 7-(3-(benzo[d][1,3]dioxol-5-yl(isoxazol-5-yl)-8-cyclopropyl-5-oxo-2,3-dihydrothiazolo[3,2-a]pyridine-3-carboxylate |
| 70 | 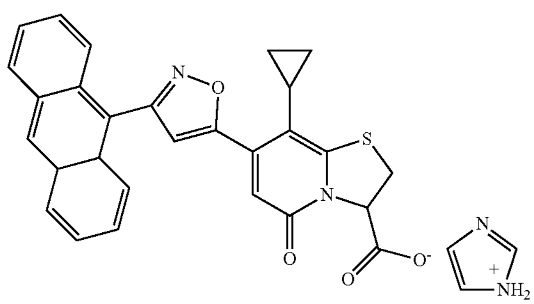 [SMILES: O=C([O-])C1CSc2c(C3CC3)c(-c3cc(C4=c5ccccc5=CC5C=CC=CC45)no3)cc(=O)n21 ; c1c[nH]cn1] | 1H-imidazol-1-ium 7-(3-(anthracen-9-yl)isoxazol-5-yl)-8-cyclopropyl-5-oxo-2,3-dihydrothiazolo[3,2-a]pyridine-3-carboxylate |
| 71 | 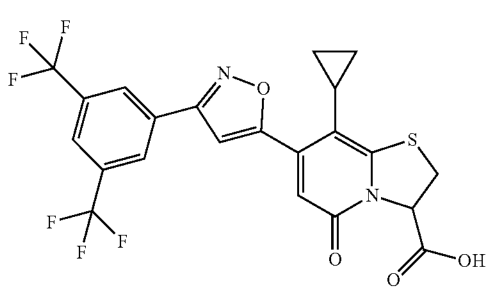 [SMILES: O=C(O)C1CSc2c(C3CC3)c(-c3cc(-c4cc(C(F)(F)F)cc(C(F)(F)F)c4)no3)cc(=O)n21] | 7-(3-(3,5-bis(trifluoromethyl)phenyl)isoxazol-5-yl)-8-cyclopropyl-5-oxo-2,3-dihydrothiazolo[3,2-a]pyridine-3-carboxylic acid |
| 72 | 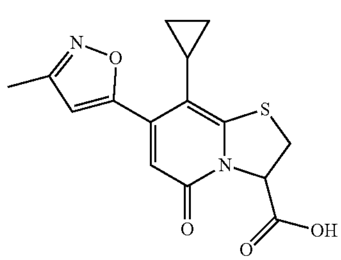 [SMILES: Cc1cc(-c2cc(=O)n3c(c2C2CC2)SCC3C(=O)O)on1] | 8-cyclopropyl-7-(3-methylisoxazol-5-yl)-5-oxo-2,3-dihydrothiazolo[3,2-a]pyridine-3-carboxylic acid |

TABLE 1-continued

| Example Number | Chemical Structure | Compound name / ¹H-NMR and HRMS data |
|---|---|---|
| 73 | | 7-(3-(tert-butylamino)imidazo[1,2-a]pyridin-2-yl)-8-cyclopropyl-5-oxo-2,3-dihydrothiazolo[3,2-a]pyridine-3-carboxylic acid |
| 74 | | 7-(3-(benzylamino)imidazo[1,2-a]pyridin-2-yl)-8-cyclopropyl-5-oxo-2,3-dihydrothiazolo[3,2-a]pyridine-3-carboxylic acid<br>¹H NMR (400 MHz, CD₃OD) δ 8.45 (d, J = 6.8 Hz, 1H), 7.62 (d, J = 8.8 Hz, 1H), 7.54 (t, J = 8.4 Hz, 1H), 7.19-7.11 (m, 6H), 6.22 (s, 1H), 5.61 (dd, J = 4.2, 1.6 Hz, 1H), 4.20 (q, J = 18 Hz, 2H), 3.86 (dd, J = 11.8, 8.8 Hz, 1H), 3.66 (dd, J = 11.8, 1.6 Hz, 1H), 1.77-1.70 (m, 1H), 0.50-0.34 (m, 2H), 0.03--0.02 (m, 1H), -0.23--0.30 (m, 1H).<br>¹³C NMR (100 MHz, CD₃OD) δ 170.70, 163.67, 161.38, 151.94, 145.70, 138.97, 138.84, 128.64, 128.44, 128.09 (2C), 127.68 (2C), 127.11, 125.91, 123.68, 115.10, 114.10, 113.85, 64.96, 50.11, 31.96, 11.00, 6.97, 6.62. |
| 75 | | 8-cyclopropyl-7-(3-((naphthalen-1-ylmethyl)amino)imidazo[1,2-a]pyridin-2-yl)-5-oxo-2,3-dihydrothiazolo[3,2-a]pyridine-3-carboxylic acid<br>¹H NMR (600 MHz, CD₃OD) δ 8.66 (d, J = 6.6 Hz, 1H), 8.25 (d, J = 8.4 Hz, 1H), 7.94 (d, J = 7.8 Hz, 1H), 7.82 (m, 2H), 7.73 (t, J = 8.4 Hz, 1H), 7.64-7.58 (m, 2H), 7.37-7.31 (m, 2H), 7.14 (d, J = 7.2 Hz, 1H), 6.01 (s, 1H), 5.59 (dd, J = 9.0, 1.2 Hz, 1H), 4.93 (d, J = 12 Hz, 1H), 4.67 (d, J = 12 Hz, 1H), 3.92 (dd, J = 11.4, 9 Hz, 1H), 3.74 (dd, J = 11.4, 1.2 Hz, 1H), 1.84-1.82 (m, 1H), 0.59-0.51 (m, 2H), 0.02--0.015 (m, 1H), -0.10-0.14 (m, 1H).<br>¹³C NMR (150 MHz, CD₃OD) δ 170.76, 163.69, 160.84, 151.57, 144.66, 139.07, 133.93, 133.79, 131.56, 128.88, 128.49, 128.11, 127.84, 126.72, 125.78, 125.31, 124.84, 123.81, 123.11, 114.98, 114.36, 114.15, 113.14, 64.83, 48.19, 31.89, 10.81, 6.66, 6.51. |
| 76 | | 8-cyclopropyl-5-oxo-7-(3-((3-(trifluoromethyl)benzyl)amino)imidazo[1,2-a]pyridin-2-yl)-2,3-dihydrothiazolo[3,2-a]pyridine-3-carboxylic acid |

TABLE 1-continued

| Example Number | Chemical Structure | Compound name and ¹H-NMR and HRMS data |
|---|---|---|
| 77 | | 7-(3-(tert-butylamino)-6-chloroimidazo[1,2-a]pyridin-2-yl)-8-cyclopropyl-5-oxo-2,3-dihydrothiazolo[3,2-a]pyridine-3-carboxylic acid<br>$^1$H NMR (400 MHz, CD$_3$OD) δ 8.28 (d, J = 1.2 Hz, 1H), 7.32 (dd, J = 4.6, 0.4 Hz, 1H), 7.15 (dd, J = 4.0, 2.0 Hz, 1H), 6.29 (s, 1H), 5.48 (dd, J = 4.4, 1.6 Hz, 1H), 3.71 (dd, J = 12, 8.8 Hz, 1H), 3.47 (dd, J = 12, 1.6 Hz, 1H), 1.83-1.75 (m, 1H), 0.85 (2, 9H), 0.44-0.39 (m, 2H), 0.04--0.03 (m, 2H).<br>$^{13}$C NMR(100 MHz, CD$_3$OD) δ 169.68, 161.75, 151.65, 149.73, 139.85, 136, 79, 126.85, 126.58, 121.70, 120.76, 116.68, 114.9, 114.2, 64.07, 55.59, 31.44, 29.16 (3H), 11.43, 7.07, 6.95. |
| 78 | | 7-(6-chloro-3-((naphthalen-1-ylmethyl)amino)imidazo[1,2-a]pyridin-2-yl)-8-cyclopropyl-5-oxo-2,3-dihydrothiazolo[3,2-a]pyridine-3-carboxylic acid |
| 79 | | 7-(3-(benzylamino)-6-chloroimidazo[1,2-a]pyridin-2-yl)-8-cyclopropyl-5-oxo-2,3-dihydrothiazolo[3,2-a]pyridine-3-carboxylic acid |
| 80 | | 7-(6-chloro-3-((3-(trifluoromethyl)benzyl)amino)imidazo[1,2-a]pyridin-2-yl)-8-cyclopropyl-5-oxo-2,3-dihydrothiazolo[3,2-a]pyridine-3-carboxylic acid |

TABLE 1-continued

| Example Number | Chemical Structure | Compound name |
|---|---|---|
| 81 | 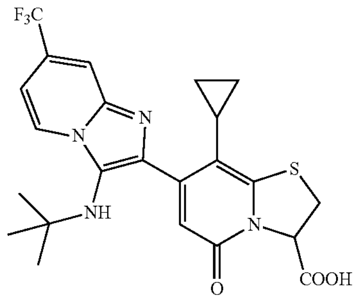 [SMILES: CC(C)(C)Nc1c(-c2cc(=O)n3c(c2C2CC2)SCC3C(=O)O)nc2cc(C(F)(F)F)ccn12] | 7-(3-(tert-butylamino)-7-(trifluoromethyl)imidazo[1,2-a]pyridin-2-yl)-8-cyclopropyl-5-oxo-2,3-dihydrothiazolo[3,2-a]pyridine-3-carboxylic acid |
| 82 | 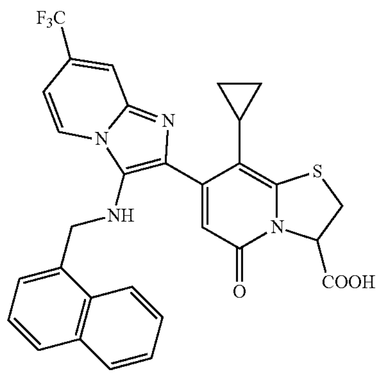 [SMILES: O=C(O)C1CSc2c(C3CC3)c(-c3nc4cc(C(F)(F)F)ccn4c3NCc3cccc4ccccc34)cc(=O)n21] | 8-cyclopropyl-7-(3-((naphthalen-1-ylmethyl)amino)-7-(trifluoromethyl)imidazo[1,2-a]pyridin-2-yl)-5-oxo-2,3-dihydrothiazolo[3,2-a]pyridine-3-carboxylic acid<br>$^1$H NMR (600 MHz, CD$_3$OD) δ 8.58 (d, J = 7.2 Hz, 1H), 8.20 (d, J = 8.4 Hz, 1H), 7.91-7.90 (m, 2H), 7.79 (d, J = 7.8 Hz, 1H), 7.60-7.54 (m, 2H), 7.29 (t, J = 7.8 Hz, 1H), 7.25 (d, J = 7.2 Hz, 1H), 7.09 (d, J = 7.2 Hz, 1H), 6.00 (s, 1H), 5.63 (d, J = 8.4 Hz, 1H), 4.90 (d, J = 12.6 Hz, 1H), 4.61 (d, J = 14.4 Hz, 1H), 3.92 (dd, J = 11.8, 9.2 Hz, 1H), 3.70 (d, J = 12 Hz, 1H), 1.84-1.79 (m, 1H), 0.57-0.52 (m, 1H), 0.47-0.43 (m, 1H), 0.02--0.01 (m, 1H), -0.17-0.21 (m, 1H).<br>$^{13}$C NMR (150 MHz, CD$_3$OD) δ 169.51, 161.06, 150.82, 148.05, 138.81, 134.81, 134.17, 133.82, 131.59, 128.93, 128.42, 128.13, 126.63, 126.11, 125.89, 125.77, 125.25, 124.84, 124.44, 124.18, 123.05, 122.64, 114.80, 114.19, 114.16, 113.83, 107.71, 107.69, 63.70, 48.29, 31.35, 11.04, 6.65 (2C). |
| 83 | 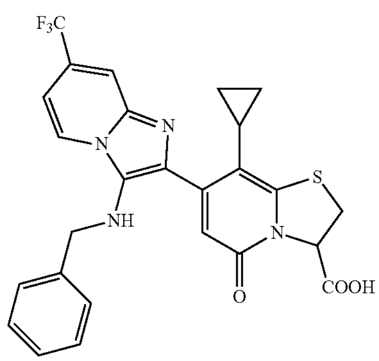 [SMILES: O=C(O)C1CSc2c(C3CC3)c(-c3nc4cc(C(F)(F)F)ccn4c3NCc3ccccc3)cc(=O)n21] | 7-(3-(benzylamino)-7-(trifluoromethyl)imidazo[1,2-a]pyridin-2-yl)-8-cyclopropyl-5-oxo-2,3-dihydrothiazolo[3,2-a]pyridine-3-carboxylic acid |
| 84 | 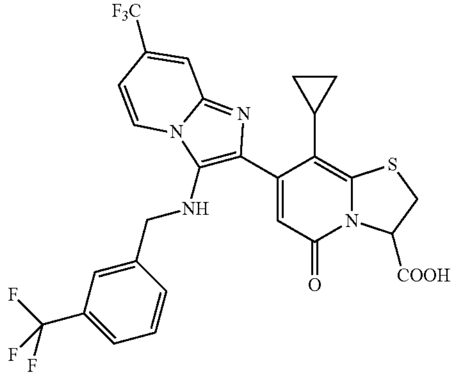 [SMILES: O=C(O)C1CSc2c(C3CC3)c(-c3nc4cc(C(F)(F)F)ccn4c3NCc3cccc(C(F)(F)F)c3)cc(=O)n21] | 8-cyclopropyl-5-oxo-7-(7-(trifluoromethyl)-3-((3-(trifluoromethyl)benzyl)amino)imidazo[1,2-a]pyridin-2-yl)-2,3-dihydrothiazolo[3,2-a]pyridine-3-carboxylic acid |

TABLE 1-continued

| Example | | |
|---|---|---|
| | ¹H-NMR and and HRMS data | |
| Number | Chemical Structure | Compound name |
| 85 | | 7-(3-(tert-butylamino)-7-methoxyimidazo[1,2-a]pyridin-2-yl)-8-cyclopropyl-5-oxo-2,3-dihydrothiazolo[3,2-a]pyridine-3-carboxylic acid |
| 86 | | 8-cyclopropyl-7-(7-methoxy-3-((naphthalen-1-ylmethyl)amino)imidazo[1,2-a]pyridin-2-yl)-5-oxo-2,3-dihydrothiazolo[3,2-a]pyridine-3-carboxylic acid |
| 87 | | 7-(3-(benzylamino)-7-methoxyimidazo[1,2-a]pyridin-2-yl)-8-cyclopropyl-5-oxo-2,3-dihydrothiazolo[3,2-a]pyridine-3-carboxylic acid |
| 88 | | 8-cyclopropyl-7-(7-methoxy-3-((3-(trifluoromethyl)benzyl)amino)imidazo[1,2-a]pyridin-2-yl)-5-oxo-2,3-dihydrothiazolo[3,2-a]pyridine-3-carboxylic acid |

All compounds in Table 2 have been synthesized except for the compounds of Examples 71-73, 76, 78-81 and 83. Examples 71-73, 76, 78-81 and 83-88 are prophetic examples.

Intermediates

Benzyl (4R)-2-(cyclopropylmethyl)Δ²-1,3-thiazoline-4-carboxylate

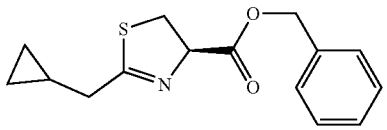 [SMILES: O=C(OCc1ccccc1)[C@@H]1CSC(CC2CC2)=N1]

Et₃N (0.28 mL, 206 mg, 2.0 mmol) was added, at RT, to a solution of (R)-Cysteine benzyl ester hydrochloride (506 mg, 2.0 mmol) and 2-cyclopropyl-1-ethoxy-1-ethanimine hydrochloride (368 mg, 2,2 mmol) in dry CH₂Cl₂ (20 mL). Precipitation started within minutes after addition of Et₃N. The reaction mixture was stirred at RT for 18 h and diluted with CH₂Cl₂. NaHCO₃ (sat aq, 10 mL) was added and the phases were separated. The aqueous phase was extracted with CH₂Cl₂ and the combined organic phases were dried (Na₂SO₄), filtered and concentrated in vacuo to afford 587 mg pale yellow oil. Purification by column chromatography (Biotage 50 g, 10-30% EtOAc in heptane) afforded 324 mg (58%) of the product as a pale yellow oil. ¹H NMR (600 MHz, CHCl₃): δ 7.35 (m, 5H), 5.24 (dd, J=12.6, 22.8 Hz, 2H), 5.10 (m, 1H), 3.53 (m, 2H), 2.46 (m, 2H), 0.98 (m, 1H), 0.57 (m, 2H), 0.22 (m, 2H).

5-{1-Hydroxy-2-[m-(trifluoromethyl)phenyl]ethylidene}-2,2-dimethyl-1,3-dioxane-4,6-dione

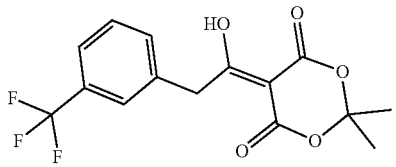 [SMILES: CC1(C)OC(=O)C(=C(O)Cc2cccc(C(F)(F)F)c2)C(=O)O1]

3-(Trifluoromethyl)phenylacetic acid (1.22 g, 6.0 mmol), Meldrum's acid (908 mg, 6.3 mmol) and DMAP (770 mg, 6.3 mmol) was dissolved in CH₂Cl₂ (20 mL) and cooled to 0° C. DCC (1 M in CH₂Cl₂, 7.8 mL, 7.8 mmol) was added drop-wise to the cooled solution that was stirred at 0° C. for 2 h and then over night at RT. KHSO₄ (6% aq. 12 mL) was added and the resulting precipitate was filtered off. The filtrate was washed with KHSO₄ (6% aq. 5×20 mL), H₂O (20 mL), brine (20 mL), dried (Na₂SO₄) and concentrated in vacuo. The afforded pink solid as suspended in CH₂Cl₂, the suspension as filtered and concentrated in vacuo to afford 2.03 g of a dark purple solid. This was the titled product, although not 100% pure. However, the purity was good enough to continue with.

¹H NMR (400 MHz, CHCl₃): δ 15.37 (br s, 1H), 7.67-7.62 (m, 1H), 7.61-7.53 (m, 2H), 7.48-7.42 (m, 1H), 4.48 (s, 2H), 1.73 (s, 6H)

Benzyl (3R)-7-cyclopropyl-4-oxo-6-{[m-(trifluoromethyl)phenyl]methyl}-1-thia-3a-aza-3-indancarboxylate

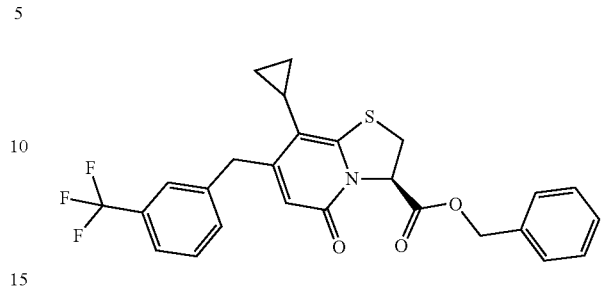

TFA (84 μL, 0.11 mmol) was added to a solution of Benzyl (4R)-2-(cyclopropylmethyl)Δ²-1,3-thiazoline-4-carboxylate (151 mg, 0.55 mmol) and 5-{1-Hydroxy-2-[m-(trifluoromethyl)phenyl]ethylidene}-2,2-dimethyl-1,3-dioxane-4,6-dione (543 mg, 1.65 mmol) in DCE (15 mL). Heated by MW at 120° C. for 2 min 30 sec. The reaction mixture was cooled to RT, diluted with CH₂Cl₂ (40 mL) and NaHCO₃ (sat aq, 5 mL) and H₂O (5 mL) were added. The phases were separated and the aqueous phase extracted with CH₂Cl₂ (3×15 mL). The combined organic phases were dried (Na₂SO₄) and concentrated in vacuo to afford 586 mg brown oil. Two consecutive purifications by column chromatography (first Biotage 50 g, 30-85% EtOAc in heptane and then 10 g Biotage) gave 69 mg (26%) of the product as pale yellow amorphous solid. ¹H NMR (600 MHz, CHCl₃): δ 7.49 (m, 1H), 7.45 (m, 1H), 7.40 (m, 1H), 7.34-7.29 (m, 6H), 5.99 (s, 1H), 5.64 (dd, 1.8, 8.4 Hz, 1H), 5.22 (dd, 12, 19 Hz, 2H), 4.07 (d, 15.6 Hz, 1H), 3.98 (d, 16 Hz, 1H), 3.63 (dd, 9.0, 12.0 Hz, 1H), 3.47 (dd, 2, 12 Hz, 1H), 1.36 (m, 1H), 0.92 (m, 1H), 0.85 (m, 1H), 0.62 (m, 2H) ppm.

Methyl (3R)-7-cyclopropyl-4-oxo-6-{[m-(trifluoromethyl)phenyl]methyl}-1-thia-3a-aza-3-indancarboxylate

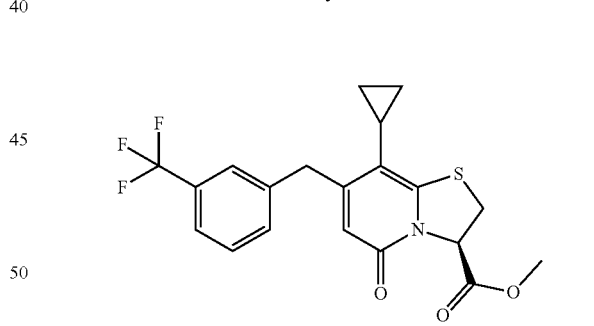

¹H NMR (400 MHz, CHCl₃): δ 7.48-7.52 (m, 1H), 7.35-7.46 (m, 3H), 5.99-6.01 (m, 1H), 5.61 (dd, J=2.3, 8.6 Hz, 1H), 4.09 (d, J=16.0 Hz, 1H), 3.99 (d, J=16.0 Hz, 1H), 3.80 (s, 3H), 3.66 (dd, J=8.6, 11.6 Hz, 1H), 3.50 (dd, J=2.3, 11.6 Hz, 1H), 1.33-1.42 (m, 1H), 0.83-0.97 (m, 2H), 0.60-0.70 (m, 2H).

Biology

Treatment of *Mycobacterium tuberculosis* Bacteria with Q203 in the Absence or Presence of the Compound (3R)-7-Cyclopropyl-6-[(1-naphthyl)methyl]-4-oxo-1-thia-3a-aza-3-indancarboxylic acid, i.e. the Compound of Example 1

For the experiment below, Q203 was provided by Examine Ltd, New Jersey, item number Z2235679010

*Mycobacterium tuberculosis* Erdman was inoculated into 40 mL 7H9 liquid media and grown 4 days at 37° C. in 5% $CO_2$ to $OD\lambda_{600}$=0.454 (measured by spectrometer). It was back-diluted to OD=0.16 in Sauton's media (0.5 g/L $KH_2PO_4$, 0.5 g/L $MgSO_4$, 4 g/L L-asparagine, 60 ml glycerol, 0.05 g/L ferric ammonium citrate, 2.0 g/L citric acid, 0.1 mL/L 1% $ZnSO_4$, 0.05% Tween 80, pH 7.0) by spinning down some of the culture and re-suspending in 50 mL of Sauton's media. After 3 days, the culture had reached an OD=0.547, and was backdiluted to $OD\lambda_{600}$=0.1 in Sauton's media and split into small bottles each containing 10 mL of liquid culture. Each experiment was done in duplicate. The cultures were treated with DMSO, Example 1 (25 μM), Q203 (0.4 μM), or Q203+Example 1 (0.4 μM+25 μM), respectively. The cultures were sampled every 3 days by spotting 5 μl of 10 fold dilutions on agar plates to count colony forming units (CFU). The $OD\lambda_{600}$ was measured at the beginning and end of the experiment. The CFU count is illustrated in FIG. 3*a* and the $OD\lambda_{600}$ at day zero and day 15 is illustrated in FIG. 5*b*. FIG. 3*a* shows that the treatment with Q203+Example 1 decreases the CFU/mL of *Mycobacterium tuberculosis* bacteria compared to the DMSO control, the compound of Example 1 and Q203. This decrease in CFU/mL is visible from about day 5 and increases over time, being most pronounces at the measurement on the last day of the experiment (day 15).

FIG. 3*b* shows that both Example 1 and Q203 decrease the $OD\lambda_{600}$ value considerably compared to the DMSO control. FIG. 3*b* also confirms that a synergistic effect is achievable when treating with Q203+ Example 1, when comparing to treatments Q203 and Example 1 alone.

It will be appreciated that the compound of Example 1 may be denominated (3R)-7-Cyclopropyl-6-[(1-naphthyl)methyl]-4-oxo-1-thia-3a-aza-3-indancarboxylic acid.

$IC_{50}$ values for the compounds of Examples 55-65

The $IC_{50}$ value was measured for the compounds 55-65. The measurement was made in accordance with the Microplate Alamar Blue Assay (MABA) as described by Franzblau, S. G. et al in *Tuberculosis* (*Edinb*). 92, 453-88 (2012: The MABA utilizes the dye resazurin, which is dark blue and nonfluorescent in its oxidized form but becomes pink and fluorescent when reduced to resorufin as a result of cellular metabolism. The MABA is commonly used to evaluate the efficacy of compounds in restraining Mtb growth, but also serves as an assay for aerobic respiration. The degree of the color change was monitored and quantified, and performing this assay with a range of compound concentrations allowed for calculating $IC_{50}$ values for compounds. The $IC_{50}$ value is defined as the concentration of the compound that inhibits the MABA color change by 50%.

TABLE 2

| Example number | Compound structure | $IC_{50}$ |
|---|---|---|
| 55 |  | 39.07 |
| 56 |  | 2.53 |
| 57 |  | 2.53 |

TABLE 2-continued
| Example number | Compound structure | IC$_{50}$ |
|---|---|---|
| 58 | 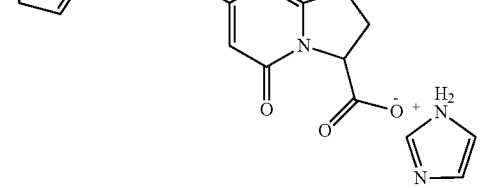 | 28.86 |
| 59 | 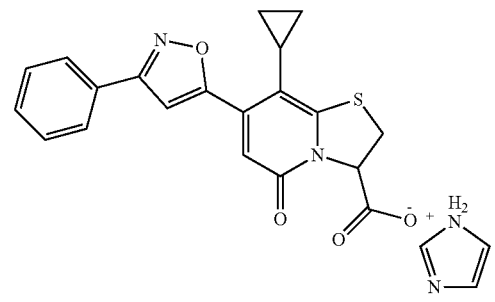 | 15.6 |
| 60 | 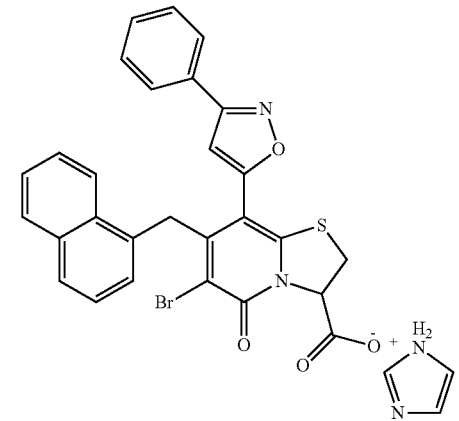 | 4.51 |
| 61 | 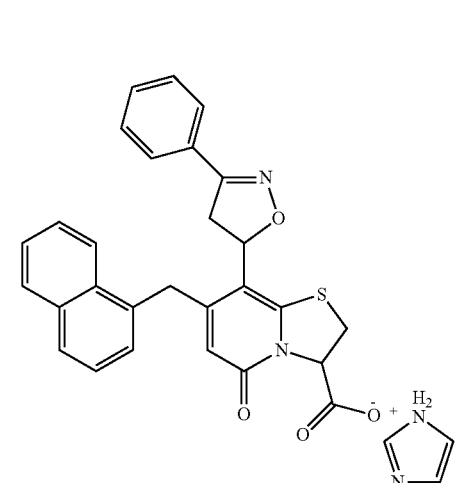 | 82.7 |

TABLE 2-continued

| Example number | Compound structure | IC$_{50}$ |
|---|---|---|
| 62 | 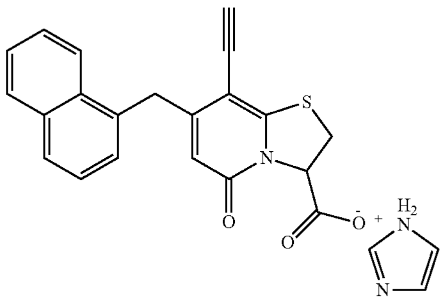 | 53.5 |
| 63 | 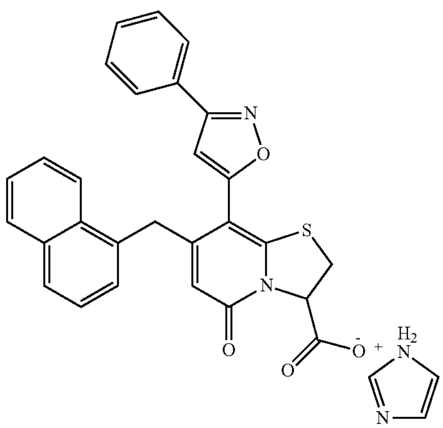 | 12.7 |
| 64 | 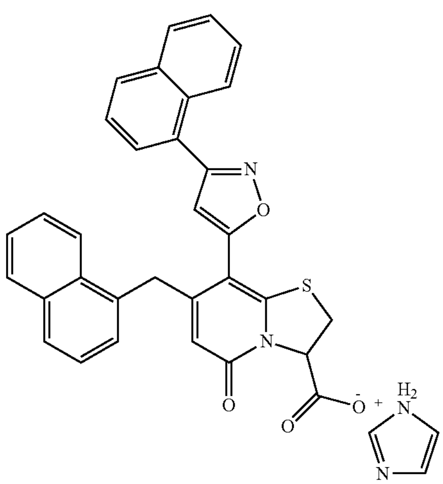 | 14.42 |
| 65 | 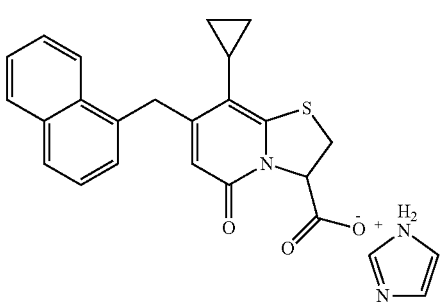 | 8.47 |

The invention claimed is:
1. A composition comprising:
(i) a compound of Formula I:

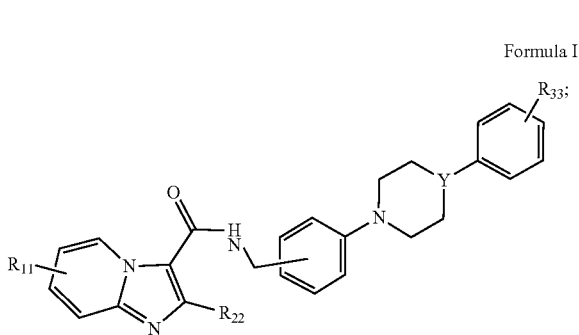

Formula I or a pharmaceutically acceptable salt thereof,
wherein:
$R_{11}$ is selected from the group consisting of F, Cl, Br, I, methyl, methoxy, CN, $CF_3$ and $OCF_3$,
$R_{22}$ is $C_1$-$C_4$ alkyl,
Y is CH or N,
$R_{33}$ is selected from the group consisting of:
a) F, Cl, Br, I, methyl, methoxy, CN, $CF_3$ and $OCF_3$,
b) C(O)OMe,
c) C(O)OH, and
d) $CH_2OH$; and
(ii) a compound of Formula II

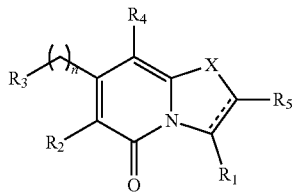

II or a pharmaceutically acceptable salt thereof,
wherein
$R_1$ is selected from the group consisting of:
a) C(O)OH,
b) tetrazolyl,
c) $CH_2OH$,
d) $C(O)NR_{6a}R_{6b}$,
e) $C(O)NHSO_2R_7$,
f) $C(O)OR_8$,
g) $NH_2$,
h) H,
i)

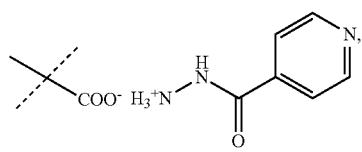

j)

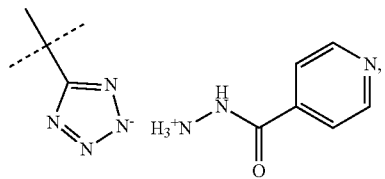

k)

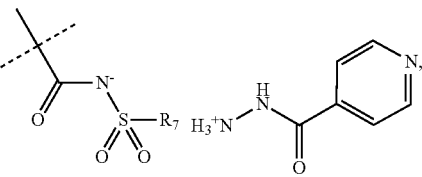

and
l) imidazole carboxylate,
$R_2$ is selected from the group consisting of:
a) H,
b) Cl, F, Br or I,
c) $CH_2OH$,
d) $C_1$-$C_4$alkyl, and
e) $NY_1Y_2$,
$R_3$ is selected from the group consisting of:
a) 1-naphthyl, 2-naphthyl or 1-naphthyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl
d) 2-(3-methyl)phenylmethylene,
e) benzothiophen-2-yl
f) H,
g) $C_1$-$C_4$alkyl,
h) 2-methyl-1-aza-2-bora-1H-naphth-5-yloxy,
i) 2-methyl-1-aza-2-bora-1H-naphth-5-yl,
j) isoxazol-5-yl optionally substituted with methyl, 1-naphthyl, 2-naphthyl, 1-anthryl, m-trifluoromethylphenyl, 3,5-ditrifluoromethylphenyl, 3,4-methylenedioxyphenyl, thiophene or phenyl,
k) isoxazol-3-yl substituted with m-trifluoromethylphenyl or 1-naphthyl,
l) benzoxazole-2-yl, and m)

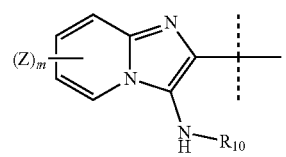

$R_4$ is selected from the group consisting of:
a) $C_1$-$C_4$alkyl substituted by 0, 1, 2, 3 or 4 fluoro,
b) $C_3$-$C_6$cycloalkyl,
c) $C_1$-$C_4$alkoxy substituted by 0, 1, 2, 3 or 4 fluoro, d) $C_3$-$C_6$cycloalkoxy,
e) a 3-, 4-, 5- or 6-membered heterocycle, substituted with 0 or 1 substituent selected from the group consisting of phenyl and 1-naphthyl,
f) N-methyl 3-indolyl,
g) $NR_{9a}R_{9b}$, and
h) $C_2$-$C_4$alkynyl, $R_5$ is selected from the group consisting of:
a) H,
b) phenyl substituted with 0, 1, 2 or 3 methyl group(s),
c) benzyl,
d) thienyl,
e) $C_1$-$C_4$alkoxy, and
f) a 3-, 4-, 5- or 6-membered heterocycle, and in the above definitions:
$R_{6a}$ is selected from the group consisting of H and $C_1$-$C_4$alkyl,
$R_{6b}$ is selected from the group consisting of H, $C_1$-$C_4$alkyl, $C_1$-$C_4$alkoxy and isonicotinoylamino;
$R_7$ is $C_1$-$C_4$alkyl or phenyl,
$R_8$ represents 2-{2-[1-(hydroxymethyl)propylamino]ethylamino}butyl),
$R_{9a}$ represents $C_1$-$C_4$alkyl,
$R_{9b}$ represents $C_1$-$C_4$alkyl,
$R_{10}$ represents H; $C_1$-C4alkyl substituted with 0, 1, 2 or 3 F; benzyl substituted with 0 or 1 trifluoromehtyl; or naphtalen-1-yl-methylene,
$Y_1$ and $Y_2$ each independently represents hydrogen, methyl, $CH_3S(O)_2$ or $C(O)CH_3$, or
$Y_1$ and $Y_2$ together form $CH_2CH_2CH_2CH_2$ or $CH_2CH_2CH_2CH_2CH_2$,
m is 0 or 1,
n is 0 or 1,
X is S, SO or $SO_2$, and
Z represents $C_1$-$C_4$alkyl substituted with 0, 1, 2 or 3 F; $C_1$-$C_4$alkoxy substituted with 0, 1, 2 or 3 F; or a halogen selected from Cl, F, Br or I.

2. The composition according to claim 1, wherein the compound of Formula II is a compound of Formula IIa or Formula IIb:

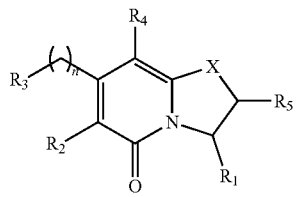

Formula IIa

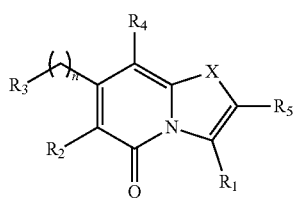

Formula IIb or a pharmaceutically acceptable salt thereof.

3. The composition according to claim 1, wherein X is S or SO.

4. The composition according to claim 1, wherein $R_1$ is C(O)OH, C(O)NHSO$_2R_7$, or tetrazolyl.

5. The composition according to claim 1, wherein $R_2$ is H.

6. The composition according to claim 1, wherein $R_3$ is selected from the group consisting of:
a) 1-naphthyl, 2-naphthyl or 1-naphthyloxy, each independently substituted with 0, 1, 2 or 3 substituents selected from the group consisting of methyl, fluoro, chloro, cyano and methoxy, and
b) phenyl substituted with 0,1, 2 or 3 substituents independently selected from the group consisting of methyl, fluoro, chloro, cyano and trifluoromethyl.

7. The composition according to claim 1, wherein $R_4$ is cyclopropyl.

8. The composition according claim 1, wherein $R_5$ is H.

9. The composition according to claim 1, wherein the compound of Formula II is:
(3R)-7-Cyclopropyl-6-[(1-naphthyl)methyl]-4-oxo-1-thia-3a-aza-3-indancarboxylic acid,
(3R)-7-Cyclopropyl-4-oxo-6-{(7-thiabicyclo[4.3.0]nona-1,3,5,8-tetraen-8-yl)methyl}-1-thia-3a-aza-3-indancarboxylic acid,
(3R)-7-Cyclopropyl-6-[(4-fluoro-1-naphthyl)methyl]-4-oxo-1-thia-3a-aza-3-indancarboxylic acid,
(3R)-7-Cyclopropyl-6-[(4-methyl-1-naphthyl)methyl]-4-oxo-1-thia-3a-aza-3-indancarboxylic acid,
(3 S)-7-Cyclopropyl-6-[(1-naphthyl)methyl]-4-oxo-1-thia-3a-aza-3-indancarboxylic acid,
5-Cyclopropyl-4-[(1-naphthyl)methyl]-2-oxo-8-(3-thienyl)-7-thia-1-azabicyclo[4.3.0]nona-3,5,8-triene-9-carboxylic acid,
(3R)-7-Cyclopropyl-6-[(1-naphthyloxy)methyl]-4-oxo-1-thia-3a-aza-3-indancarboxylic acid,
(3R)-7-Cyclopropyl-6-[(2-fluoro-5-methyl-phenyl)methyl]-4-oxo-1-thia-3a-aza-3-indancarboxylic acid,
(3R)-7-Cyclopropyl-4-oxo-6-[(2,3-xylyl)methyl]-1-thia-3a-aza-3-indancarboxylic acid,
(3R)-7-Methyl-6-[(1-naphthyl)methyl]-4-oxo-1-thia-3a-aza-3-indancarboxylic acid,
(N-Methylmethoxyamino){(3R)-7-cyclopropyl-6-[(1-naphthyl)methyl]-4-oxo-1-thia-3a-aza-3-indanyl}formaldehyde,
(3R)-7-Cyclopropyl-6-[(1-naphthyl)methyl]-3-(1H-1,2,3,4-tetrazol-5-yl)-1-thia-3a-aza-4-indanone,
5-Cyclopropyl-4-[(1-naphthyl)methyl]-2-oxo-8-phenyl-7-thia-1-azabicyclo[4.3.0]nona-3,5,8-triene-9-carboxylic acid,
5-Cyclopropyl-4-[(1-naphthyl)methyl]-2-oxo-8-(m-tolyl)-7-thia-1-azabicyclo[4.3.0]nona-3,5,8-triene-9-carboxylic acid,
(3R)-7-Cyclopropyl-6-[(2-naphthyl)methyl]-4-oxo-1-thia-3a-aza-3-indancarboxylic acid,
(3R)-7-Cyclopropyl-3-(hydroxymethyl)-6-[(1-naphthyl)methyl]-1-thia-3a-aza-4-indanone,
(3R)-6-[(1-Naphthyl)methyl]-4-oxo-7-(2-thienyl)-1-thia-3a-aza-3-indancarboxylic acid,
5-Cyclopropyl-4-[(1-naphthyl)methyl]-2-oxo-8-(1H-1,2,3-triazol-4-yl)-7-thia-1-azabicyclo[4.3.0]nona-3,5,8-triene-9-carboxylic acid,
8-Benzyl-5-cyclopropyl-4-[(1-naphthyl)methyl]-2-oxo-7-thia-1-azabicyclo[4.3.0]nona-3,5,8-triene-9-carboxylic acid,
(3R)-7-Cyclopropyl-6-[(2,3-dichlorophenyl)methyl]-4-oxo-1-thia-3a-aza-3-indancarboxylic acid,
(3R)-7-Cyclopropyl-6-[(1-naphthyl)methyl]-4-oxo-1-thia-3a-aza-3-indancarboxamide,
{(3R)-7-Cyclopropyl-6-[(1-naphthyl)methyl]-4-oxo-1-thia-3a-aza-3-indanyl}(phenylsulfonylamino)formaldehyde, (3R)-7-Isopropyl-6-[(1-naphthyl)methyl]-4-oxo-1-thia-3a-aza-3-indancarboxylic acid,
(3R)-7-Cyclopropyl-6-methyl-4-oxo-1-thia-3a-aza-3-indancarboxylic acid,
(3R)-6-[(p-Chlorophenyl)methyl]-7-cyclopropyl-4-oxo-1-thia-3a-aza-3-indancarboxylic acid,
{(3R)-7-Cyclopropyl-6-[(1-naphthyl)methyl]-4-oxo-1-thia-3a-aza-3-indanyl}(methylsulfonylamino)formaldehyde,
(3R)-7-Cyclopropyl-4-oxo-6-[(m-tolyl)methyl]-1-thia-3a-aza-3-indancarboxylic acid,
(3R)-7-Isopropyl-4-oxo-6-[2-(m-tolyl)ethyl]-1-thia-3a-aza-3-indancarboxylic acid,
7-(1-Methyl-1H-indol-3-yl)-6-[(1-naphthyloxy)methyl]-4-oxo-1-thia-3a-aza-3-indancarboxylic acid,
(3R)-6-[(4-Bromo-1-naphthyl)methyl]-7-cyclopropyl-4-oxo-1-thia-3a-aza-3-indancarboxylic acid,
7-Cyclopropyl-6-[(1-naphthyl)methyl]-1-thia-3a-aza-4-indanone,
(3R)-7-Cyclopropyl-5-(hydroxymethyl)-6-[(1-naphthyl)methyl]-4-oxo-1-thia-3a-aza-3-indancarboxylic acid,
(3 S)-3-Amino-7-cyclopropyl-6-[(1-naphthyl)methyl]-1-thia-3a-aza-4-indanone,
(2R,3R)-7-Cyclopropyl-6-[(1-naphthyl)methyl]-4-oxo-2-phenyl-1-thia-3a-aza-3-indancarboxylic acid,
(2S,3R)-7-Cyclopropyl-2-methoxy-6-[(1-naphthyl)methyl]-4-oxo-1-thia-3a-aza-3-indancarboxylic acid,
7-Cyclopropyl-4-oxo-6-{[m-(trifluoromethyl)phenyl]methyl}-1-thia-3a-aza-3-indancarboxylic acid,
2-{2-[1-(Hydroxymethyl)propylamino]ethylamino}butyl 7-cyclopropyl-6-[(1-naphthyl)methyl]-4-oxo-1-thia-3a-aza-3-indancarboxylate,
{7-Cyclopropyl-6-[(1-naphthyl)methyl]-4-oxo-1-thia-3a-aza-3-indanyl}(2-isonicotinoylhydrazino)formaldehyde,
7-Cyclopropyl-6-[(4-methoxy-1-naphthyl)methyl]-4-oxo-1-thia-3a-aza-3-indancarboxylic acid,
(3R)-7-(Dimethylamino)-6-[(1-naphthyl)methyl]-4-oxo-1-thia-3a-aza-3-indancarboxylic acid,
(3R)-5-Bromo-7-cyclopropyl-6-[(1-naphthyl)methyl]-4-oxo-1-thia-3a-aza-3-indancarboxylic acid,
7-Cyclopropyl-6-[(1-naphthyl)methyl]-1,1-dioxo-4-oxo-1-thia-3a-aza-3-indancarboxylic acid,
(3R)-7-Cyclopropyl-4-oxo-6-[(2,3-xylidino)methyl]-1-thia-3a-aza-3-indancarboxylic acid,
7-Cyclopropyl-6-[(1-naphthyl)methyl]-1-oxo-4-oxo-1-thia-3a-aza-3-indancarboxylic acid,
(3R)-7-Ethoxy-6-[(1-naphthyl)methyl]-4-oxo-1-thia-3a-aza-3-indancarboxylic acid,
(3R)-6-[(1-Naphthyl)methyl]-4-oxo-7-(trifluoromethyl)-1-thia-3a-aza-3-indancarboxylic acid,
(3R)-7-Isobutoxy-6-[(1-naphthyl)methyl]-4-oxo-1-thia-3a-aza-3-indancarboxylic acid,
(3R)-7-Cyclopropyl-6-[(2-methoxy-1-naphthyl)methyl]-4-oxo-1-thia-3a-aza-3-indancarboxylic acid,
(3R)-7-(Cyclopropylmethoxy)-6-[(1-naphthyl)methyl]-4-oxo-1-thia-3a-aza-3-indancarboxylic acid,
7-Cyclopropyl-6-[(2-methyl-1-aza-2-bora-1H-naphth-5-yl)methyl]-4-oxo-1-thia-3a-aza-3-indancarboxylic acid,
7-Cyclopropyl-6-[(2-methyl-1-aza-2-bora-1H-naphth-5-yloxy)methyl]-4-oxo-1-thia-3a-aza-3-indancarboxylic acid,
7-Cyclopropyl-6-[(2-methyl-1-aza-2-bora-1H-naphth-8-yl)methyl]-4-oxo-1-thia-3a-aza-3-indancarboxylic acid,
7-Cyclopropyl-6-[(2-methyl-1-aza-2-bora-1H-naphth-8-yloxy)methyl]-4-oxo-1-thia-3a-aza-3-indancarboxylic acid,
1H-imidazol-1-ium 7-(benzo[d]oxazol-2-yl)-8-cyclopropyl-5-oxo-3,5-dihydro-2H-thiazolo[3,2-a]pyridine-3-carboxylate,
1H-imidazol-1-ium 8-cyclopropyl-7-(3-(naphthalen-1-yl)isoxazol-5-yl)-5-oxo-3,5-dihydro-2H-thiazolo[3,2-a]pyridine-3-carboxylate,
1H-imidazol-1-ium 8-cyclopropyl-5-oxo-7-(3-(3-(trifluoromethyl)phenyl)isoxazol-5-yl)-3,5-dihydro-2H-thiazolo[3,2-a]pyridine-3-carboxylate,
1H-imidazol-1-ium 8-cyclopropyl-5-oxo-7-(3-(thiophen-2-yl)isoxazol-5-yl)-3,5-dihydro-2H-thiazolo[3,2-a]pyridine-3-carboxylate,
1H-imidazol-1-ium 8-cyclopropyl-5-oxo-7-(3-phenylisoxazol-5-yl)-3,5-dihydro-2H-thiazolo[3,2-a]pyridine-3-carboxylate,
1H-imidazol-1-ium 6-bromo-7-(naphthalen-1-ylmethyl)-5-oxo-8-(3-phenylisoxazol-5-yl)-3,5-dihydro-2H-thiazolo[3,2-a]pyridine-3-carboxylate,
1H-imidazol-1-ium 7-(naphthalen-1-ylmethyl)-5-oxo-8-(3-phenyl-4,5-dihydroisoxazol-5-yl)-3,5-dihydro-2H-thiazolo[3,2-a]pyridine-3-carboxylate,
1H-imidazol-1-ium 8-ethynyl-7-(naphthalen-1-ylmethyl)-5-oxo-3,5-dihydro-2H-thiazolo[3,2-a]pyridine-3-carboxylate,
1H-imidazol-1-ium 7-(naphthalen-1-ylmethyl)-5-oxo-8-(3-phenylisoxazol-5-yl)-3,5-dihydro-2H-thiazolo[3,2-a]pyridine-3-carboxylate,
1H-imidazol-1-ium 8-(3-(naphthalen-1-yl)isoxazol-5-yl)-7-(naphthalen-1-ylmethyl)-5-oxo-3,5-dihydro-2H-thiazolo[3,2-a]pyridine-3-carboxylate,
1H-imidazol-1-ium 8-cyclopropyl-7-(naphthalen-1-ylmethyl)-5-oxo-3,5-dihydro-2H-thiazolo[3,2-a]pyridine-3-carboxylate,
8-cyclopropyl-5-oxo-7-(5-(3-(trifluoromethyl)phenyl)isoxazol-3-yl)-2,3-dihydrothiazolo[3,2-a]pyridine-3-carboxylic acid,
8-cyclopropyl-7-(5-(naphthalen-1-yl)isoxazol-3-yl)-5-oxo-2,3-dihydrothiazolo[3,2-a]pyridine-3-carboxylic acid,
8-cyclopropyl-7-(3-(naphthalen-2-yl)isoxazol-5-yl)-5-oxo-2,3-dihydrothiazolo[3,2-a]pyridine-3-carboxylic acid,
1H-imidazol-1-ium 7-(3-(benzo[d][1,3]dioxol-5-yl)isoxazol-5-yl)-8-cyclopropyl-5-oxo-2,3-dihydrothiazolo[3,2-a]pyridine-3-carboxylate,
1H-imidazol-1-ium 7-(3-(anthracen-9-yl)isoxazol-5-yl)-8-cyclopropyl-5-oxo-2,3-dihydrothiazolo[3,2-a]pyridine-3-carboxylate,
7-(3-(3,5-bis(trifluoromethyl)phenyl)isoxazol-5-yl)-8-cyclopropyl-5-oxo-2,3-dihydrothiazolo[3,2-a]pyridine-3-carboxylic acid,
8-cyclopropyl-7-(3-methylisoxazol-5-yl)-5-oxo-2,3-dihydrothiazolo[3,2-a]pyridine-3-carboxylic acid,
7-(3-(tert-butylamino)imidazo[1,2-a]pyridin-2-yl)-8-cyclopropyl-5-oxo-2,3-dihydrothiazolo[3,2-a]pyridine-3-carboxylic acid,
7-(3-(benzylamino)imidazo[1,2-a]pyridin-2-yl)-8-cyclopropyl-5-oxo-2,3-dihydrothiazolo[3,2-a]pyridine-3-carboxylic acid,
8-cyclopropyl-7-(3-((naphthalen-1-ylmethyl)amino)imidazo[1,2-a]pyridin-2-yl)-5-oxo-2,3-dihydrothiazolo[3,2-a]pyridine-3-carboxylic acid, 8-cyclopropyl-5-oxo-7-(3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-6-chloroimidazo[1,2-a]pyridin-2-yl)-8-cyclopropyl-5-oxo-2,3-dihydrothiazolo[3,2-a]pyridine-3-carboxylic acid, 7-(6-chloro-3-((naphthalen-1-ylmethyl)amino)imidazo[1,2-a]pyridin-2-yl)-8-cyclopropyl-5-oxo-2,3-dihydrothiazolo[3,2-a]pyridine-3-carboxylic acid, 7-(3-(benzylamino)-6-chloroimidazo[1,2-a]pyridin-2-yl)-8-cyclopropyl-5-oxo-2,3-dihydrothiazolo[3,2-a]pyridine-3-carboxylic acid, 7-(6-chloro-3-((3-(trifluoromethyl)benzyl)amino)imidazo[1,2-a]pyridin-2-yl)-8-cyclopropyl-5-oxo-2,3-dihydrothiazolo[3,2-a]pyridine-3-carboxylic acid, 7-(3-(tert-butylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-7-(3-((naphthalen-1-ylmethyl)amino)-7-(trifluoromethyl)imidazo[1,2-a]pyridin-2-yl)-5-oxo-2,3-dihydrothiazolo[3,2-a]pyridine-3-carboxylic acid, 7-(3-(benzylamino)-7-(trifluoromethyl)imidazo[1,2-a]pyridin-2-yl)-8-cyclopropyl-5-oxo-2,3-dihydrothiazolo[3,2-a]pyridine-3-carboxylic acid, 8-cyclopropyl-5-oxo-7-(7-(trifluoromethyl)-3-((3-(trifluoromethyl)benzyl)amino)imidazo[1,2-a]pyridin-2-yl)-2,3-dihydrothiazolo[3,2-a]pyridine-3-carboxylic acid, 7-(3-(tert-butylamino)-7-methoxyimidazo[1,2-a]pyridin-2-yl)-8-cyclopropyl-5-oxo-2,3-dihydrothiazolo[3,2-a]pyridine-3-carboxylic acid, 8-cyclopropyl-7-(7-methoxy-3-((naphthalen-1-ylmethyl)amino)imidazo[1,2-a]pyridin-2-yl)-5-oxo-2,3-dihydrothiazolo[3,2-a]pyridine-3-carboxylic acid, 7-(3-(benzylamino)-7-methoxyimidazo[1,2-a]pyridin-2-yl)-8-cyclopropyl-5-oxo-2,3-dihydrothiazolo[3,2-a]pyridine-3-carboxylic acid, or 8-cyclopropyl-7-(7-methoxy-3-((3-(trifluoromethyl)benzyl)amino)imidazo[1,2-a]pyridin-2-yl)-5-oxo-2,3-dihydrothiazolo[3,2-a]pyridine-3-carboxylic acid.

10. The composition according to claim 1, wherein the compound of Formula I is a compound of Formula Ia:

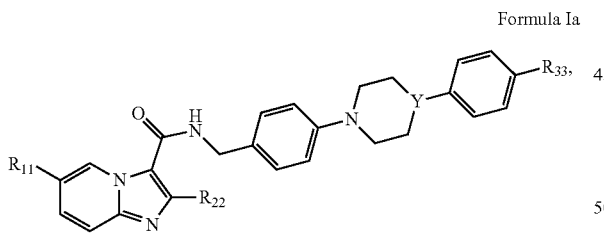

Formula Ia wherein $R_{11}$, $R_{22}$, Y and $R_{33}$ are as defined in claim 1.

11. The composition according to claim 10, wherein the compound of Formula Ia is:

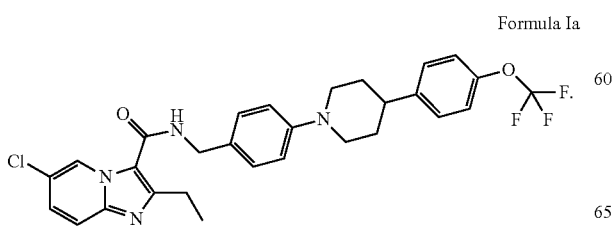

Formula Ia

12. The composition according to claim 1, further comprising one or more of the following drugs against tuberculosis: isonicotinylhydrazide, bedaquiline, ethionamide, pretomanid, 4-aminosalisalicylic acid, rifampin, pyrazinamide, ethambutol, or a pharmaceutically acceptable salt of any one of the foregoing drugs against tuberculosis.

13. A method for treating tuberculosis comprising administering to a mammal in need thereof an effective amount of a compound of Formula I:

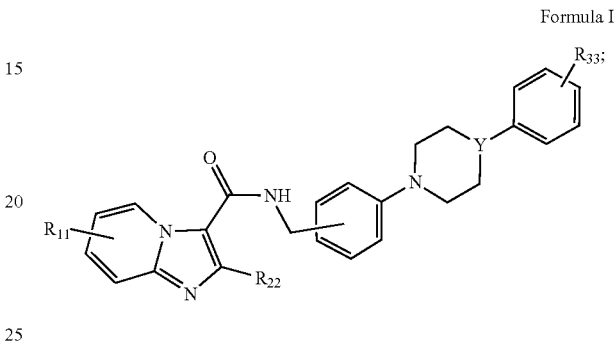

Formula I or a pharmaceutically acceptable salt thereof, wherein:

$R_{11}$ is selected from the group consisting of F, Cl, Br, I, methyl, methoxy, CN, $CF_3$ and $OCF_3$, $R_{22}$ is $C_1$-$C_4$ alkyl, Y is CH or N, $R_{33}$ is selected from the group consisting of:

a) F, Cl, Br, I, methyl, methoxy, CN, $CF_3$ and $OCF_3$, b) C(O)OMe, c) C(O)OH, and d) $CH_2OH$; and (ii) an effective amount of a compound of Formula II

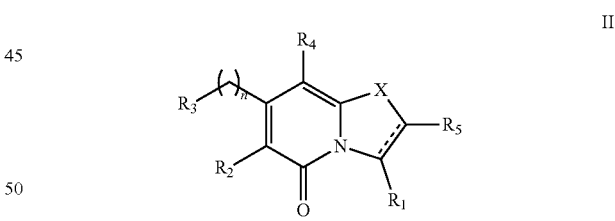

II or a pharmaceutically acceptable salt thereof, wherein $R_1$ is selected from the group consisting of:

a) C(O)OH, b) tetrazolyl, c) $CH_2OH$, d) $C(O)NR_{6a}R_{6b}$, e) $C(O)NHSO_2R_7$, f) $C(O)OR_8$, g) $NH_2$, h) H, i)

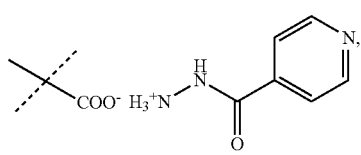

j)

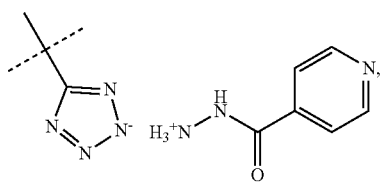

k)

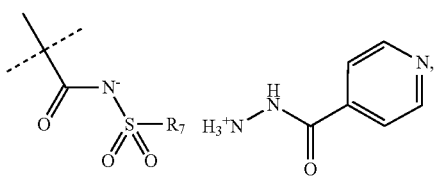

and l) imidazole carboxylate, $R_2$ is selected from the group consisting of:
a) H,
b) Cl, F, Br or I,
c) $CH_2OH$,
d) $C_1$-$C_4$alkyl, and
e) $NY_1Y_2$, $R_3$ is selected from the group consisting of:
a) 1-naphthyl, 2-naphthyl or 1-naphthyloxy, each independently substituted with 0, 1, 2 or 3 substituents selected from the group consisting of methyl, fluoro, chloro, bromo, cyano and methoxy,
b) phenyl substituted with 0, 1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl,
d) 2-(3-methyl)phenylmethylene,
e) benzothiophen-2-yl
f) H,
g) $C_1$-$C_4$alkyl,
h) 2-methyl-1-aza-2-bora-1H-naphth-5-yloxy,
i) 2-methyl-1-aza-2-bora-1H-naphth-5-yl,
j) isoxazol-5-yl optionally substituted with methyl, 1-naphthyl, 2-naphtyl, 1-anthryl, m-trifluoromethylphenyl, 3,5-ditrifluoromethylphenyl, 3,4-methylenedioxyphenyl, thiophene or phenyl,
k) isoxazol-3-yl substituted with m-trifluoromethylphenyl or 1-naphtyl,
l) benzoxazole-2-yl, and m)

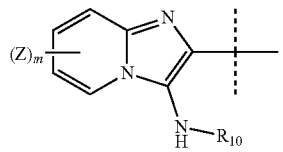

$R_4$ is selected from the group consisting of:
a) $C_1$-$C_4$alkyl substituted by 0, 1, 2, 3 or 4 fluoro,
b) $C_3$-$C_6$cycloalkyl,
c) $C_1$-$C_4$alkoxy substituted by 0, 1, 2, 3 or 4 fluoro,
d) $C_3$-$C_6$cycloalkoxy,
e) a 3-, 4-, 5- or 6-membered heterocycle, substituted with 0 or 1 substituent selected from the group consisting of phenyl and 1-naphthyl,
f) N-methyl 3-indolyl,
g) $NR_{9a}R_{9b}$, and
h) $C_2$-$C_4$alkynyl, $R_5$ is selected from the group consisting of:
a) H,
b) phenyl substituted with 0, 1, 2 or 3 methyl group(s),
c) benzyl,
d) thienyl,
e) $C_1$-$C_4$alkoxy, and
f) a 3-, 4-, 5- or 6-membered heterocycle, and in the above definitions:

$R_{6a}$ is selected from the group consisting of H and $C_1$-$C_4$alkyl,
$R_{6b}$ is selected from the group consisting of H, $C_1$-$C_4$alkyl, $C_1$-$C_4$alkoxy and isonicotinoylamino;
$R_7$ is $C_1$-$C_4$alkyl or phenyl,
$R_8$ represents 2-{2-[1-(hydroxymethyl)propylamino]ethylamino}butyl),
$R_{9a}$ represents $C_1$-$C_4$alkyl,
$R_{9b}$ represents $C_1$-$C_4$alkyl,
$R_{10}$ represents H; $C_1$-C4alkyl substituted with 0, 1, 2 or 3 F; benzyl substituted with 0 or 1 trifluoromehtyl; or naphtalen-1-yl-methylene,
$Y_1$ and $Y_2$ each independently represents hydrogen, methyl, $CH_3S(O)_2$ or $C(O)CH_3$, or
$Y_1$ and $Y_2$ together form $CH_2CH_2CH_2CH_2$ or $CH_2CH_2CH_2CH_2CH_2$,
m is 0 or 1,
n is 0 or 1,
X is S, SO or $SO_2$, and
Z represents $C_1$-$C_4$alkyl substituted with 0, 1, 2 or 3 F; $C_1$-$C_4$alkoxy substituted with 0, 1, 2 or 3 F; or a halogen selected from Cl, F, Br or I, thereby treating tuberculosis.

14. The method according to claim 13, wherein said tuberculosis is active, latent and/or drug-resistant tuberculosis.

15. A method for sensitizing tuberculosis bacteria to treatment with a drug against tuberculosis as defined in claim 1 comprising administering to a mammal in need thereof an effective amount of a compound of Formula II as defined in claim 1, thereby sensitizing tuberculosis bacteria to treatment with the drug against tuberculosis as defined in claim 1.

16. The method according to claim 15, wherein the method further comprises administering to the mammal in need thereof an effective amount of the drug against tuberculosis, thereby treating tuberculosis.

17. A method for sensitizing tuberculosis bacteria to being eradicated by a drug against tuberculosis as defined in claim 1 comprising contacting tuberculosis bacteria with an effective amount of a compound of Formula II of claim 1, thereby sensitizing tuberculosis bacteria to being eradicated by the drug against tuberculosis as defined in claim 1.

18. The method according to claim 17, wherein the method further comprises contacting the tuberculosis bacteria with an effective amount of the drug against tuberculosis as defined in claim 1, thereby eradicating the tuberculosis bacteria.

19. The composition of claim 1 provided as a kit of parts, wherein the kit of parts comprises:

i) an effective amount of a compound of Formula I:

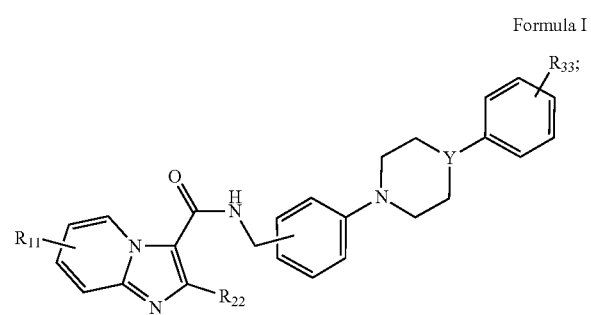

Formula I or a pharmaceutically acceptable salt thereof, wherein:

$R_{11}$ is selected from the group consisting of F, Cl, Br, I, methyl, methoxy, CN, $CF_3$ and $OCF_3$, $R_{22}$ is $C_1$-$C_4$ alkyl, Y is CH or N, $R_{33}$ is selected from the group consisting of:
a) F, Cl, Br, I, methyl, methoxy, CN, $CF_3$ and $OCF_3$,
b) C(O)OMe,
c) C(O)OH, and
d) $CH_2OH$;

ii) an effective amount of a compound of Formula II

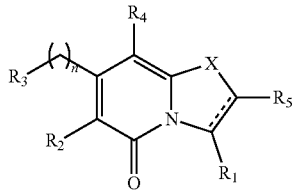

II or a pharmaceutically acceptable salt thereof, wherein $R_1$ is selected from the group consisting of:
a) C(O)OH,
b) tetrazolyl,
c) $CH_2OH$,
d) $C(O)NR_{6a}R_{6b}$,
e) $C(O)NHSO_2R_7$,
f) $C(O)OR_8$,
g) $NH_2$,
h) H, i)

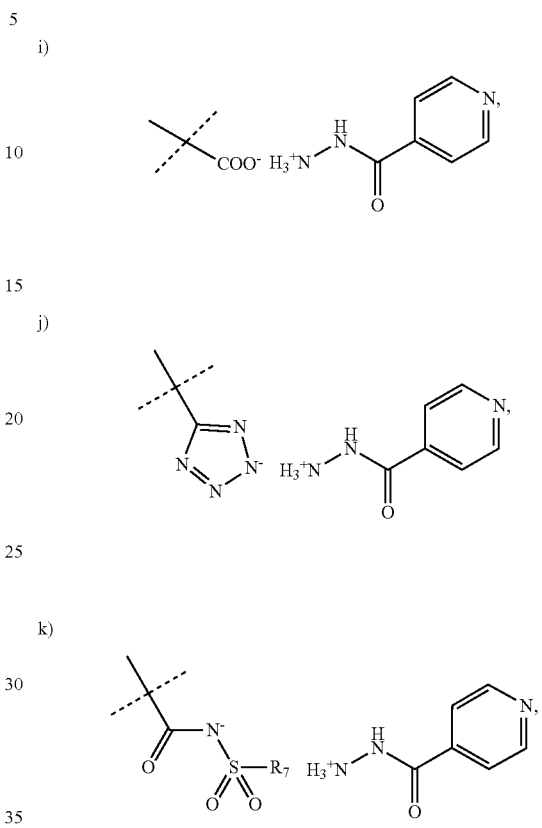

j)

k)

and
1) imidazole carboxylate, $R_2$ is selected from the group consisting of:
a) H,
b) Cl, F, Br or I,
c) $CH_2OH$,
d) $C_1$-$C_4$alkyl, and
e) $NY_1Y_2$, $R_3$ is selected from the group consisting of:
a) 1-naphthyl, 2-naphthyl or 1-naphthyloxy, each independently substituted with 0, 1, 2 or 3 substituents selected from the group consisting of methyl, fluoro, chloro, bromo, cyano and methoxy,
b) phenyl substituted with 0,1, 2 or 3 substituents independently selected from the group consisting of methyl, fluoro, chloro, cyano and trifluoromethyl,
c) aminophenyl substituted with 0, 1, 2 or 3 substituents independently selected from the group consisting of methyl, fluoro, chloro and trifluoromethyl
d) 2-(3-methyl)phenylmethylene,
e) benzothiophen-2-yl
f) H,
g) $C_1$-$C_4$alkyl,
h) 2-methyl-1-aza-2-bora-1H-naphth-5-yloxy,
i) 2-methyl-1-aza-2-bora-1H-naphth-5-yl,
j) isoxazol-5-yl optionally substituted with methyl, 1-naphthyl, 2-naphthyl, 1-anthryl, m-trifluoromethylphenyl, 3,5-ditrifluoromethylphenyl, 3,4-methylenedioxyphenyl, thiophene or phenyl, k) isoxazol-3-yl substituted with m-trifluoromethylphenyl or 2-naphthyl,
l) benzoxazole-2-yl, and

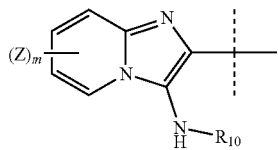

R$_4$ is selected from the group consisting of:
a) C$_1$-C$_4$alkyl substituted by 0, 1, 2, 3 or 4 fluoro,
b) C$_3$-C$_6$cycloalkyl,
c) C$_1$-C$_4$alkoxy substituted by 0, 1, 2, 3 or 4 fluoro,
d) C$_3$-C$_6$cycloalkoxy,
e) a 3-, 4-, 5- or 6-membered heterocycle, substituted with 0 or 1 substituent selected from the group consisting of phenyl and 1-naphthyl,
f) N-methyl 3-indolyl,
g) NR$_{9a}$R$_{9b}$, and
h) C$_2$-C$_4$alkynyl,
R$_5$ is selected from the group consisting of:
a) H,
b) phenyl substituted with 0, 1, 2 or 3 methyl group(s),
c) benzyl,
d) thienyl,
e) C$_1$-C$_4$alkoxy, and
f) a 3-, 4-, 5- or 6-membered heterocycle,
and in the above definitions:
R$_{6a}$ is selected from the group consisting of H and C$_1$-C$_4$alkyl,
R$_{6b}$ is selected from the group consisting of H, C$_1$-C$_4$alkyl, C$_1$-C$_4$alkoxy and isonicotinoylamino;
R$_7$ is C$_1$-C$_4$alkyl or phenyl,
R$_8$ represents 2-{2-[1-(hydroxymethyl)propylamino]ethylamino}butyl),
R$_{9a}$ represents C$_1$-C$_4$alkyl,
R$_{9b}$ represents C$_1$-C$_4$alkyl,
R$_{10}$ represents H; C$_1$-C4alkyl substituted with 0, 1, 2 or 3 F; benzyl substituted with 0 or 1 trifluoromehtyl; or naphthalen-1-yl-methylene,
Y$_1$ and Y$_2$ each independently represents hydrogen, methyl, CH$_3$S(O)$_2$ or C(O)CH$_3$, or
Y$_1$ and Y$_2$ together form CH$_2$CH$_2$CH$_2$CH$_2$ or CH$_2$CH$_2$CH$_2$CH$_2$CH$_2$,
m is 0 or 1,
n is 0 or 1,
X is S, SO or SO$_2$, and
Z represents C$_1$-C$_4$alkyl substituted with 0, 1, 2 or 3 F; C$_1$-C$_4$alkoxy substituted with 0, 1, 2 or 3 F; or a halogen selected from Cl, F, Br or I; and
optionally instructions of use.

* * * * *